(12) United States Patent
Wang et al.

(10) Patent No.: US 10,851,174 B2
(45) Date of Patent: Dec. 1, 2020

(54) CORE FUCOSYLATED GLYCOPEPTIDES AND GLYCOPROTEINS: CHEMOENZYMATIC SYNTHESIS AND USES THEREOF

(75) Inventors: Lai-Xi Wang, Ellicott City, MD (US); Wei Huang, Dundalk, MD (US); John Giddens, Chesapeake, VA (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 257 days.

(21) Appl. No.: 13/411,733

(22) Filed: Mar. 5, 2012

(65) Prior Publication Data
US 2012/0226024 A1 Sep. 6, 2012

Related U.S. Application Data

(60) Provisional application No. 61/448,702, filed on Mar. 3, 2011.

(51) Int. Cl.
| | | |
|---|---|---|
| C07K 16/28 | (2006.01) | |
| C07K 16/00 | (2006.01) | |
| C12P 21/00 | (2006.01) | |
| C07K 16/18 | (2006.01) | |
| C12N 9/24 | (2006.01) | |

(52) U.S. Cl.
CPC .......... *C07K 16/2887* (2013.01); *C07K 16/00* (2013.01); *C07K 16/18* (2013.01); *C12N 9/2402* (2013.01); *C12P 21/005* (2013.01); *C07K 2317/41* (2013.01)

(58) Field of Classification Search
None
See application file for complete search history.

(56) References Cited

U.S. PATENT DOCUMENTS

| | | | |
|---|---|---|---|
| 7,524,821 B2 | 4/2009 | Wang et al. | |
| 7,604,804 B2 | 10/2009 | Wang et al. | |
| 7,728,106 B2 | 6/2010 | Wang | |
| 7,807,405 B2 | 10/2010 | Wang | |
| 2005/0064540 A1* | 3/2005 | Defrees et al. | 435/68.1 |
| 2009/0117154 A1 | 5/2009 | Wang et al. | |
| 2011/0070607 A1 | 3/2011 | Wang | |

FOREIGN PATENT DOCUMENTS

EP          1461445          11/2002

OTHER PUBLICATIONS

Fan et al. 'Remarkable transglycosylation activity of glycosynthase mutants of endo-D, an endo-β-N-acetylglucosaminidase from *Streptococcus pneumoniae*.' J. Biol. Chem. 287(14):11272-11281, 2012.*
https://www.accessdata.fda.gov/drugsatfda_docs/label/2002/inflcen062802LB.pdf.*

Abbott, D. W. et al. (2009) *J. Biol. Chem.* 284, 11676-11689.
Anthony, R.M. et al., *Science*, 2008, 320, 373-376.
Bennett, C.S. et al., *Chem. Soc. Rev.*, 2007, 36, 1227-1238.
Bernardes, G.J. et al., *ACS Chem Biol*, 2009, 4, 703-713.
Brameld, K.A. et al., 3rd, *J. Mol. Biol.* 1998, 280, 913-923.
Buskas, T. et al., *Glycobiology*, 2006, 16, 113R-136R.
Camilli, R. et al., *Antimicrob. Agents Chemother.* 52 (2), 619-625 (2008)].
Eller, S. et al., *Angew. Chem. Int. Ed.*, 2007, 46, 4173-4175.
Fujita, K. et al., *Biochem. Biophys. Res. Commun.*, 2000, 267, 134-138.
Gamblin, D.P. et al., *Chem. Rev.*, 2009, 109, 131-163.
Grogan, M. J. et al., *Annu. Rev. Biochem.*, 2002, 71, 593-634.
Hamilton, S.R. et al., *Science*, 2006, 313, 1441-1443.
Hamilton, S.R. et al., *Science*, 2003, 301, 1244-1246.
Haneda, K. et al., *Res.*, 1996, 292, 61-70.
Heidecke, C.D. et al., *Chembiochem*, 2008, 9, 2045-2051.
Hirano, K. et al., *Angew. Chem. Int. Ed.*, 2009, 48, 9557-9560.
Huang, W. Et al.,*J Am Chem Soc*, 2009, 131, 2214-2223.
Huang, W. et al., *Chembiochem*, 2010, 11, 1350-1355.
Huang, W. Et al., *Org. Biomol. Chem.* 2010, 8, 5224-5233.
Kaneko, Y. et al., *Science*, 2006, 313, 670-673.
Kirsch, P. et al., *Bioorg Med Chem*, 1995, 3, 1631-1636.
Kuhn, P. et al., *Biochemistry* 1994, 33, 11699-11706.
Li, B. et al., *Org Lett*, 2006, 8, 3081-3084.
Li, B. et al., *J Am Chem Soc*, 2005, 127, 9692-9693.
Li, H. et al., *Bioorg. Med. Chem. Lett.*, 2005, 15, 895-898.
Li, H. et al., *J. Org. Chem.*, 2005, 70, 9990-9996.
Macmillan, D. et al., *Angew. Chem. Int. Ed.*, 2004, 43, 1355-1359.
Muramatsu, H. et al., *Journal of Biochemistry*, 2001, 129, 923-928.
Ochiai, H. et al., *J Am Chem Soc*, 2008, 130, 13790-13803.
Parsons, T.B. et al., *Org Biomol Chem*, 2010, 8, 1861-1869.
Parsons, T.B. et al., *Org. Biomol. Chem.*, 2009, 7, 3128-3140.
Piontek, C. et al., *Angew. Chem. Int. Ed.*, 2009, 48, 1941-1945.
Piontek, C. et al., *Angew. Chem. Int. Ed.*, 2009, 48, 1936-1940.
Plummer, Jr., T.H. et al., *Anal. Biochem.* 1996, 235, 98-101.
Rao, V. et al., *Structure* 1995, 3, 449-457.

(Continued)

*Primary Examiner* — Nora M Rooney
(74) *Attorney, Agent, or Firm* — Tristan A. Fuierer; Marianne Fuierer; Olive Law Group, PLLC

(57) ABSTRACT

A chemoenzymatic method for the preparation of a core-fucoslyated glycoprotein or glycopeptide, including (a) providing an acceptor selected from the group consisting of a fucosylated GlcNAc-protein and fucosylated GlcNAc-peptide; and (b) reacting the acceptor with a donor substrate including an activated oligosaccharide moiety, in the presence of an endoglycosidase (ENGase) selected from Endo; F1, Endo-F2, Endo-F3, Endo-D and related glycosynthase mutants to transfer the oligosaccharide moiety to the acceptor and yield the structure defined core-fucosylated glycoprotein or glycopeptide. The donor substrate includes, in a specific implementation, a synthetic oligosaccharide oxazoline. A related method of fucosylated glycoprotein or fucosylated glycopeptide remodeling with a predetermined natural N-glycan or a tailor-made oligosaccharide moiety, and a method of remodeling an antibody to include a predetermined sugar chain to replace a heterogeneous sugar chain, are also described.

19 Claims, 24 Drawing Sheets

Specification includes a Sequence Listing.

(56) References Cited

OTHER PUBLICATIONS

Reddy, A. et al., *Glycobiology* 1998, 8, 633-636.
Rich, J.R. et al., *Nat Chem Biol*, 2009, 4, 206-215.
Rising, T. W. et al., *ChemBioChem*, 2006, 7, 1177-1180.
Rising, T. W. et al.,*Carbohydr Res*, 2006, 341, 1574-1596.
Rising, T. W. et al., *Chem. Eur. J.*, 2008, 14, 6444-6464.
Sun, B. et al., *Chemistry—A European Journal*, 2008, 14, 7072-7081.
Takegawa, K. et al., *Arch. Biochem. Biophys.*, 1997, 338, 22-28.
Tarentino, A.L. et al., *Methods Enzymol*. 1994, 230, 44-57.
Tarentino, A.L. et al., *Glycobiology* 1995, 5, 599-601.
Tarentino, S.L. et al., *J. Biol. Chem*. 1990, 265, 6961-6966.
Tarentino, A.L., *J. Biol. Chem.*, 268 (13), 9702-9708 (1993).
Tews, I. et al., *J. Am. Chem. Soc.* 1997, 119, 7954-7959.
Trimble, R.B., *J Biol Chem*, 1986, 261, 12000-12005.
Trimble, R.B. et al., *J. Biol. Chem.* 1991, 266, 1646-1651.
Uchiyama, T. et al., *Synlett*, 1996, 499-501.
Umekawa, M. et al., *J Biol Chem*, 2010, 285, 511-521.
Umekawa, M. et al. *J Biol Chem*, 2008, 283, 4469-4479.
Van Kasteren, S.I. et al., *Nature*, 2007, 446, 1105-1109.
Waddling, C.A. et al., *Biochemistry* 2000, 39, 7878-7885.
Walsh, G. et al., *Nat. Biotechnol.*, 2006, 24 (10), 1241-1252.
Wang, L.X., *Carbohydr. Res.*, 2008, 343, 1509-1522.
Wang, L.X. et al., *Curr Opin Chem Biol*, 2009, 13, 592-600.
Wei, Y. et al. *Biochemistry*, 2008, 47, 10294-10304.
Wildt, S. et al., *Nat. Rev. Microbiol.*, 2005, 3, 119-128.
Yamamoto, K. et al., *Biosci Biotechnol Biochem*, 1994, 58, 72-77.
Yamamoto, K. *J. Biosci. Bioeng.*, 2001, 92, 493-501.
Yamamoto, Y. et al., *J. Am. Chem. Soc.*, 2008, 130, 501-510.
Zeng, Y. et al., *Chem. Eur. J.*, 2006, 12, 3355-3364.
Myers, Michele M., et al.; "Chapter 6—Addressing Changes Associated with Technology Transfer: A Case Study," Current Trends in Monoclonal Antibody Development and Manufacturing, Biotechnology: Pharmaceutical Aspects, DOI 10.1007/978-0-387-76643-0_6, 2010.

* cited by examiner

```
Endo-F1    AVTGTTKANIKLESFTEVNDTNPLNNLNFTLKNSGKPLVDMVVLESANINYDAANDKVTV 60
Endo-F2    -AVNLSM-----LIAYRNSDHQISAGYYR-TWRDSATASGNLPSMRWLPDSLEMVVFPDY 54
Endo-F3    -ATALAGSNGVCIAYYITDGRNPTFKLK--DIPDKVEMVILFGLKYWS----LQDTTKLPGG 55

Endo-F1    SNNPMVQHLLTNRAKYLKPLQDKGIKVILSILGNHDRSGIAMLSTARAKAFAQELRN--TC 119
Endo-F2    TPPENAYWNTLKTN--YVPYLHKRGTKVTITLGDLNSATTGGQDSIGYSSWAKGIYDRWV 113
Endo-F3    TGMMGSFKSYKDLDTQIRSLQSRGIKVLQNTDRDVSWQSSKPGGFASAAAYGDAIKSIVI 115

Endo-F1    DLYNLDGVFFDDEYSAYQTPPPSGFVTPSMNAARBLAYETKQAMPMKLVTVYVYSRTSSF 179
Endo-F2    GEYNLDGIDIDIESS--PSGATLTKFVAATKALSK---YFGPKSGTGKTFVYDTNQNPTNFF 170
Endo-F3    DKWKLDGTSLDIEHSGAKPNPIPTFPGYAATGYN---GWYSGSMAATPAFLNVTSELTKYF 173

Endo-F1    PTAVDGVN------AGSYVDYAIHDYGGSYDLATNYPGLAKSGMVMSSQEFNQGRY 229
Endo-F2    IQTAPRYN------YVFLQAYGRSTTNLTTVS-GLYAPYISMKQFLPGFSFYEENG 219
Endo-F3    GTTAPNNKQLQIASGIDVYAWWKIMENFRNNFNYTQLQSYGANVSRTQLMMNYATG--TNK 232

Endo-F1    ATAQALRNIVTKGYGGHMIFAMDPNRSNFTSGQLPALRLIAKELYGDELVYSNTPYSKDW 289
Endo-F2    YPGNYIWNDVRYPQNGTGRA---YDVARWQPATGKRGGVFSYAIERDAPLTSSWDNTLRAPN 277
Endo-F3    IPASKMVFGAYAEGGTNQAANDVEVAKWTPTQGAKGGMMIYTNSNVSYANAVRDAVKN--- 290

Endo-F1    FRVTKDLIKIMNP 290
Endo-F2    -------------
Endo-F3    -------------
```

Figure 20

```
  1 mknpffeerrc rysirklsvg acslmigavl fvgpalaeet avpensgant elvsgesehs
 61 tneadkqneg  ehtrenklek  aegvataset aeaasaakpe ekagevvaet psaeakpksd
121 keteakpeat  nqgdeskpaa  eanktekevq pdvpkntekt lkpkeikfns weellkwepg
181 areddainrg  svvlasrrtg  hlvnekaske akvgalsntn skakdhasvg geefkayafd
241 ywqylpdsmvf weglvptpdv  idaghrngvp vygtlffnws nsiadqerfa ealkqdadgs
301 fpiarklvdm  akyygydgyf  ingettgdlv kplgekmrqf mlyskeyaak vnhpikyswy
361 damtynygry  hqdglgeyny  qfmqpegdkv padnffanfn wdkakndyti atanwigrnp
421 ydvfaglelq  gggsyktkvk  wndildengk lrislglfap dtitslgktg edyhknedif
481 ftgyqgdptg  qkpgdkdwyg  ianlvadrtp avgntfttsf ntghgkkwfv dgkvskdsew
541 nyrsvsgvlp  twrwwqtstg  eklraeydft dayngensik fsgdvagktd qdvrlystkl
601 evtektklrv  ahkgkgskv   ymafsttpdy kfddadawke ltlsdnwtne efdlsslagk
661 tiyavkiffe  hegavrkdyqf nlggltisdn hqepgspsf  svvkqslkna qeaeavvqfk
721 gnkdadfyev  yekdgdswkl  itgssttiy  lpkvsrsasa qgttgelkvv avgkngvrse
781 aattfdwgm   tvkdtslpkp  laenivpgat vidstfpkte ggegiegmln gtitlsdkw
841 ssaqlsgsvd  irltkprtvv  rwvmdhagag gesvndglmn tkdfdlyykd adgewklake
901 vrgnkahvtd  itldkpitaq  dwrlnvvtsd ngtpwkairi ynwkmyekld tesvnipmak
961 aaarslgnnk  vqvgfadvqa  gatitvydnp nsqtplatlk sevggdlasa plditngsgl
```

Figure 21

```
1021  lyyrtqlpgk  eisnvlavsv  pkddrriksv  sletgpkkts  yaegedidlr  ggvlrvqyeg
1081  gtedelirlt  hagvsvsgfd  thhkgeqnit  lqylgqpvna  nlsvtvtggd  easpktilgi
1141  evsqkpkkdy  lvgdsidlse  grfavaysnd  tmeehsftde  gveisgydaq  ktgrqtltlr
1201  ygghevnfdv  lvspkaalnd  eylkqklaev  eaaknkvvyn  faspevkeaf  lkaieaaeqv
1261  ikdheistqd  qvndrinkit  eahkalngge  kfkeekteld  rltgevqell  dakpnhpsgs
1321  alaplleknk  vlvekvdlsp  eelatakqsl  kdlvalliked  kpavfsdskt  gvevhfsnke
1381  ktvlkglkve  rvqasaeekk  yfagedahvf  eiegldekgq  dvdlsyasiv  kipiekdkkv
1441  kkvfflpegk  eavelafeqt  dshviftaph  fthyafvyes  aekpqpakpa  pqnkvlpkpt
1501  yqpasdqgka  pklevqeeky  afhrqehena  emlvgeqrvi  lggrdqilrh  vfevdenggr
1561  rlrstevige  aipeiveigt  kvktvpavva  tqekpaqnta  vkseeaaskql  pntgtadane
1621  aliaglaslg  laslaltlrr  kredkd
```

CORE FUCOSYLATED GLYCOPEPTIDES AND GLYCOPROTEINS: CHEMOENZYMATIC SYNTHESIS AND USES THEREOF

CROSS-REFERENCE TO RELATED APPLICATION

The present application claims priority to U.S. Provisional Application No. 61/448,702 filed on Mar. 3, 2011, the contents of the application is hereby incorporated by reference herein for all purposes.

GOVERNMENT RIGHTS IN INVENTION

This invention was made with government support under Grant Number GM080374 awarded by the National Institutes of Health. The government has certain rights in the invention.

BACKGROUND OF THE INVENTION

Field of the Invention

The invention relates to glycoprotein synthesis, and more particularly, to the synthesis of structure defined core-fucosylated glycopeptides wherein one or more oligosaccharide sugar chains with a predetermined number of sugar moieties are added to a α-1,6-fucosylated N-acetylglucosamine (GlcNAc)-containing peptide or protein to form core-fucosylated glycopeptides and glycoproteins.

Description of the Related Art

Glycosylation is a remarkable strategy taken by nature to expand the biological information of a relatively concise human genome. The oligosaccharide components of glycoproteins not only affect protein's structure and stability, but also directly participate in many molecular recognition processes such as cell adhesion, differentiation, tumor metastasis, and host-pathogen interactions [1-6]. Ample examples have shown that subtle changes in the glycan structures of glycoproteins can result in significant differences in functions [7-11]. Core fucosylation, that being, the attachment of an α-1,6-linked fucose to the innermost GlcNAc moiety of asparagine (N)-linked glycans, is a natural modification frequently found in natural and mammalian cell line-expressed N-glycoproteins.

It has been shown that core fucosylation affects N-glycan conformations and regulates the interactions between N-glycans and glycan-binding proteins including various lectins [12-14, 19]. For example, the presence of core fucose on IgG antibody's Fc glycans significantly impacts the binding of the Fc domain to the Fc γIIIa receptor on a cell surface and which is responsible for antibody-dependent cellular cytotoxicity (ADCC) [8, 15-17]. After the antibody's recognition and binding to a target cell, ADCC and other effector functions are triggered through the binding of the antibody's Fc region to receptors. More and more evidence have shown that different glycosylation forms can exert significantly different effects on the properties of a given therapeutic antibody, some sugar chains are beneficial, while others are detrimental.

A typical immunoglobulin G (IgG) antibody is composed of two light and two heavy chains that are associated with each other to form three major domains connected through a flexible hinge region: the two identical antigen-binding (Fab) regions and the constant (Fc) region. It is noted that there are heterogeneous glycosylation states of the human IgG when expressed in mammalian cell lines (e.g., CHO cell lines), and isolation of human IgG having a particular glycosylation state from this mixture is extremely difficult. Small amounts of impurities of a highly active species can dramatically interfere with the results and data interpretation. Generation of high-affinity mAbs to Fc receptors, such as the Fc γIIIa receptor, may overcome the problem of polymorphism of the Fcγ receptor variants, thus enhancing the clinical efficacy of therapeutic mAbs. Additionally, it was reported that core-fucosylation increased significantly for some cancer cells, suggesting that core-fucosylated N-glycans and/or glycoproteins could serve as novel biomarkers for diagnosis [18-21].

Notably, functional glycomics studies aiming to understand the detailed structure-function relationships of glycosylation are often hampered by the difficulties to obtain structurally well-defined complex oligosaccharides and glycoconjugates either from natural sources or from synthesis. The past two decades have witnessed a remarkable advance in synthetic method development for making homogeneous glycopeptides and glycoproteins [22-36]. Nevertheless, chemical and chemoenzymatic synthesis of sialylated and fucosylated complex glycopeptides or glycoproteins is still a challenging task, because of the labile nature of α-sialyl/α-fucosyl glycosidic linkages during synthetic manipulations [29, 37, 38]. Late-stage enzymatic introduction of the core fucose by α-1,6-fucosyltransferase (Fut8) does not seem to be feasible because Fut-8 only accepts the truncated N-glycan core as a substitute for α-1,6-fucosylation and does not recognize sialylated and/or galactosylated N-glycan substrates.

Transglycosylation by endo-α-N-acetylglucosaminidases (ENGases), a class of endoglycosidases that inherently cleave N-glycans from glycoproteins, have recently been explored for glycopeptide synthesis and glycosylation remodeling of glycoproteins [39-56]. Two GH family 85 ENGases, the Endo-A from *Arthrobacter protophormiae* and the Endo-M from *Mucor hiemalis*, have been particularly useful for native ligation between a pre-assembled oligosaccharide oxazoline and a GlcNAc-peptide/protein to form a homogeneous glycopeptide or glycoprotein in a regio- and stereo-specific manner without the need of any protecting groups. Thus, this chemoenzymatic method is highly convergent and permits independent synthetic manipulations of the glycan and polypeptide portions. Recently, this method has been extended to the synthesis of sialylated complex glycopeptides and sialylated ribonuclease C [56]. However, to this date, the discussed chemoenzymatic method was not feasible for the synthesis of core-fucosylated glycopeptides. As such, so far there were no reports of any endoglycosidases capable of transferring oligosaccharides to core-fucosylated GlcNAc acceptor.

As such, there is a need for proper and consistent glycosylation in developing core-fucosylated glycopeptides and glycoproteins to be used for development and production of therapeutic agents while reducing negative effects such as allergy problems or undesired immune responses and conferring significant and consistent stability and activity.

SUMMARY OF THE INVENTION

The present invention relates to the synthesis of fucosylated glycopeptides or glycoproteins wherein a desired sugar chain is added to a fucosylated GlcNAc-protein acceptor by transglycosylation to form structure defined core-fucosylated glycopeptides or glycoproteins. As such, the present invention allows for the synthesis and remodeling of therapeutic glycopeptide or glycoprotein drugs, glycoprotein hormones, cytokines, therapeutic antibodies thereby providing for certain activities, such as, prolonged half-life time in vivo, less immunogenicity, enhanced in vivo activity, increased targeting ability, and/or ability to deliver a therapeutic agent.

In one aspect, the present invention provides for novel transglycosylation activity of *Flavobacterium meningosepticum* endoglycosidases, that being, Endo-F1, Endo-F2, Endo-F3 and mutants thereof, wherein the mutants have 95% homology thereto and exhibit the transglycosylation activity on fucosylated GlcNAc acceptors, wherein the endoglycosidases enable the transfer of an oligosaccharide (in the form of an activated sugar oxazoline) en bloc to a fucosylated GlcNAc-peptide acceptor to form a core-fucosylated glycopeptide. The transglycosylation activity of Endo-F1 (SEQ ID No: 1), Endo-F2 (SEQ ID No: 2), Endo-F3 (SEQ ID No: 3), Endo D and mutants thereof is specific for fucosylated GlcNAc acceptors, as transglycosylation activity on non-fucosylated GlcNAc acceptors is not detected under the same reaction conditions, such as in a buffer, pH 7 and at room temperature. Mutants preferably include site-specific mutations at active carboxyl residues that promotes product hydrolysis, including but not limited to, mutations at Asp-130 (SEQ ID NO: 10) of Endo-F1, mutations at Asp-124 of Endo-F2 (SEQ ID NOs: 4 and 5) mutations at Asp-126 of Endo-F3 (SEQ ID NOs: 6 and 7) and mutation at Asn-322 of Endo-D (SEQ ID NO: 8 and 9).

Sequences from Endo-F1, Endo-F2, and Endo-F3, as shown in FIG. 20, show remarkably enhanced transglycosylation efficiency due to the diminished or abrogated product hydrolytic activity. Mutations at "D" highlighted in FIG. 20 (D130 in Endo-F1, D124 in Endo-F2 and D126 in Endo-F3) in the respective sequences provide for active sites for such mutations and having the ability to use the activated glycan oxazolines as donor substrates for transglycosylation. For example, in Endo-F3, the following mutants, having at least 95% identity to Endo-F3, are effective for transglycosylation including but not limited to D126R, D126N, D126C, D126E, D126G, D126H, D126I, D126L, D126K, D126M, D126F, D126P, D126S, D126T, D126W, D126Y, and D126V.

In another aspect, the present invention provides efficient mutants of Endo-D, an endo-β-N-acetylglucosaminidase from *Streptococcus pneumonia*, for transglycosylation with glycan oxazolines. The Endo-D mutants, including but not limited to, N322A (SEQ ID NO: 8) and N322Q (SEQ ID NO: 9), show remarkably enhanced transglycosylation to either fucosylated or non-fucosylated GlcNAc acceptor.

In a further aspect, the present invention provides for a chemoenzymatic method for the preparation of a homogeneous fucosylated glycoprotein or glycopeptide, comprising:
(a) providing an acceptor selected from the group consisting of a fucosylated GlcNAc-protein and fucosylated GlcNAc-peptide; and
(b) reacting the acceptor with a donor substrate including an activated oligosaccharide moiety, in the presence of an endoglycosidase (ENGase) selected from Endo-F1, Endo-F2, Endo-F3, Endo-D or mutants thereof to transfer the activated oligosaccharide moiety to the acceptor and yield the homogeneous fucosylated glycoprotein or glycopeptide.

In a still further aspect, the present invention provides a method for preparing a core-fucosylated glycoprotein or glycopeptide having a predetermined oligosaccharide moiety, comprising:
(a) providing a core-fucosylated acceptor glycoprotein or glycopeptide comprising an asparagine-linked N-acetylglucosamine (GlcNAc) residue linked to a core fucose residue; and
(b) enzymatically reacting the core-fucosylated acceptor glycoprotein or glycopeptide with an activated oligosaccharide donor in the presence of at least one endoglycosidase selected from Endoglycosidase-F2 (SEQ ID NO: 2 or a sequence having 95% homology thereto), Endoglycosidase-F2 D124A (SEQ ID NO: 4) or D124Q (SEQ ID NO:5) mutant, Endoglycosidase-F3 (SEQ ID NO: 3 or a sequence having 95% homology thereof), Endoglycosidase-F3 D126A (SEQ ID NO: 6) or D126Q (SEQ ID NO: 7) mutant, and Endoglycosidase-D N322Q (SEQ ID NO: 9) mutant, wherein the activated oligosaccharide donor carries an oligosaccharide moiety comprising a predetermined number and type of sugar residues, such that, via enzymatic reaction, the oligosaccharide moiety is covalently linked to the acceptor glycoprotein or glycopeptide; thereby preparing the core-fucosylated glycoprotein or glycopeptide having the predetermined oligosaccharide moiety.

Notably, the wild type Endo-D amino acid sequence can also be defined without the signal peptide sequence included in the numbering and such a sequence is defined in SEQ ID NO: 15, wherein the mutation is N282A (SEQ ID NO: 16) or N282Q (SEQ ID NO: 17).

In yet another aspect, the present invention provides for an activated oligosaccharide moiety, such as glycosyl fluoride, glycosyl azide or an aryl glycoside, as a donor substrate for the synthesis of homogeneous core-fucosylated glycopeptides or glycoproteins. Preferably the activated oligosaccharide moiety is an oligosaccharide oxazoline.

In a further aspect, the present invention relates to a chemoenzymatic method for the preparation of a homogeneous fucosylated glycopeptide or glycoprotein, said method comprising:
(a) providing an acceptor selected from fucosylated glycopeptide or glycoprotein comprising a fucosylated GlcNAc containing peptide or protein; and
(b) reacting the acceptor with a donor substrate in the presence of an endoglycosidase (ENGase) selected from Endo-F1, Endo-F2, Endo-F1 Endo-F3, Endo-D and/or mutants thereof, wherein the donor substrate comprises a predetermined oligosaccharide component with a defined number and type of sugar residues and specific linkage types, thereby providing the homogeneous fucosylated glycopeptide or glycoprotein.

The fucosylated GlcNAc containing peptide or protein is preferably an alpha-1-6-fucosyl-GlcNAc-peptide or an alpha-1-6-fucosyl-GlcNAc-protein.

In another aspect, the invention relates to a method of fucosylated glycopeptide or glycoprotein remodeling with an oligosaccharide having a predetermined oligosaccharide component with a defined number and type of sugar residues and with specific linkage types, the method comprising:
(a) providing a fucosylated glycopeptide or glycoprotein substrate comprising at least two GlcNAc residues;
(b) treating the fucosylated glycopeptide or glycoprotein substrate with an endo-enzyme to hydrolyze the bond between the two GlcNAc residues positioned closest to the peptide thereby forming a fucosylated glycopeptide or glycoprotein substrate with a single GlcNAc-moiety; and (c) attaching the oligosaccharide to the single GlcNAc moiety in the presence of an endoglycosidase selected from the group consisting of Endo-F1, Endo-F2 and Endo-F3, thereby adding a predetermined the oligosaccharide component.

In a further aspect, the invention relates to a method of fucosylated glycopeptide or glycoprotein remodeling with an oligosaccharide having a predetermined oligosaccharide component with a defined number and type of sugar residues and with specific linkage types, the method comprising:

(a) providing a fucosylated glycopeptide or glycoprotein obtained from natural or recombined sources carrying heterogeneous N-glycans;

(b) treating the fucosylated glycopeptide or glycoprotein substrate with an endo-enzyme (a wild type endoglycosidase or a mutant endoglycosidase with efficient hydrolytic activity) to hydrolyze the bond between the two GlcNAc residues positioned closest to the peptide thereby forming a deglycosylated peptide or protein carrying the fucosylated GlcNAc disaccharide moiety at the original glycosylation site(s); and (c) attaching the pre-determined oligosaccharide to the GlcNAc residue in the fucosylated GlcNAc disaccharide moiety to reconstitute the natural α-1,4-glycosidic bond through the transglycosylation with an endoglycosidase selected from Endo-F1, Endo-F2, Endo-F3, Endo-D, and/or their glycosythase mutants, thereby adding a predetermined the oligosaccharide component.

Applicable oligosaccharide oxazolines include, but not limited to, high-mannose type, hybrid type, and complex type N-glycan, as well as their selectively modified derivatives. Preferably, di-, tri-, tetra-, penta-, hexyl-, hepta-, octyl-, nona-, deca-, or undeca-saccharide oxazolines are utilized as donor substrates for a highly efficient chemoenzymatic synthesis of homogeneous core-fucosylated glycopeptides or glycoproteins.

In yet another aspect, the present invention relates to a method of synthesis of a modified antibody or fragment thereof, the method comprising;

(a) using a naturally existing IgG antibody or a recombinant antibody or Fc domains carrying Fc N-glycans as precursors;

(b) Fc deglycosylating using an endoglycosidase such as Endo-F2, Endo-F3, or, Endo-S, Endo-D, or their hydrolytic activity-enhanced mutants to deglycosylate the Fc domain;

(c) providing an antibody comprising at least one fucosylated GlcNAc moiety to form a fucosylated GlcNAc-acceptor; wherein the fucosylated GlcNAc moiety is positioned on the Fc region of the antibody; and (d) transglycosylating the fucosylated GlcNAc moiety in the antibody with an oligosaccharide oxazoline having a predetermined number of sugar residues under the catalysis of an enzyme selected from the group consisting of Endo-F1, Endo-F2, Endo-F3, Endo-D or their mutants thereof to form the modified antibody with the predetermined number of saccharides.

In a still further aspect, the invention relates to a method of synthesizing homogeneous fucosylated glycopeptide or glycoprotein, the method comprising:

(a) providing a heterogeneous fucosylated glycopeptide or glycoprotein comprising different high mannose type N-glycans, wherein the heterogeneous fucosylated glycopeptide or glycoprotein is from a natural source or produced from a wild type or engineered yeast system;

(b) removing the different high mannose type N-glycans by an enzyme selected from the group consisting of Endo-H, Endo-S and Endo-A to form a fucosylated GlcNAc-containing peptide or protein;

(c) providing a sugar containing oxazolines with a desired oligosaccharide component comprising a defined number and type of sugar residues in the chain; and (d) enzymatically transglycosylating, with an endoglycosidase selected from the group consisting of Endo-F1, Endo-F2, Endo-F3, Endo-D and mutants thereof, the fucosylated GlcNAc-containing peptide or protein with the sugar containing oxazoline thereby forming a homogeneous fucosylated glycopeptide or glycoprotein having an extension of desired number of sugar residues.

In another aspect, the present invention relates to a method of synthesis of a modified antibody or fragment thereof, the method comprising;

(a) providing an antibody comprising at least one fucosylated GlcNAc moiety to form a fucosylated GlcNAc-peptide acceptor; wherein the fucosylated GlcNAc moiety is positioned on the Fc region of the antibody; and (b) transglycosylating an oligosaccharide oxazoline having a predetermined number of saccharides and the fucosylated GlcNAc-peptide acceptor under the catalysis of an enzyme selected from the group consisting of Endo-F1, Endo-F2, Endo-F3, Endo-D or their mutants thereof to form the modified antibody with the predetermined number of saccharides.

It is envisioned that the oligosaccharide oxazoline having a predetermined oligosaccharide component with a defined number and type of sugar residues may further comprises an additional moiety or tag including, a therapeutic agent or drug such as for treating cancer, HIV or other viruses, substances that activates receptors on the cell plasma membrane, agents that affects intracellular chemistry, agents that affects cellular physics, genes, gene analogs, RNA, RNA analogs, DNA, DNA analogs, amino acid sequences of surface receptors such as CCR5 or CD4, antigenic structure having affinity for a specific antibody; amino acid sequences of receptor ligands such as gp120, gp41 or gp160, receptor antagonists, receptor blockers, enzymes, enzyme substrates, enzyme inhibitors, enzyme modulators, therapeutic proteins, protein analogs, metabolites, metabolite analogs, oligonucleotides, oligonucleotide analogs, antigens, antigen analogs, antibodies or fragments thereof, antibody analogs, an antibody different from the modified antibody which is reactive to another receptor bacteria, viruses, inorganic ions, metal ions, metal clusters, polymers, fluorescent compounds and any combinations thereof.

As such, the present invention further provides a delivery device for delivering a drug having biological activity to treat a condition, the delivery device comprising: a remodeled fucosylated glycoprotein or glycopeptides having a predetermined sugar chain and a therapeutic agent or drug attached to the terminal sugar residue.

The present invention envisions modifying monoclonal antibodies related to HIV including, but not limited to 17b, 48d, A32, C11, 2G12, F240, IgG1b12, 19e, X5, TNX-355 and F91, all of which are commercially available. Further antibodies related to cancer or other diseases may also be remodeled for individual fit to certain receptors thereby increasing biological activity, the monoclonal antibodies may include, but are not limited to, cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, I-131 tositumomab, efalizumab, bevacizumab, panitumumab, pertuzumab, natalizumab, etanercept, IGN101 (Aphton), voloximab (Biogen Idec and PDL BioPharm), Anti-CD80 mAb (Biogen Idec), Anti-CD23 mAb (Biogen Idel), CAT-3888 (Cambridge Antibody Technology), CDP-791 (Imclone), eraptuzumab (Immunomedics), MDX-010 (Medarex and BMS), MDX-060 (Medarex), MDX-070 (Medarex), matuzumab (Merck), CP-675, 206 (Pfizer), CAL (Roche), SGN-30 (Seattle Genetics), zanolimumab (Serono and Genmab), adecatumumab (Sereno), oregovomab (United Therapeutics), nimotuzumab (YM Bioscience), ABT-874 (Abbott Laboratories), denosumab (Amgen), AM 108 (Amgen), AMG 714 (Amgen), fontolizumab (Biogen Idec and PDL BioPharm), daclizumab (Biogent Idec and PDL BioPharm), golimumab (Centocor and Schering-Plough), CNTO 1275 (Centocor), ocrelizumab (Genetech and Roche), HuMax-CD20 (Genmab), belimumab (HGS and GSK), epratuzumab (Immunomedics), MLN1202 (Millennium Pharmaceuticals), visilizumab (PDL BioPharm), tocilizumab (Roche), ocrerlizumab (Roche), certolizumab pegol (UCB, formerly Celltech), eculizumab (Alexion Pharmaceuticals), pexelizumab (Alexion Pharmaceuticals and Procter & Gamble), abciximab (Centocor), ranibizimumab (Genetech), mepolizumab (GSK), TNX-355 (Tanox), or MYO-029 (Wyeth).

A still further aspect of the invention relates to a method of remodeling an antibody which initially includes a heterogeneous sugar chain, including polyclonal and monoclonal antibodies, the method comprising:
(a) removing the heterogeneous sugar chain from the antibody with an endoglycosidase to leave a single fucosylated-GlcNAc moiety attached to an original glycosylation site; and
(b) transferring a core oligosaccharide with at least one tag to the fucosylated-GlcNAc moiety by an endoglycosidase catalyzed transglycosylation to yield a tagged antibody, wherein the endoglycosidase is selected from the group consisting of Endo-F1, Endo-F2, Endo-F3, Endo-D and mutants thereof.

The tag moiety may include, but is not limited to, antigens, therapeutic drugs such as for cancer or HIV, toxins, fluorescent probes, biotin, PEG species, lipids, or nucleotides.

In another aspect, the present invention provides for a method of treatment using a remodeled antibody having a desired glycosylation state in an amount sufficient to modulate biological activity in the treated subject.

Other aspects, features and embodiments of the invention will be more fully apparent from the ensuing disclosure and appended claims.

BRIEF DESCRIPTION OF THE FIGURES

FIG. 20 shows the sequence and alignment of the three endo-beta-N-acetylglucosaminidases (Endo-F1 (SEQ ID NO: 1), Endo-F2 (SEQ ID NO: 2), and Endo-F3 (SEQ ID NO: 3) from *Flavobacterium meningosepticum* (alternative name; *Elizabethkingia meningosepticum*) [85].
FIG. 21 shows the sequence of the endo-beta-N-acetylglucosaminidase from *Streptococcus pneumonia* (Endo-D) (SEQ ID NO: 11) [86].

DETAILED DESCRIPTION OF THE INVENTION

Figure 1:
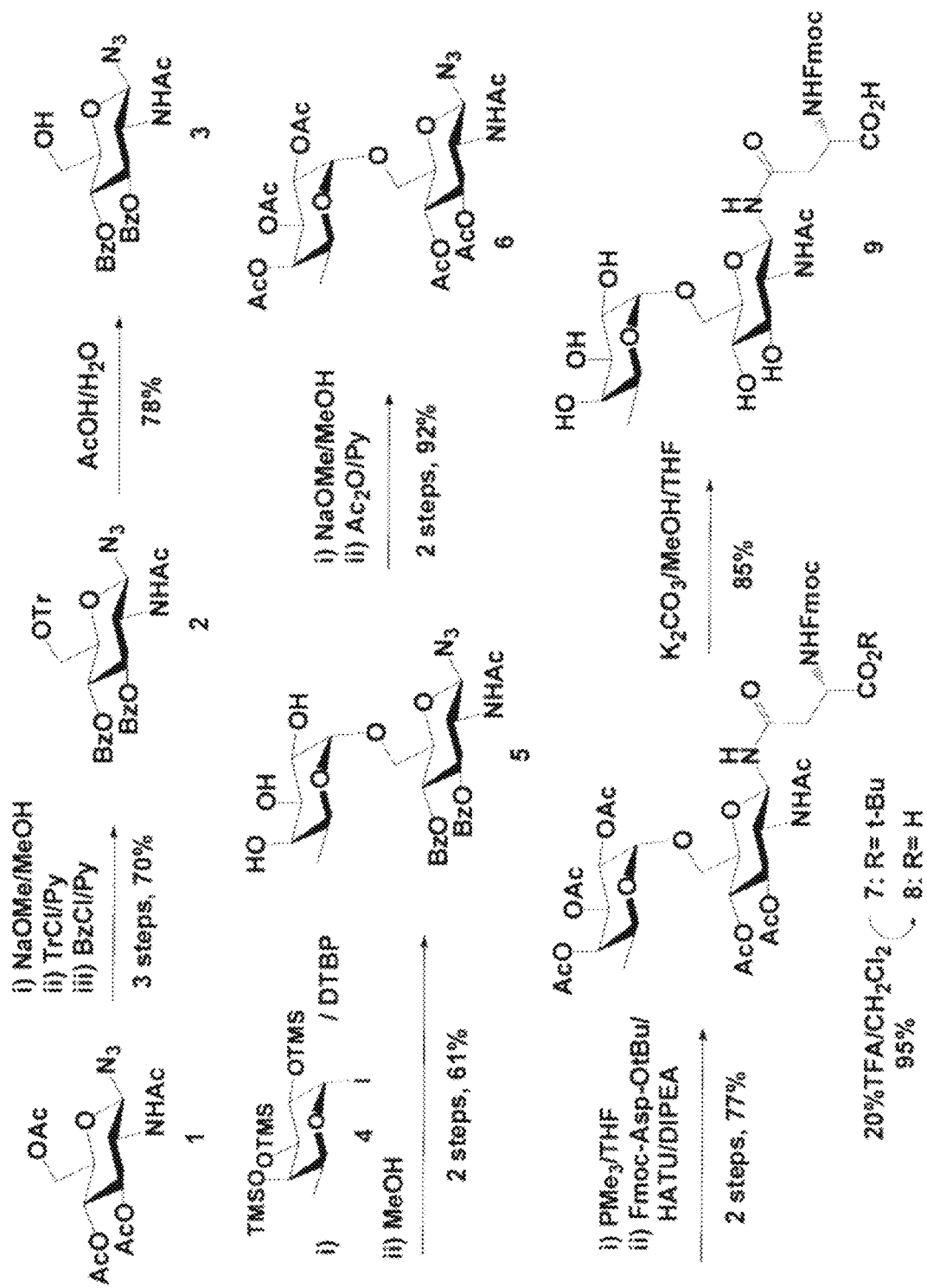
FIG. 1 shows the synthesis of Fmoc-Asn(Fucα1,6GlcNAc)-OH (9).

The practice of the present invention will employ, unless otherwise indicated, conventional techniques of immunology, molecular biology, microbiology, cell biology and recombinant DNA, which are within the skill of the art. See, e.g., Sambrook, et al. MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

As used in the specification herein, "a" or "an" may mean one or more. As used herein in the claim(s), when used in conjunction with the word "comprising", the words "a" or "an" may mean one or more than one. As used herein "another" may mean at least a second or more.

As used herein, "biological activity" refers to pharmacodynamic and pharmacokinetic properties including, for example, molecular affinity or resultant biochemical or physiological effect, receptor affinity or resultant biochemical or physiological effect, non-receptor affinity or biochemical or physiological effect, efficacy, bioavailability, absorption, distribution, metabolism, or elimination.

As used herein, "sugar" refers to an oxidized or unoxidized carbohydrate-containing molecule, including, but not limited to, a monosaccharide, disaccharide, trisaccharide, oligosaccharide, or polysaccharide, including, for example, N-acetylglucosamine, mannose, galactose, N-acetylneuraminic acid (sialic acid), glucose, fructose, fucose, sorbose, rhamnose, mannoheptulose, N-acetylgalactosamine, dihydroxyacetone, xylose, xylulose, arabinose, glyceraldehyde, sucrose, lactose, maltose, trehalose, cellobiose or any combination thereof of the L- or D-isomer. Sugar further refers to, such molecules produced naturally, recombinantly, synthetically, and/or semi-synthetically.

As used herein, "homogenous" refers to core-fucosylated glycopeptides or glycoproteins wherein the oligosaccharide component comprises at least 75%, more preferably at least 90%, and most preferably at least 95% of the same number and types of sugar residues.

As used herein, "homology" refers to amino acid sequence having substantial identity or similarity between two polypeptides and having at least 90%, and more preferably at least 95% similarity to a reference polypeptide. For polypeptides, the length of comparison to obtain the above-described percent homologies between sequences will generally be at least 25 amino acids, alternatively at least 50 amino acids, more likely at least 100 amino acids, and most likely 200 amino acids or more. Substantially identity or homologous polypeptides include additions, truncations, internal deletions or insertions, conservative and non-conservative substitutions, or other modifications located at positions of the amino acid sequence which do not destroy the function of the endoglycosidase. Those of skill in the art will recognize the numerous amino acids that can be modified or substituted with other chemically similar residues without substantially altering activity.

As used herein, "modulates" refers to an increase or decrease in "biological activity", as defined above, when comparing to a glycosylation-engineered antibody of the present invention to a non-glycosylation-engineered antibody.

As used herein, "immunoglobulin molecule" or "antibodies," refers to molecules that contain an antigen binding site which specifically binds an antigen or an Fc region that binds to cell receptors. Structurally, the simplest naturally occurring antibody (e.g., IgG) comprises four polypeptide chains, two heavy (H) chains and two light (L) chains inter-connected by disulfide bonds. The natural immunoglobulins represent a large family of molecules that include several types of molecules, such as IgD, IgG, IgA, IgM and IgE. The term also encompasses hybrid antibodies, or altered antibodies, and fragments thereof, including but not limited to Fab fragment(s) and Fc fragment(s).

Antibodies can be fragmented using conventional techniques as described herein and the fragments screened for utility in the same manner as described for whole antibodies. A Fab fragment of an immunoglobulin molecule is a multimeric protein consisting of the portion of an immunoglobulin molecule containing the immunologically active portions of an immunoglobulin heavy chain and an immunoglobulin light chain covalently coupled together and capable of specifically combining with an antigen. Fab and Fc fragments can be prepared by proteolytic digestion of substantially intact immunoglobulin molecules with papain using methods that are well known in the art. However, a Fab or Fc fragment may also be prepared by expressing in a suitable host cell the desired portions of immunoglobulin heavy chain and immunoglobulin light chain using methods known in the art.

As used herein, with respect to antibodies, "substantially pure" means separated from those contaminants that accompany it in its natural state or those contaminants generated or used in the process of the obtaining the antibody. This term further includes the desired product having a single glycosylation state, whether or not this state includes glycosylation at a single site or multiple sites. Typically, the antibody is substantially pure when it constitutes at least 60%, by weight, of the antibody in the preparation. For example, the antibody in the preparation is at least about 75%, in certain embodiments at least about 80%, in certain embodiments at about 85%, in certain embodiments at least about 90%, in certain embodiments at least about 95%, and most preferably at least about 99%, by weight, of the desired antibody. A substantially pure antibody includes a naturally, recombinantly, or synthetically produced antibody.

As used herein, "therapeutically effective amount" refers to an amount that results in an improvement or remediation of the symptoms of the disease or condition.

Antigens useful for attachment as a tag to a modified fucosylated glycoprotein of the present invention and more preferably an antibody or fragment thereof may be a foreign antigen, an endogenous antigen, fragments thereof, or variants having the same functional activity.

As used herein, "endogenous antigen" refers to a protein or part thereof that is naturally present in the recipient animal cell or tissue, such as a cellular protein, an immunoregulatory agent, or a therapeutic agent.

As used herein, "foreign antigen" refers to a protein or fragment thereof, which is foreign to the recipient animal cell or tissue including, but not limited to, a viral protein, a parasite protein, an immunoregulatory agent, or a therapeutic agent.

The foreign antigen may be a protein, an antigenic fragment or antigenic fragments thereof that originate from viral and parasitic pathogens.

Alternatively, the foreign antigen may be encoded by a synthetic gene and may be constructed using conventional recombinant DNA methods; the synthetic gene may express antigens or parts thereof that originate from viral and parasitic pathogens. These pathogens can be infectious in humans, domestic animals or wild animal hosts.

The foreign antigen can be any molecule that is expressed by any viral or parasitic pathogen prior to or during entry into, colonization of, or replication in their animal host.

The viral pathogens, from which the viral antigens are derived include, but are not limited to, Orthomyxoviruses, such as influenza virus (Taxonomy ID: 59771); Retroviruses, such as RSV, HTLV-1 (Taxonomy ID: 39015) and HTLV-II (Taxonomy ID: 11909); Herpes viruses, such as EBV (Taxonomy ID: 10295), CMV (Taxonomy ID: 10358) or herpes simplex virus (ATCC #: VR-1487); Lentiviruses, such as HIV-1 (Taxonomy ID: 12721) and HIV-2 Taxonomy ID: 11709); Rhabdoviruses, such as rabies; Picornoviruses, such as Poliovirus (Taxonomy ID: 12080); Poxviruses, such as vaccinia Taxonomy ID: 10245); Rotavirus Taxonomy ID: 10912); and Parvoviruses, such as adeno-associated virus 1 (Taxonomy ID: 85106).

Examples of viral antigens include, but are not limited to, the human immunodeficiency virus antigens Nef (National Institute of Allergy and Infectious Disease HIV Repository Cat. #183; GenBank accession # AF238278), Gag, Env (National Institute of Allergy and Infectious Disease HIV Repository Cat. #2433; GenBank accession # U39362), Tat (National Institute of Allergy and Infectious Disease HIV Repository Cat. #827; GenBank accession # M13137), Rev (National Institute of Allergy and Infectious Disease HIV Repository Cat. #2088; GenBank accession # L14572), Pol (National Institute of Allergy and Infectious Disease HIV Repository Cat. #238; GenBank accession # AJ237568) and T cell and B cell epitopes of gp120; the hepatitis B surface antigen (GenBank accession # AF043578); rotavirus antigens, such as VP4 (GenBank accession # AJ293721) and VP7 (GenBank accession # AY003871); influenza virus antigens, such as hemagglutinin (GenBank accession # AJ404627); nucleoprotein (GenBank accession # AJ289872); and herpes simplex virus antigens, such as thymidine kinase (GenBank accession # AB047378).

The bacterial pathogens, from which the bacterial antigens are derived, include but are not limited to, *Mycobacterium* spp., *Helicobacter pylori, Salmonella* spp., *Shigella* spp., *E. coli, Rickettsia* spp., *Listeria* spp., *Legionella pneumoniae, Pseudomonas* spp., *Vibrio* spp., and *Borellia burgdorferi*.

Examples of protective antigens of bacterial pathogens include the somatic antigens of enterotoxigenic *E. coli*, such as the CFA/I fimbrial antigen and the nontoxic B-subunit of the heat-labile toxin; pertactin of *Bordetella pertussis*, adenylate cyclase-hemolysin of *B. pertussis*, fragment C of tetanus toxin of *Clostridium tetani*, OspA of *Borellia burgdorferi*, protective paracrystalline-surface-layer proteins of *Rickettsia prowazekii* and *Rickettsia typhi*, the listeriolysin (also known as "Llo" and "Hly") and/or the superoxide dismutase (also know as "SOD" and "p60") of *Listeria monocytogenes*; the urease of *Helicobacter pylori*, and the receptor-binding domain of lethal toxin and/or the protective antigen of *Bacillus* anthrax.

Example of antigens from biological weapons or pathogens include, but are not limited to, smallpox, anthrax, tularemia, plague, *listeria*, brucellosis, hepatitis, vaccinia, mycobacteria, coxsackievirus, tuberculosis, malaria, erhlichosis and bacterial meningitis.

The parasitic pathogens, from which the parasitic antigens are derived, include but are not limited to, *Plasmodium* spp., such as *Plasmodium falciparum* (ATCC #: 30145); *Trypanosome* spp., such as *Trypanosoma cruzi* (ATCC #: 50797); *Giardia* spp., such as *Giardia* intestinalis (ATCC #: 30888D); *Boophilus* spp.; *Babesia* spp., such as *Babesia microti* (ATCC #: 30221); *Entamoeba* spp., such as *Entamoeba histolytica* (ATCC #: 30015); *Eimeria* spp., such as *Eimeria maxima* (ATCC #40357); *Leishmania* spp., (Taxonomy ID: 38568); *Schistosome* spp., such as *Schistosoma mansoni* (GenBank accession # AZ301495); *Brugia* spp., such as *Brugia malayi* (GenBank accession # BE352806); *Fascida* spp., such as *Fasciola hepatica* (GenBank accession # AF286903); *Dirofilaria* spp., such as *Dirofilaria immitis* (GenBank accession # AF008300); *Wuchereria* spp., such as *Wuchereria bancrofti* (GenBank accession # AF250996); and *Onchocerca* spp; such as *Onchocerca volvulus* (GenBank accession # BE588251).

Examples of parasite antigens include, but are not limited to, the pre-erythrocytic stage antigens of *Plasmodium* spp. such as the circumsporozoite antigen of *P. falciparum* (GenBank accession # M22982) *P. vivax* (GenBank accession # M20670); the liver stage antigens of *Plasmodium* spp, such as the liver stage antigen 1 (as referred to as LSA-1; GenBank accession # AF086802); the merozoite stage antigens of *Plasmodium* spp; such as the merozoite surface antigen-1 (also referred to as MSA-1 or MSP-1; GenBank accession # AF199410); the surface antigens of *Entamoeba histolytica*, such as the galactose specific lectin (GenBank accession # M59850) or the serine rich *Entamoeba histolytica* protein; the surface proteins of *Leishmania* spp, such as 63 kDa glycoprotein (gp63) of *Leishmania major* (GenBank accession # Y00647 or the 46 kDa glycoprotein (gp46) of *Leishmania major*; paramyosin of *Brugia malayi* (GenBank accession # U77590; the triose-phosphate isomerase of *Schistosoma mansoni* (GenBank accession # WO6781; the secreted globin-like protein of *Trichostrongylus colubriformis* (GenBank accession # M63263; the glutathione-S-transferases of *Fasciola hepatica* (GenBank accession # M77682; *Schistosoma bovis* (GenBank accession # M77682); *S. japonicum* (GenBank accession # U58012; and KLH of *Schistosoma bovis* and *S. japonicum* (Bashir, et al., supra).

Examples of tumor specific antigens include prostate specific antigen (PSA), TAG-72 and CEA; human tyrosinase (GenBank accession # M27160); tyrosinase-related protein (also referred to as TRP; GenBank accession # AJ132933); and tumor-specific peptide antigens.

Examples of transplant antigens include the CD3 molecule on T cells and histocompatibility antigens such as HLA A, HLA B, HLA C, HLA DR and HLA.

Examples of autoimmune antigens include IAS β chain, which is useful in therapeutic vaccines against autoimmune encephalomyelitis (GenBank accession # D88762); glatamic acid decarboxylase, which is useful in therapeutic vaccines against insulin-dependent type 1 diabetes (GenBank accession # NM013445); thyrotropin receptor (TSHr), which is useful in therapeutic vaccines against Grave's disease (GenBank accession # NM000369) and tyrosinase-related protein 1, which is useful in therapeutic vaccines against vitiligo (GenBank accession # NM000550).

HIV drugs that may be used in the construction of the tagged antibodies or fragments thereof include, but are not limited to antiviral agents such as nucleoside RT inhibitors, CCR5 inhibitors/antagonists, viral entry inhibitors and their functional analogs. Specifically, an antiviral agent may nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies; and viral entry inhibitors, such as Fuzeon (T-20) (enfuvirtide), NB-2, NB-64, T-649, T-1249, SCH-C, SCH-D, PRO 140, TAK 779, TAK-220, RANTES analogs, AK602, UK-427, 857; and functional analogs or equivalents thereof.

It is envisioned that many different fucosylated polypeptide and fucosylated glycoproteins can be modified according to the methods of the present invention or used as a therapeutic agent for conjugation to a terminal sugar including but not limited to, adrenocorticotropic hormone (ACTH); adrenocorticotropic hormone derivatives (e.g., ebiratide); angiotensin; angiotensin II; asparaginase; atrial natriuretic peptides; atrial sodium diuretic peptides; bacitracin; beta-endorphins; blood coagulation factors VII, VIII and IX; blood thymic factor (FTS); blood thymic factor derivatives; bombesin; bone morphogenic factor (BMP); bone morphogenic protein; bradykinin; caerulein; calcitonin gene related polypeptide (CGRP); calcitonins; CCK-8; cell growth factors (e.g., EGF; TGF-alpha; TGF-beta; PDGF; acidic FGF; basic FGF); cerulein; chemokines; cholecystokinin; cholecystokinin-8; cholecystokinin-pancreozymin (CCK-PZ); colistin; colony-stimulating factors (e.g. CSF; GCSF; GMCSF; MCSF); corticotropin-releasing factor (CRF); cytokines; desmopressin; dinorphin; dipeptide; dismutase; dynorphin; eledoisin; endorphins; endothelin; endothelin-antagonistic peptides; endotherins; enkephalins; enkephalin derivatives; epidermal growth factor (EGF); erythropoietin (EPO); follicle-stimulating hormone (FSH); gallanin; gastric inhibitory polypeptide; gastrin-releasing polypeptide (GRP); gastrins; G-CSF; glucagon; glutathione peroxidase; glutathio-peroxidase; gonadotropins (e.g., human chorionic gonadotrophin and .alpha. and .beta. subunits thereof); gramicidin; gramicidines; growth factor (EGF); growth hormone-releasing factor (GRF); growth hormones; hormone releasing hormone (LHRH); human artrial natriuretic polypeptide (h-ANP); human placental lactogen; insulin; insulin-like growth factors (IGF-I; IGF-II); interferon; interferons (e.g., alpha- beta- and gamma-interferons); interleukins (e.g. 1; 2; 3; 4; 5; 6; 7; 8; 9; 10; 11 and 12); intestinal polypeptide (VIP); kallikrein; kyotorphin; luliberin; luteinizing hormone (LH); luteinizing hormone-releasing hormone (LH-RH); lysozyme chloride; melanocyte-stimulating hormone (MSH); melanophore stimulating hormone; mellitin; motilin; muramyl; muramyldipeptide; nerve growth factor (NGF); nerve nutrition factors (e.g. NT-3; NT-4; CNTF; GDNF; BDNF); neuropeptide Y; neurotensin; oxytocin; pancreastatin; pancreatic polypeptide; pancreozymin; parathyroid hormone (PTH); pentagastrin; polypeptide YY; pituitary adenyl cyclase-activating polypeptides (PACAPs); platelet-derived growth factor; polymixin B; prolactin; protein synthesis stimulating polypeptide; PTH-related protein; relaxin; renin; secretin; serum thymic factor; somatomedins; somatostatins derivatives; superoxide dismutase; taftsin; tetragastrin; thrombopoietin (TPO); thymic humoral factor (THF); thymopoietin; thymosin; thymostimulin; thyroid hormone releasing hormone; thyroid-stimulating hormone (TSH); thyrotropin releasing hormone TRH); trypsin; tuftsin; tumor growth factor (TGF-alpha); tumor necrosis factor (TNF); tyrocidin; urogastrone; urokinase; vasoactive intestinal polypeptide; and vasopressin.

Fucosylated glycoproteins are an important class of biomolecules that play crucial roles in many biological events such as cell adhesion, tumor metastasis, pathogen infection, and immune response. As indicated previously herein, a major problem in structural and functional studies of fucosylated glycoproteins is their structural microheterogeneity. Natural and recombinant fucosylated glycoproteins are typically produced as a mixture of glycoforms that differ only in the structure of the pendent oligosaccharides.

Referring now, more specifically, to the invention and various aspects and embodiments thereof, the present invention provides a chemoenzymatic method for the preparation of homogeneous fucosylated glycoproteins, including both natural and tailor-made fucosylated glycoproteins. The present invention is based on the fact that synthetic sugar oxazolines can serve as efficient donor substrates of some endoglycosidases (ENGases) for transferring to a fucosylated-GlcNAc-peptide and fucosylated-GlcNAc-protein acceptor to form a new fucosylated glycopeptide and fucosylated glycoprotein in a stereo- and regio-specific manner, and in a high-yield.

Generally, the method includes two key steps: a) the preparation of the acceptor, a fucosylated GlcNAc-protein or a fucosylated GlcNAc-peptide and b) endoglycosidase (ENGase)-catalyzed transfer of an oligosaccharide moiety from a pre-assembled donor substrate, including but not limited to a synthetic oligosaccharide oxazoline or other activated donors including a modified oxazoline to the fucosylated GlcNAc-protein or fucosylated GlcNAc-peptide to form the desired fucosylated glycoprotein or fucosylated glycopeptides.

Figure 17:
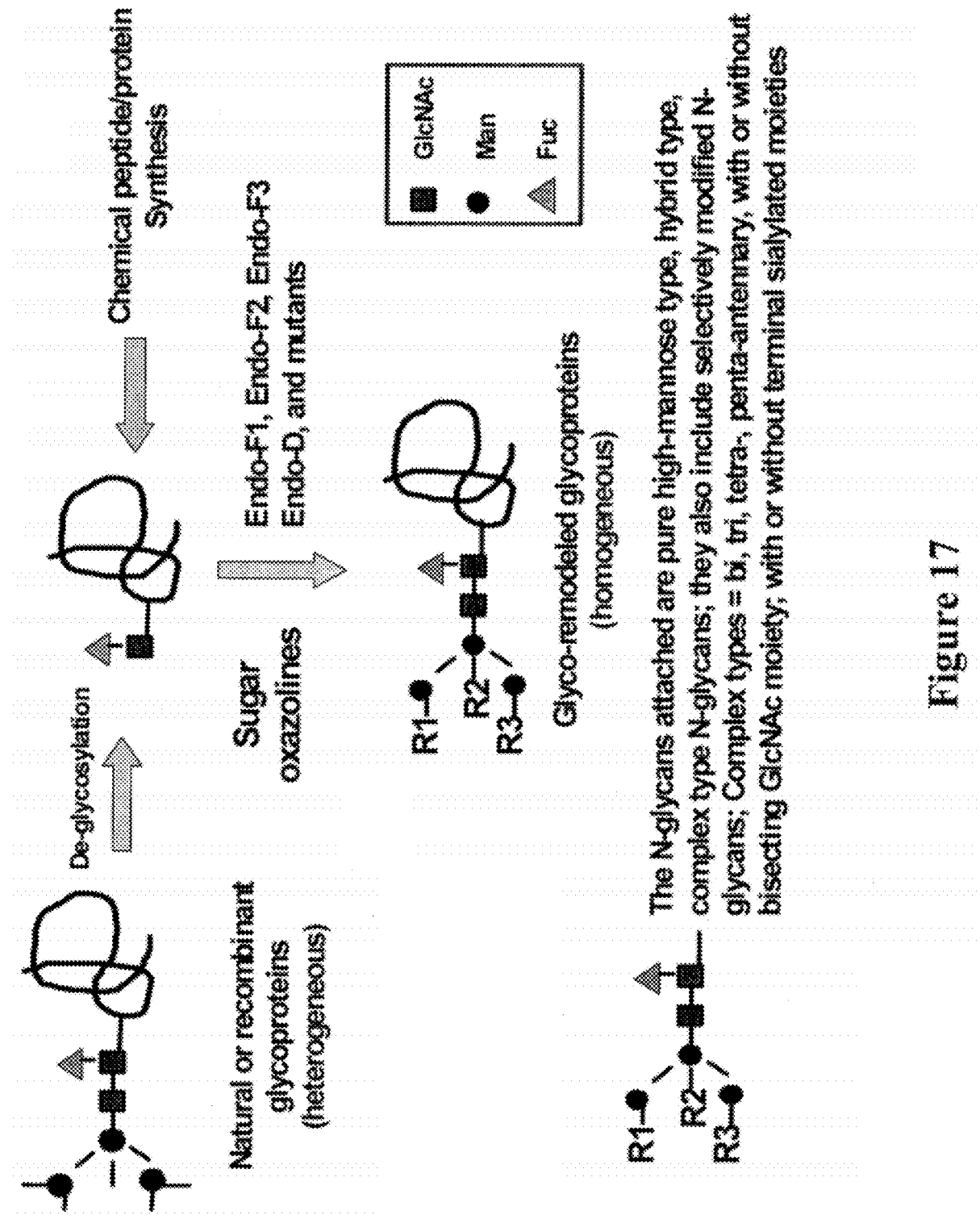
FIG. 17 shows the synthesis or remodeling of core-fucosylated glycopeptides and glycoproteins.

Thus, the invention provides a general method for glycoprotein remodeling comprising the treatment of the natural or recombinant fucosylated glycoproteins with an endoenzyme (Endo-A, Endo-H, Endo-M, etc., depending on the nature of the N-glycans to be removed and the substrate specificity of the respective endo-enzymes), which will hydrolyze the bond between the two GlcNAc residues in the N-acetylchitobiose core of the N-glycans to afford the GlcNAc-protein, with the inner GlcNAc residue being still attached to the original glycosylation sites, as shown in the simplified illustration of FIG. 17. Notably, the fucosylated core is shown wherein the fucose moiety is attached to a GlcNAc moiety positioned adjacent to the protein moiety. Then a prepared N-glycan with the desired sugar component (defined monosaccharide residues and linkage types) will be attached to the original glycosylation site(s) by the high-yield enzymatic oligosaccharide transfer from synthetic sugar oxazolines or other activated donor substrates (glycosyl fluoride and aryl glycoside may be used) by an ENGase selected from Endo-F1, Endo-F2, Endo-F3, Endo-D or active mutants thereof. The steps can be easily understood as set forth in FIG. 17.

In this method, the fucosylated GlcNAc-protein or fucosylated GlcNAc-peptide can be prepared by a process such as chemical total protein synthesis, native chemical ligation, expressed protein ligation, etc. A multiplicity of N-glycans can be attached to the fucosylated GlcNAc-protein or fucosylated GlcNAc-peptide in such method A further aspect of the invention relates to a method of remodeling an antibody including a heterogeneous sugar chain, including:
  (a) removing the heterogeneous sugar chain from the antibody with an endoglycosidase to leave a single fucosylated GlcNAc moiety attached to an original glycosylation site; and
  (b) transferring a core oligosaccharide to said fucosylated GlcNAc moiety by ENGase-catalyzed transglycosylation to yield a remodeled antibody.

Figure 16:
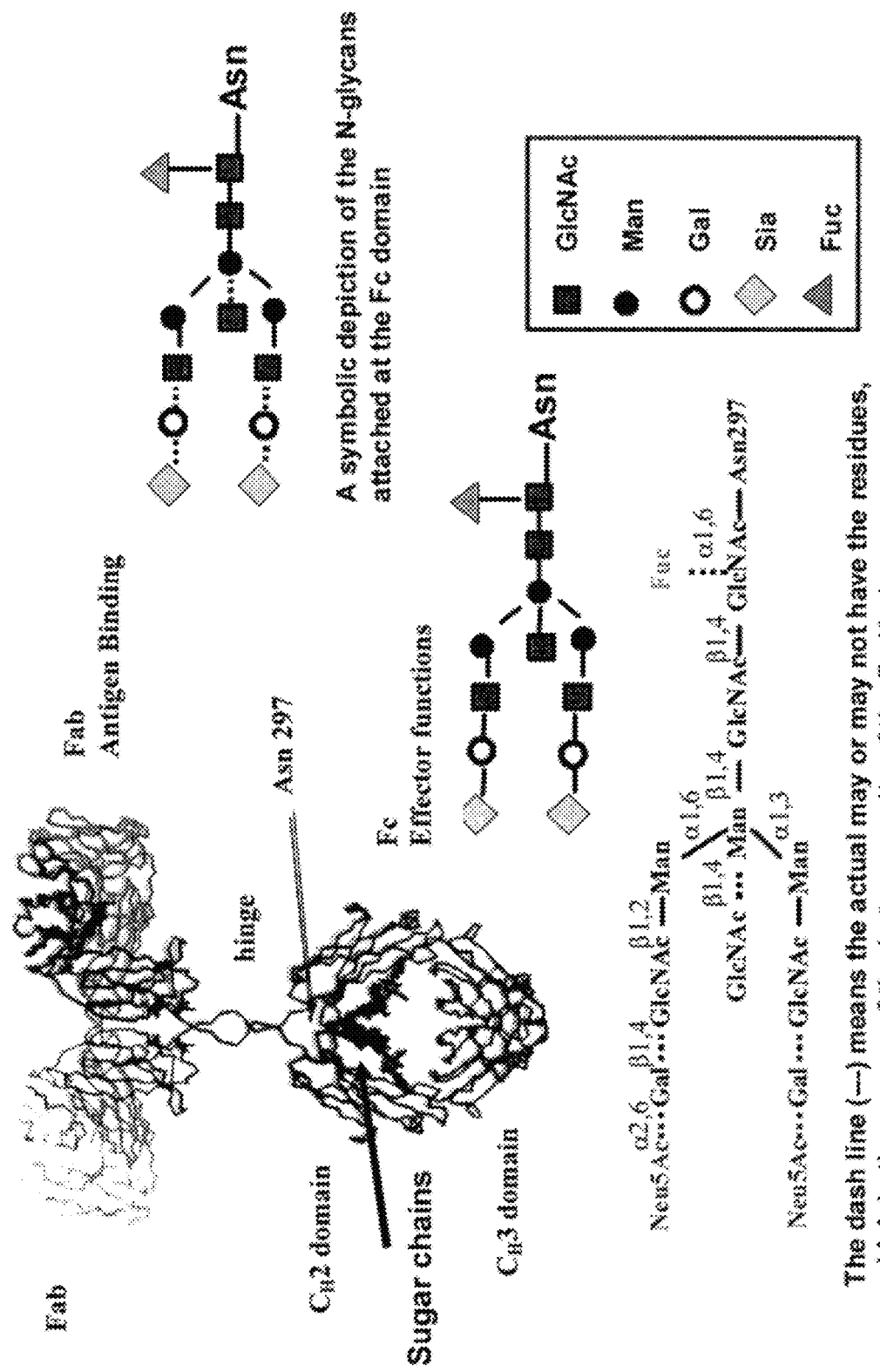
FIG. 16 shows the structure of a typical monoclonal antibody and the Fc N-glycans.
Figure 18:
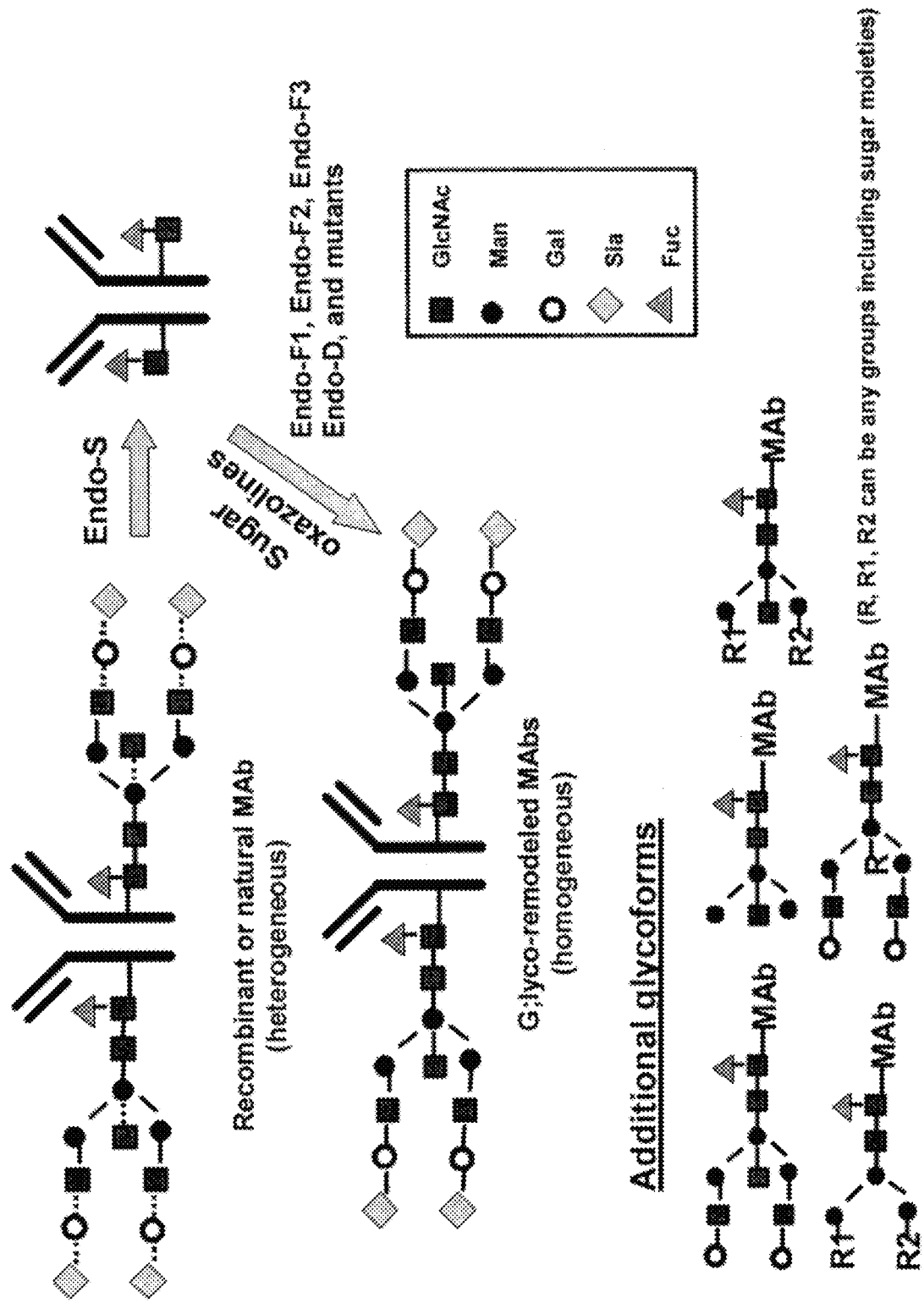
FIG. 18 shows the glycosylation remodeling of monoclonal antibodies.
Figure 19:
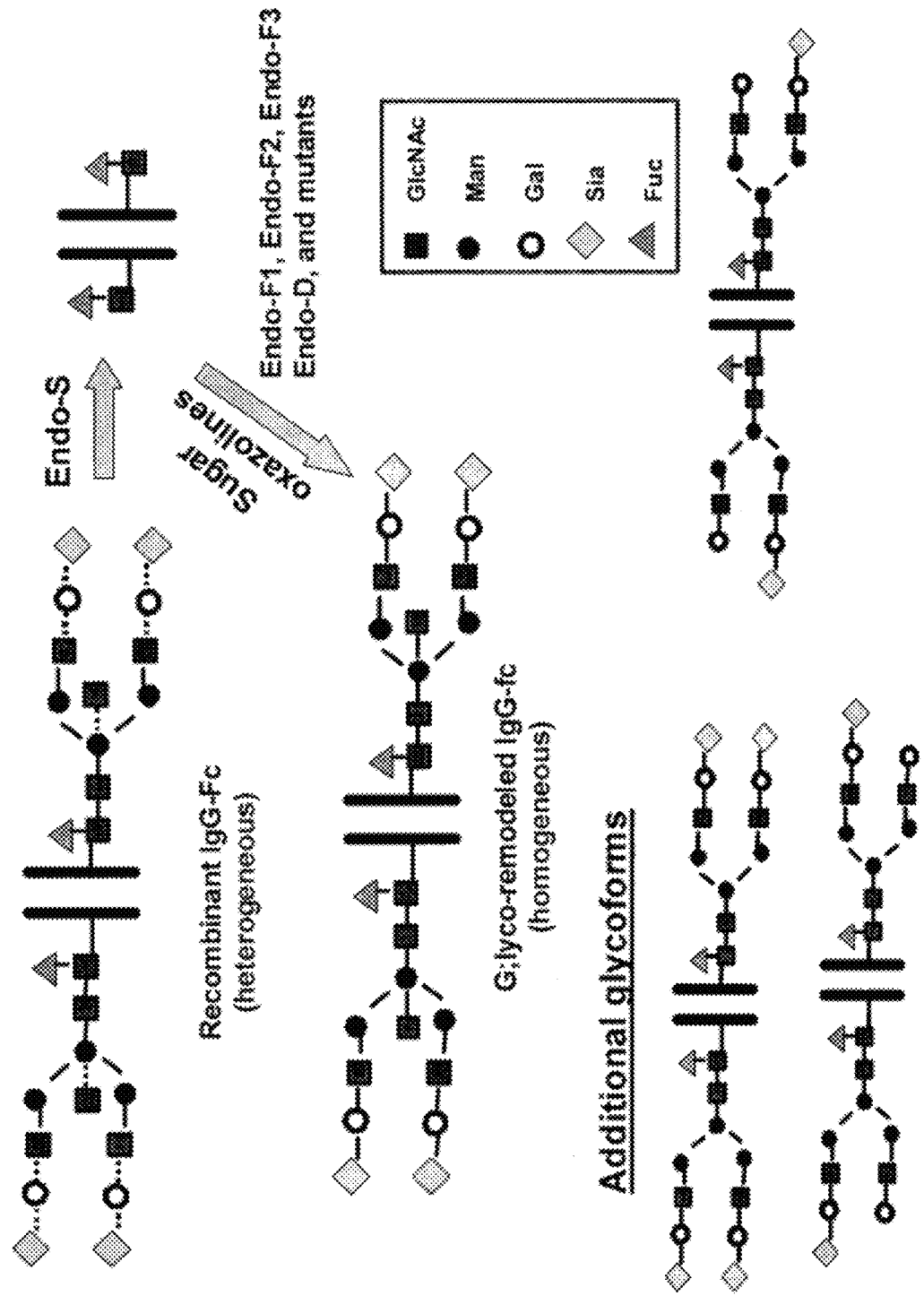
FIG. 19 shows the glycosylation remodeling of a recombinant IgG-Fc.

FIGS. 16, 18 and 19 provide simplified schemes for remodeling of a full antibody have both Fab and Fc regions available or just the Fc region.

Such method may further include incorporating a functional component into the tagged antibody by selective ligation reaction to yield a functionalized antibody. The antibody may for example be functionalized for drug delivery, targeting a specific antigen, etc. The antibody may be functionalized with a functional component selected from among antigens, toxins, radioactive species, photoactive species, and polyethylene glycols. In a specific embodiment, the functionalized antibody is functionalized with alpha-Gal. The antibody itself may be of any suitable type, and may for example be an immunoglobulin, an antibody fragment, or other antibody species.

The endoglycosidase employed in such method is selected from Endo-F1, Endo-F2, Endo-F3, Endo-D and mutants thereof. The remodeled glycoproteins or glycopeptides, such as antibodies can be subjected to any further structural modifications that are necessary or desired, including, without limitation, glycosyl transfer, and selective ligation (e.g., click chemistry, Staudinger reaction, etc.) to introduce the additional functional groups or tags. The functional groups can be of any suitable type, including, without limitation, toxins, special antigens (such as alpha-Gal), radioactive species, photoactive species, PEGs, etc. The glycoprotein can be catalytically reacted in a "click chemistry" cycloaddition reaction of the azide functionality of the glycoprotein with an alkyne bearing the functional moiety of interest. The azido and alkyne functional groups can be switched in the respective ligation components, and the glycoprotein can be functionalized with an alkynyl functionality and reacted with an azide-functionalized compound including the moiety of interest. It will also be appreciated that other ligation pairs can be devised for the click chemistry reaction.

The present invention provides a novel transglycosylation activity of *Flavobacterium meningosepticum* endoglycosidases, that being Endo-F1, Endo-F2 and Endo-F3, that enables transfer of oligosaccharide en bloc to fucosylated GlcNAc-peptide acceptor to form core-fucosylated glycopeptides. The transglycosylation activity of Endo-F1, Endo-F2 and Endo-F3 is specific for fucosylated GlcNAc acceptor, as transglycosylation activity on non-fucosylated GlcNAc acceptor are not detected under the same reaction conditions. The invention provides a highly convergent method for the synthesis and glycosylation remodeling of a class of biomedically important glycopeptides and glycoproteins such as recombinant monoclonal antibodies.

The present invention opens a new avenue for the synthesis of core fucosylated glycopeptides that are heretofore have been difficult to obtain by isolation from natural sources (because of structural heterogeneity in protein glycosylation) or by conventional chemical synthesis. The novel transglycosylation activity of Endo-F1, Endo-F2 and Endo-F3 now permits a highly convergent method for the synthesis of these compounds.

The present invention can be used to generate various core-fucosylated glycopeptides as biomarkers for cancer diagnosis. It is reported that tumor progression accompanies significant increase in core fucosylation of some glycoproteins.

The present invention can also be used to perform direct glycosylation remodeling of human IgG1-Fc and recombinant monoclonal antibodies. Natural and recombinant human IgG antibodies usually carry core fucose. A combined use of Endo-S (for de-glycosylation of fucosylated glycan) and Endo-F3 (or Endo-F2, Endo-D or their mutants) (for specifically adding back desired glycan) enables the glycosylation remodeling: of this class of glycoproteins. It should be emphasized that commonly used endoglycosidases such; as Endo-A and Endo-M cannot work on a fucosylated GlcNAc-protein acceptor. This invention addresses specifically this limitation.

The fucosylated glycopeptides and glycoproteins, produced according to the methods described herein, can be used for diagnosis and therapeutics. Approximately two-thirds of therapeutic proteins used on the market and/or currently in clinical trials are glycoproteins. However, the structural heterogeneity in different glycoforms of natural and recombinant glycoproteins presents a major barrier in developing glycoprotein-based drugs, as different glycoforms may have different biological activities and controlling glycosylation to a homogeneous glycoform is extremely difficult during expression. The previous discovery of the transglycosylation activity of a class of endoglycosidases represents a major advance in the field for glycosylation engineering to enhance glycoproteins' therapeutic and diagnostic potentials. However, the currently used endoglycosidases such as Endo-A and Endo-M are unable to work on core-fucosylated natural and recombinant glycoproteins. Thus, the discovery of the new property of Endo-F2, Endo-F3, Endo-D and their glycosynthase mutants.

The features and advantages of the present invention are more fully shown by the following non-limiting examples.

EXAMPLES

Chemical Synthesis of Asn-Linked Disaccharide Derivative Fmoc-Asn(Fucα1,6GlcNAc)-OH For screening the transglycosylation activity of ENGases on fucosylated GlcNAc acceptor, an Asn-linked disaccharide derivative was synthesized, that being, Fmoc-Asn (Fucα1,6GlcNAc)-OH (9), using the peracetylated GlcNAc-azide (1) [57] as the starting material, wherein the steps are shown in FIG. 1. Selective α-1,6-fucosylation [58] of 3 with per-O-trimethylsilyl α-fucopyranosyl iodide (4) as the glycosyl donor in the presence of 2,6-di-tert-butylpyridine, followed by in situ removal of the TMS protecting groups, gave the disaccharide derivative 5 in 61% yield. The newly formed glycosidic linkage was confirmed to be α-linkage as demonstrated by a relatively small coupling constant between H-1 and H-2 of the fucose (H-1, δ 4.82, d, $J_{1,2}$=3.68 Hz). After changing the O-protecting groups to O-acetyl groups, the resulting glycosyl azide 6 was reduced with $Me_3P$ in THF and then coupled with Fmoc-Asp-OtBu to afford the Asn-linked derivative 7. The tert-butyl group was selectively removed with a mild acid condition (20% TFA in $CH_2Cl_2$) without cleavage of the acid-labile α-1,6-fucosidic linkage to give the Asn-linked disaccharide 8 in 95% yield. Finally selective de-O-acetylation of 8 was achieved by treatment of 8 with $K_2CO_3$ in MeOH/THF to provide the N-Fmoc-protected Asn-disaccharide (9) in 85% yield, as shown in FIG. 1.

Figure 2:
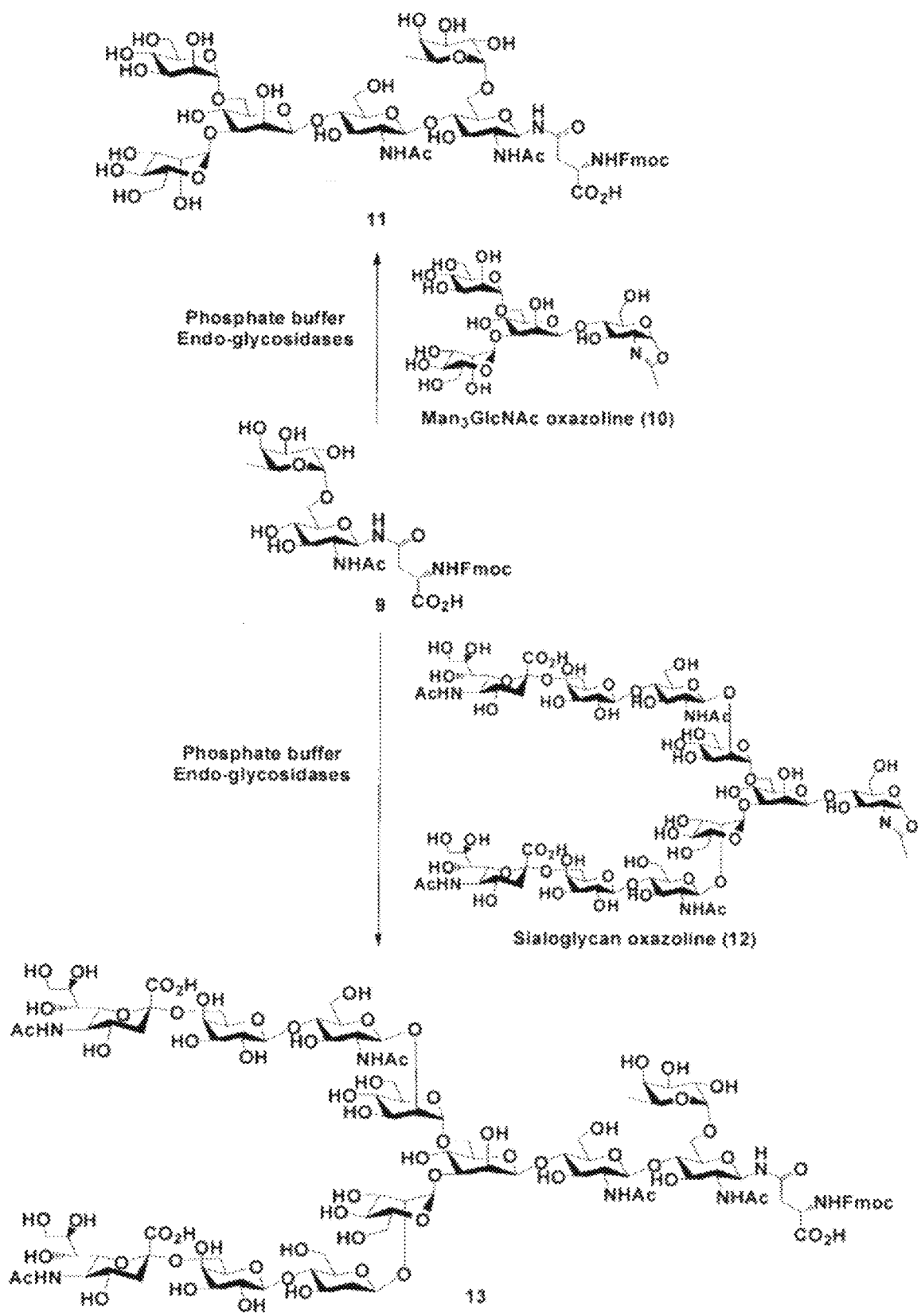
FIG. 2 shows the screening transglycosylation activity using the Fmoc-Asn(Fucα1,6GlcNAc)-OH (9) as the acceptor and synthetic sugar oxazolines (10 and 12) as the donor substrates.
Figure 3:
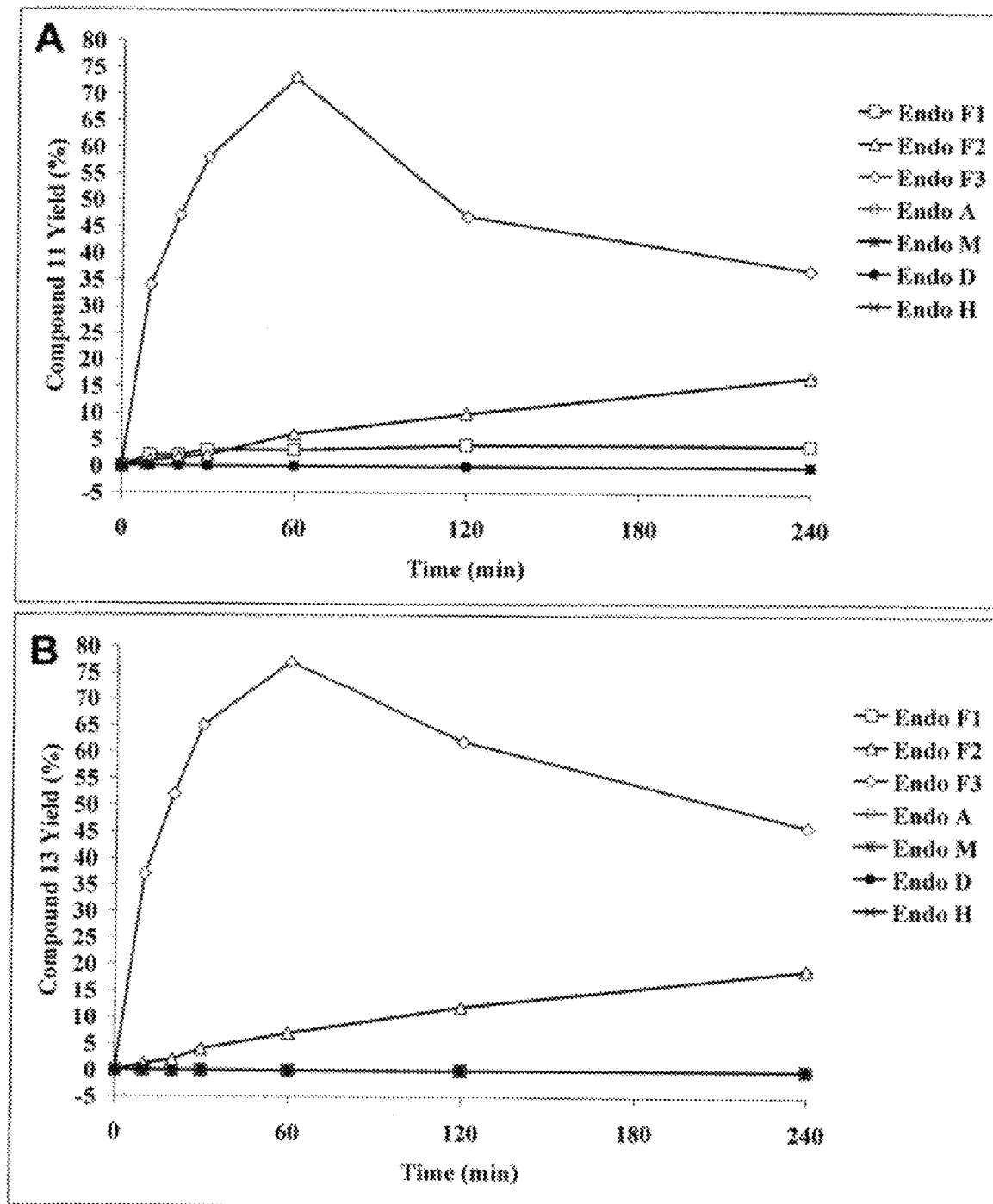
FIG. 3 shows the time courses of endoglycosidases-catalyzed transglycosylation on Fmoc-Asn(Fucα1,6GlcNAc)-OH (9) monitored by HPLC. Panel A: Man$_3$GlcNAc oxazoline (10) as the donor substrate; Panel B: sialoglycan oxazoline (12) as the donor substrate.
Figure 4:
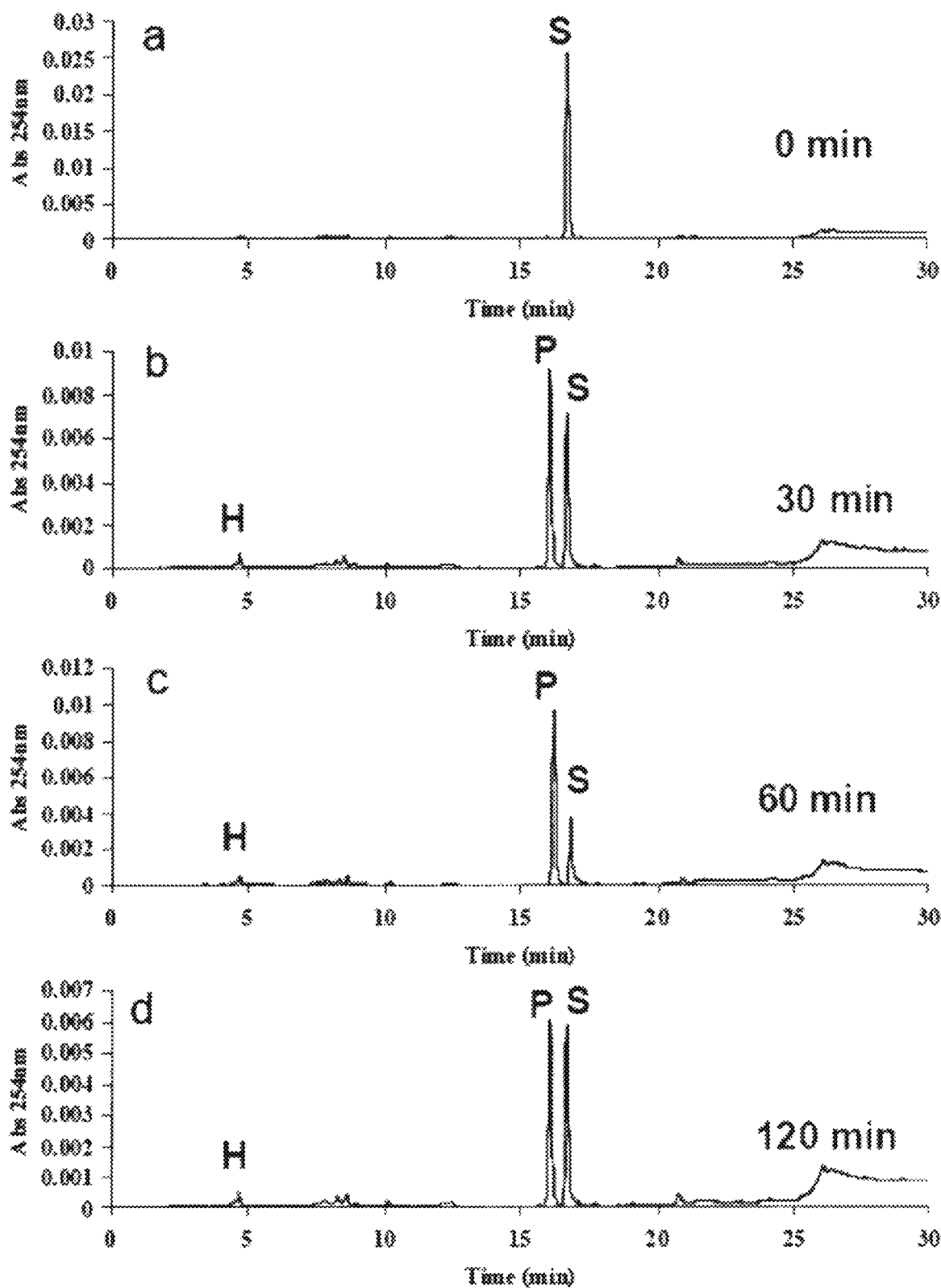
FIG. 4 shows the HPLC monitoring of the transglycosylation reaction between oxazoline 10 and acceptor 9 in the presence of Endo-F3. a) 0 min; b) 30 min; c) 60 min; and d) 120 min. The identity of the peaks was confirmed by ESI-MS analysis: S, acceptor 9; P, transglycosylation product 11; and H, Man3GlcNAc, (the hydrolysis product of oxazoline 10).

Screening of Transglycosylation Activity Using the Fucosylated GlcNAc-Asn as the Acceptor Substrate and Synthetic Sugar Oxazolines as the Donor Substrates With the synthetic disaccharide acceptor (9) in hand, a series of ENGases were screened for their ability to transfer an oligosaccharide to the Fucα1,6GlcNAc moiety. These include Endo-A [59] and Endo-M [60], Endo-H from *Streptomyces plicatus* [73], Endo-D from *Streptococcus pneumoniae* [63]; and Endo-F1, Endo-F2, and Endo-F3 from *Flavobacterium meningosepticum* [74-77]. These enzymes all hydrolyze N-glycans at the N,N'-diacetylchitobiose core, but they have different substrate specificity. It is known that Endo-A, Endo-H, and Endo-F1 hydrolyze high-mannose type and/or hybrid type N-glycans [59, 74, 73]; Endo-M can hydrolyze high-mannose type, hybrid type, and non-fucosylated bi-antennary complex-type N-glycans [60]; Endo-D is specific for a truncated and core-fucosylated N-glycan [63]; and Endo-F2 and Endo-F3 are able to cleave both core-fucosylated and non-fucosylated complex-type N-glycans [75, 76, 77], but Endo-F3 prefers core-fucosylated N-glycans [78]. Two synthetic sugar oxazolines, the Man3GlcNAc-oxazoline (10) [42] and the sialylated N-glycan oxazoline (12) [56], were used as donor substrates for screening the enzymes. If there was a transglycosylation activity, a corresponding core-fucosylated glycopeptide (11 or 13) would be produced, as shown in FIG. 2. Thus, a mixture of oxazoline (10) or (12) and acceptor 9 (donor/acceptor, 4:1) was incubated with an appropriate amount of the respective ENGase at 30° C. in a phosphate buffer (50 mM, pH 7.0) containing 10% DMSO. Inclusion of 10% DMSO significantly enhanced the solubility of the Fmoc derivative 9 in the buffer. The course of transglycosylation reaction was monitored by RP-HPLC analysis of reaction aliquots taken at intervals, and new peaks (products) were subject to ESI-MS analysis to confirm their identity. The screening results were summarized in FIG. 3. It was revealed that Endo-A, Endo-M, wild type Endo-D, and Endo-H did not show any transglycosylation activity towards the $\alpha$-1,6-fucosylated GlcNAc derivative, although the first three enzymes were previously shown to be able to transglycosylate non-fucosylated GlcNAc-Asn acceptor. In contrast, the Endo-F3 demonstrated remarkable transglycosylation activity toward the $\alpha$-1,6-fucosylated GlcNAc acceptor, with both the truncated glycan oxazoline (10) and the full-size complex type glycan oxazoline (12). The reaction led to the formation of the corresponding core-fucosylated N-glycan (11) and (13) respectively, in over 70% yield within 1 h. The yield was based on the conversion of the acceptor. It should be mentioned that only a single transglycosylation product was formed when oxazoline 10 or 12 were used, indicating the specificity for the enzymatic transglycosylation. A HPLC profile of the reaction between oxazoline 10 and acceptor 9 in the presence of Endo-F3 was shown in FIG. 4. It was found that a gradual hydrolysis of the product by Endo-F3 occurred when the mixture was incubated with the enzyme for a prolonged time. This was expected, due to the inherent hydrolytic activity of Endo-F3. However, the Endo-F3 catalyzed transglycosylation from the sugar oxazoline was surprisingly fast, allowing a significant accumulation of the transglycosylation product. These results suggest that the use of the highly active sugar oxazoline as donor substrate favours the transglycosylation. The Endo-F2 also showed transglycosylation activity on the 1,6-fucosylated GlcNAc acceptor, but the reaction was much slower than that catalyzed by Endo-F3. In comparison, the Endo-F1 only showed marginal transglycosylation activity when Man3GlcNAc-oxazoline (10) was used as donor substrate, and did not show any activity when the sialylated glycan oxazoline (12) was used as donor substrate (FIG. 3). These results clearly demonstrate the distinct substrate specificity of these endoglycosidases in transglycosylation. Products 11 and 13 from the transglycosylation by Endo-F2 and Endo-F3 were purified by RP-HPLC and first characterized by mass spectrometric analysis. The MALDI-TOF MS data of 11 (calculated, M=1392.50; found (m/z), 1416.12 [M+Na]$^+$) indicated that the product was an adduct of the Man3GlcNAc-oxazoline and acceptor 9; the ESI-MS of 11 revealed two major m/z species at 1393.58 and 1247.60, which corresponded to [M+H]$^+$ and [M−Fuc+H]$^+$, respectively. The presence of fragment [M−Fuc+H]$^+$ suggested that the transferred oligosaccharide was attached to the GlcNAc moiety rather than the Fuc moiety in the acceptor.

Further characterization of product 11 was carried out by specific enzymatic transformations. Endo-D digestion of the isolated 11 gave tetrasaccharide Man$_3$GlcNAc that was identical to an authentic sample, and the Fmoc-Asn(Fuc$\alpha$1, 6GlcNAc)-OH. Since Endo-D is known to specifically cleave the $\alpha$-1,4-glycosidic linkage in the N,N'-diacetylchitobiose unit of a core-fucosylated Man$_3$GlcNAc$_2$ moiety [63], the observed result indicated that the transferred Man3GlcNAc was attached specifically to the 4-OH of the GlcNAc moiety in acceptor 9 to form the desired $\alpha$-1,4 glycosidic linkage. The sialylated product (13) was similarly characterized by MS analysis. Notably, this is the first report showing a transglycosylation activity of Endo-F2 and Endo-F3 with a sugar acceptor [61]. The Endo-F2 and Endo-F3 also represent the first endoglycosidases capable of glycosylating core fucosylated GlcNAc acceptor to form a new core-fucosylated N-glycopeptide.

Figure 5:
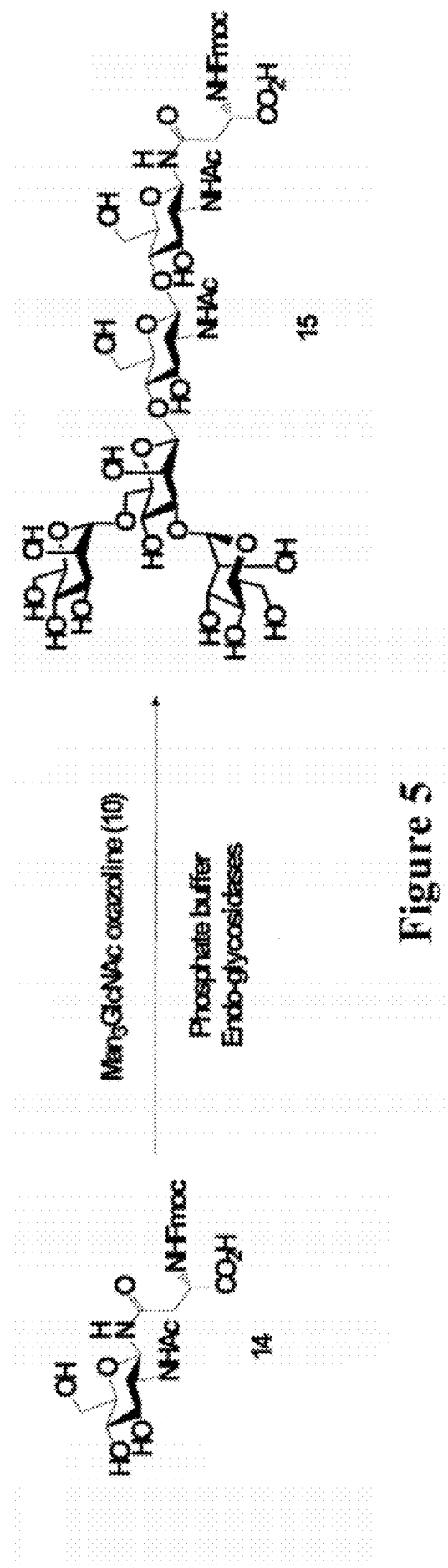
FIG. 5 shows the screening transglycosylation activity using non-fucosylated GlcNAc-Asn-Fmoc (14) as the acceptor and Man$_3$GlcNAc oxazolines (10) as the donor substrate.
Figure 6:
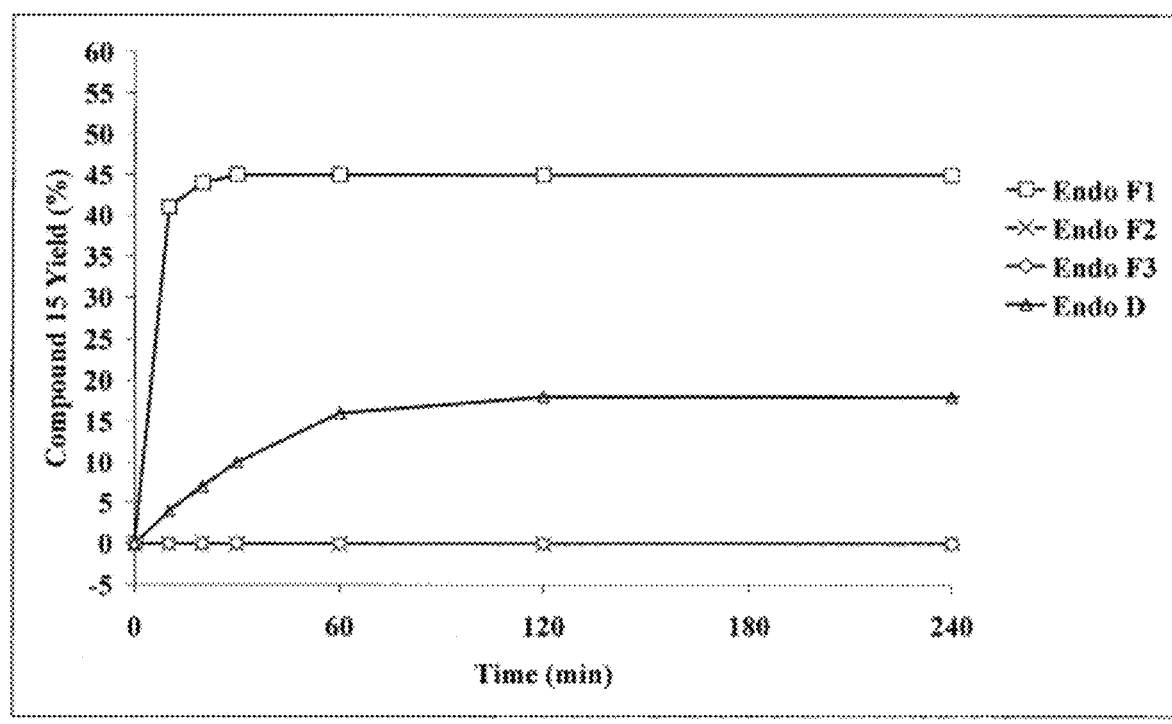
FIG. 6 shows the HPLC-monitored time courses of Endoglycosidases-catalyzed transglycosylation on Fmoc-Asn(GlcNAc)-OH using Man$_3$GlcNAc oxazoline as the donor substrate.

Endo-F2 and Endo-F3 Do not Accept Non-Fucosylated GlcNAc Derivative as Acceptor Substrate for Transglycosylation The significant transglycosylation activity of Endo-F2 and Endo-F3 on Fmoc-Asn(Fuc$\alpha$1,6GlcNAc)-OH also prompted the examination to determine how these *Flavobacterium* enzymes act on non-fucosylated GlcNAc acceptor. It has been previously shown that Endo-A and Endo-M are very efficient to transglycosylate non-fucosylated GlcNAc moiety [40]. Accordingly, the transglycosylation of Endo-F1, Endo-F2, Endo-F3, and wild type Endo-D on Fmoc-Asn(GlcNAc)-OH (14) was tested using Man$_3$GlcNAc oxazoline (10) as the donor substrate and shown in FIG. 5. The results were summarized in FIG. 6. Surprisingly, Endo-F2 and Endo-F3 did not exhibit transglycosylation activity on the non-fucosylated GlcNAc acceptor under the screening conditions. On the other hand, the Endo-F1 enzyme, which did not show activity on the fucosylated GlcNAc acceptor as described above, demonstrated significant transglycosylation activity with the non-fucosylated GlcNAc (14) to lead to a rapid formation of the corresponding product (15). The yield reached 45% within 30 min. However, a prolonged incubation did not result in further increase in yield. HPAEC-PAD analysis of the reaction mixture revealed that the moderate yield was mainly due to the simultaneous hydrolysis of the sugar oxazoline (10), which was completely gone within 30 min. Interestingly, the product Man3GlcNAc2-Asn(Fmoc) (15) was not hydrolyzed even for a prolonged incubation, indicating that the truncated N-glycan product was a poor substrate of Endo-F1. The Endo-D is an interesting case. The results indicated that Endo-D could use Man3GlcNAc-oxazoline (10) as donor substrate and GlcNAc-Asn derivative (14) as acceptor for transglycosylation, albeit at a low yield, as shown in FIG. 6. This result is consistent with a recent report on Endo-D [62]. However, when the $\alpha$-1,6-fucosylated GlcNAc derivative (9) was used, no transglycosylation product was detected, as shown in FIG. 3. Given the fact that Endo-D could efficiently hydrolyze $\alpha$-1,6-fucosylated Man3GlcNAc2 core [63], it is conceivable to think that Endo-D should be able to accommodate $\alpha$1-6-fucosylated GlcNAc derivative (9) as acceptor for transglycosylation. The failure to detect the transglycosylation product might be due to the quick Endo-D catalyzed hydrolysis of the product in situ before it was released from the catalytic site. Indeed, incubation of Endo-D and the purified core-fucosylated Man3GlcNAc2-Asn(Fmoc) (11) obtained from the Endo-F3 transglycosylation resulted in a very quick hydrolysis of 11.

The presence of an $\alpha$-1,6-linked fucose in the GlcNAc acceptor seems essential for recognition of the acceptor by Endo-F2 and Endo-F3 for an efficient transglycosylation. In contrast, attachment of a core fucose on the GlcNAc moiety completely blocked the accommodation of the acceptor for transglycosylation by Endo-F1, Endo-A, and Endo-M. It should be pointed out that the wild type Endo-F2 and Endo-F3 could still hydrolyze the transglycosylation product thus formed. One way to address this issue is to create glycosynthase mutants that is capable of working on the highly activated sugar oxazolines for transglycosylation but lacks product hydrolysis activity. It has been previously shown that site-directed mutation at a specific Asn residue, the Asn175 in Endo-M and Asn171 in Endo-A, which promotes oxazoline formation during hydrolysis, could lead to glycosynthase mutants useful for synthesis [52, 56, 55]. The crystal structure of Endo-F3 was solved and the two conserved active residues at the catalytic site were identified as Asp126 and Glu128 [79]. In the substrate-assisted mechanism of the family 18 endoglycosidases [80-81], the Glu128 of Endo-F3 serves as a general acid to protonate the glycosidic bond; whereas the Asp126 was assigned a secondary role, assumingly having the same function as the Asn171 of Endo-A to promote the formation of the oxazolinium ion intermediate, and to stabilize it, by interactions with the 2-acetamido group in the GlcNAc moiety [79].

Figure 7:
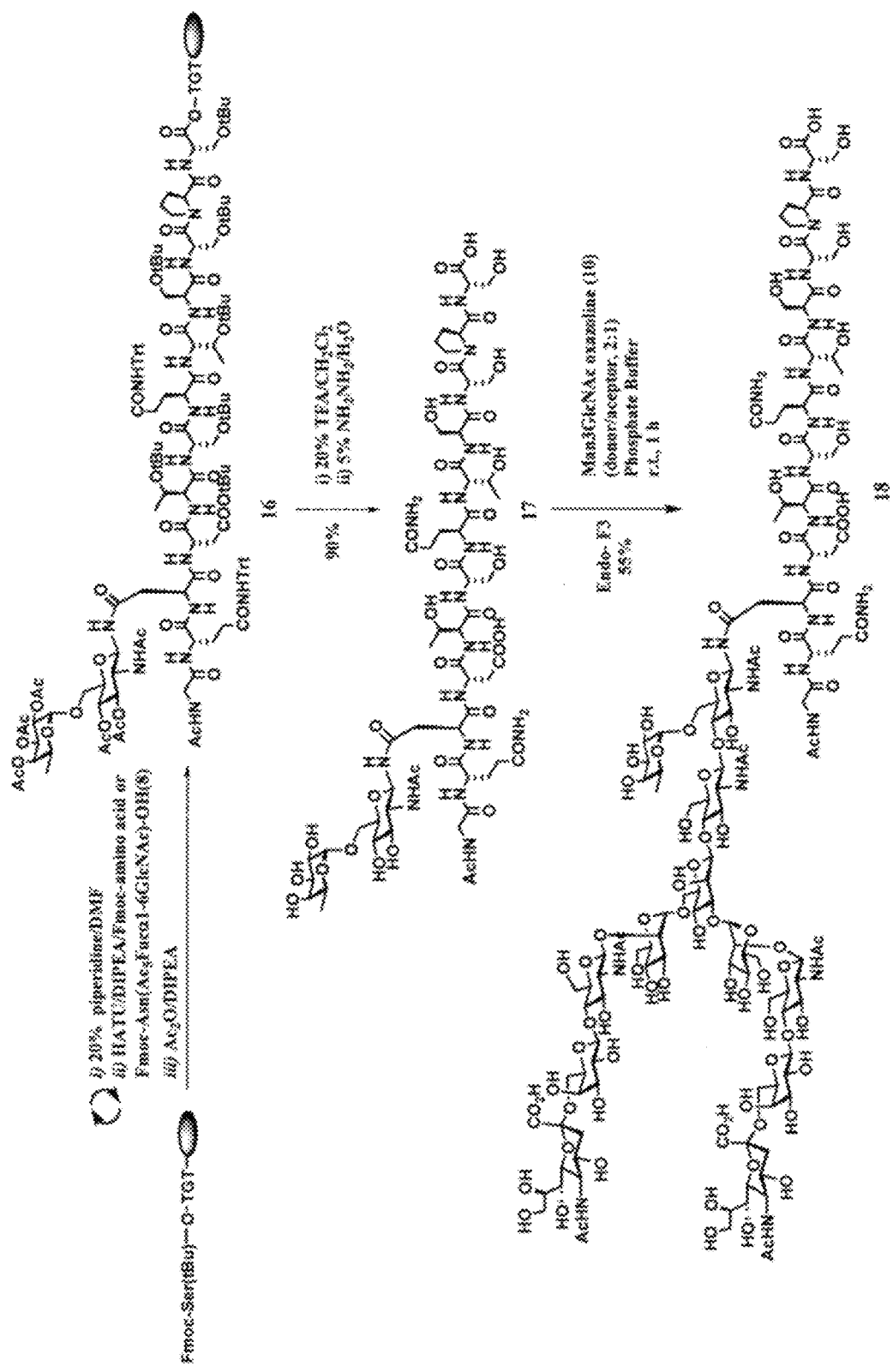
FIG. 7 shows the chemoenzymatic synthesis of a sialylated and core-fucosylated CD52 antigen.
Figure 8:
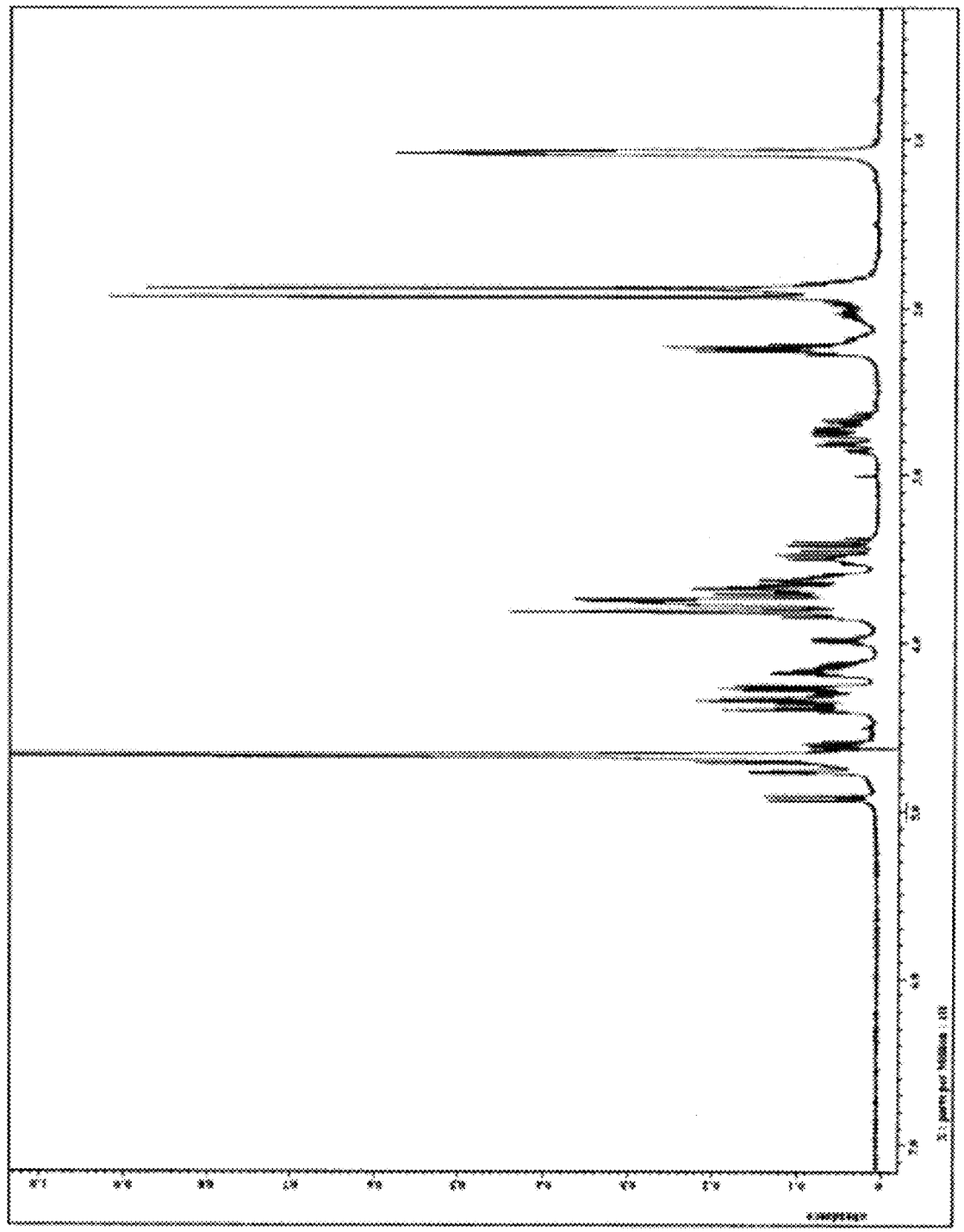
FIG. 8 shows the $^1$H NMR spectrum of Fucα1,6GlcNAc-CD52 (17).
Figure 9:
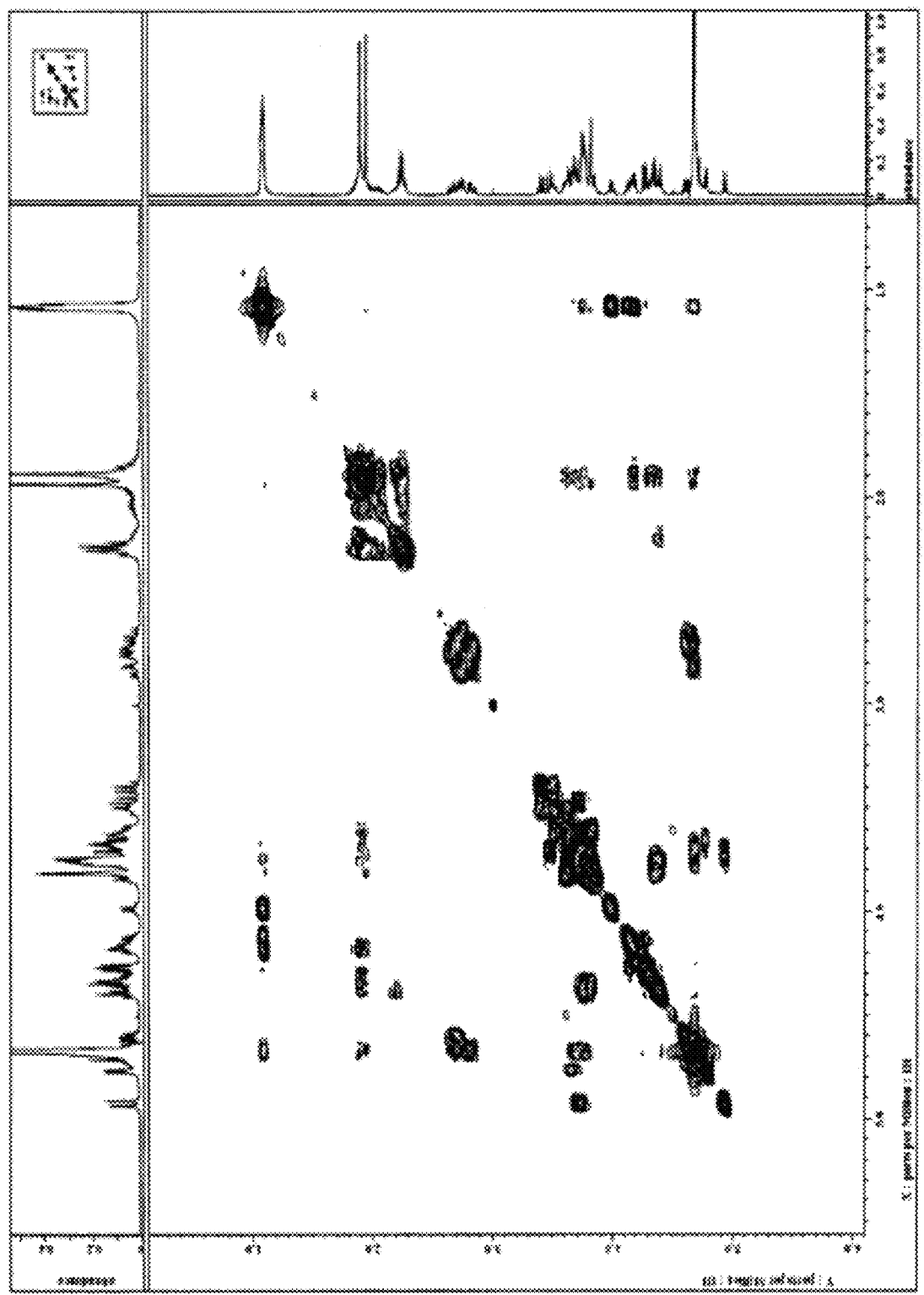
FIG. 9 shows the $^1$H-$^1$H 2D COSY NMR spectrum of Fucα1,6GlcNAc-CD52 (17).
Figure 10:
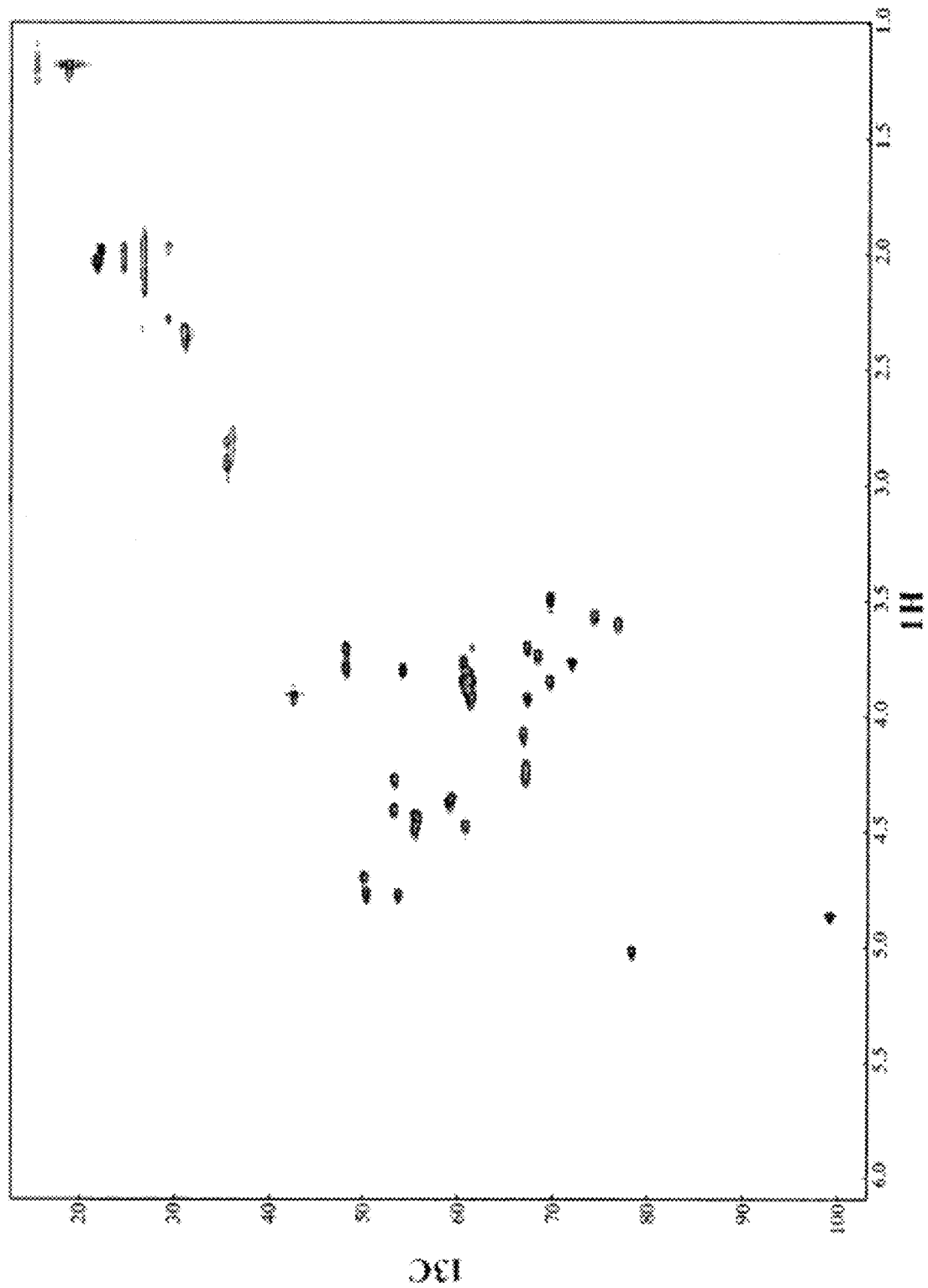
FIG. 10 shows the 1H-$^{13}$C 2D HSQC NMR spectrum of Fucα1,6GlcNAc-CD52 (17).

Convergent Chemoenzymatic Synthesis of a Sialylated and Core-Fucosylated Complex-Type Glycoform of CD52 Antigen The remarkable transglycosylation activity of Endo-F2 and Endo-F3 with α-1,6-fucosylated GlcNAc acceptor, together with their flexibility in accepting different sugar oxazolines as donor substrates, opens a new avenue to a highly convergent chemoenzymatic synthesis of core-fucosylated complex type N-glycans, glycopeptides, and/or glycoproteins. As a test case, a sialylated and core-fucosylated complex-type glycoform of the CD52 glycopeptide antigen was synthesize. CD52 is a GPI-anchored glycopeptide antigen found on human lymphocytes and sperm cells. It is a glycopeptide consisting of only 12 amino acid residues but carrying a large complex-type N-glycan at the Asn-3 residue [64-66]. Several truncated CD52 glycoforms were made previously by chemical methods [67-69]. The CD52 antigen was previously used as a model glycopeptide to test our chemoenzymatic method [82, 55, 70]. However, a full-size complex-type CD52 antigen carrying both terminal sialic acid residues and core fucose moiety had not been made by either chemical or chemoenzymatic method. A convergent chemoenzymatic synthesis of the target CD52 antigen required the preparation of a CD52 polypeptide containing a Fucα1,6GlcNAc moiety at the Asn-3. To avoid a strong acidic condition for retrieving the polypeptide from the solid support in the Fmoc approach, the solid-phase peptide synthesis was performed on an acid-labile O-link TGT-resin, which can be cleaved by mild acid treatment, as shown in FIG. 7. Fmoc-Asn(Ac$_5$Fucα1-6GlcNAc)-OH (8) was used as a building block to replace the residues at Asn-3 during the synthesis to introduce a Fucα1,6GlcNAc moiety. HATU (0.5 M in DMF) and DIPEA (1.0 M in DMF) (1:1, v/v) were used as the coupling reagent and piperidine (20% in DMF) was used as the deblocking reagent. 4-fold excess of Fmoc-protected building blocks were used for each coupling reaction cycle. The N-terminus amino group was protected with an acetyl group by treatment with Ac$_2$O/DIPEA. The disaccharide-containing polypeptide was released from the resin (16) by treatment with 20% TFA in CH$_2$Cl$_2$ at r.t. for 5 h, with simultaneous removal of the side-chain protecting groups (Trt and t-Bu). The Ac groups on the disaccharide were removed by treatment with 5% aqueous hydrazine at r.t. for 1 h. The crude product was then purified by preparative HPLC to give the Fucα1,6GlcNAc-CD52 (17) in an excellent overall yield (90%), FIG. 7. The product was characterized by ESI-MS (calculated, M=1598.64; found (m/z), 1599.16 [M+H]$^+$) and a detailed NMR analysis, with results in FIGS. 8, 9 and 10.

Figure 11:
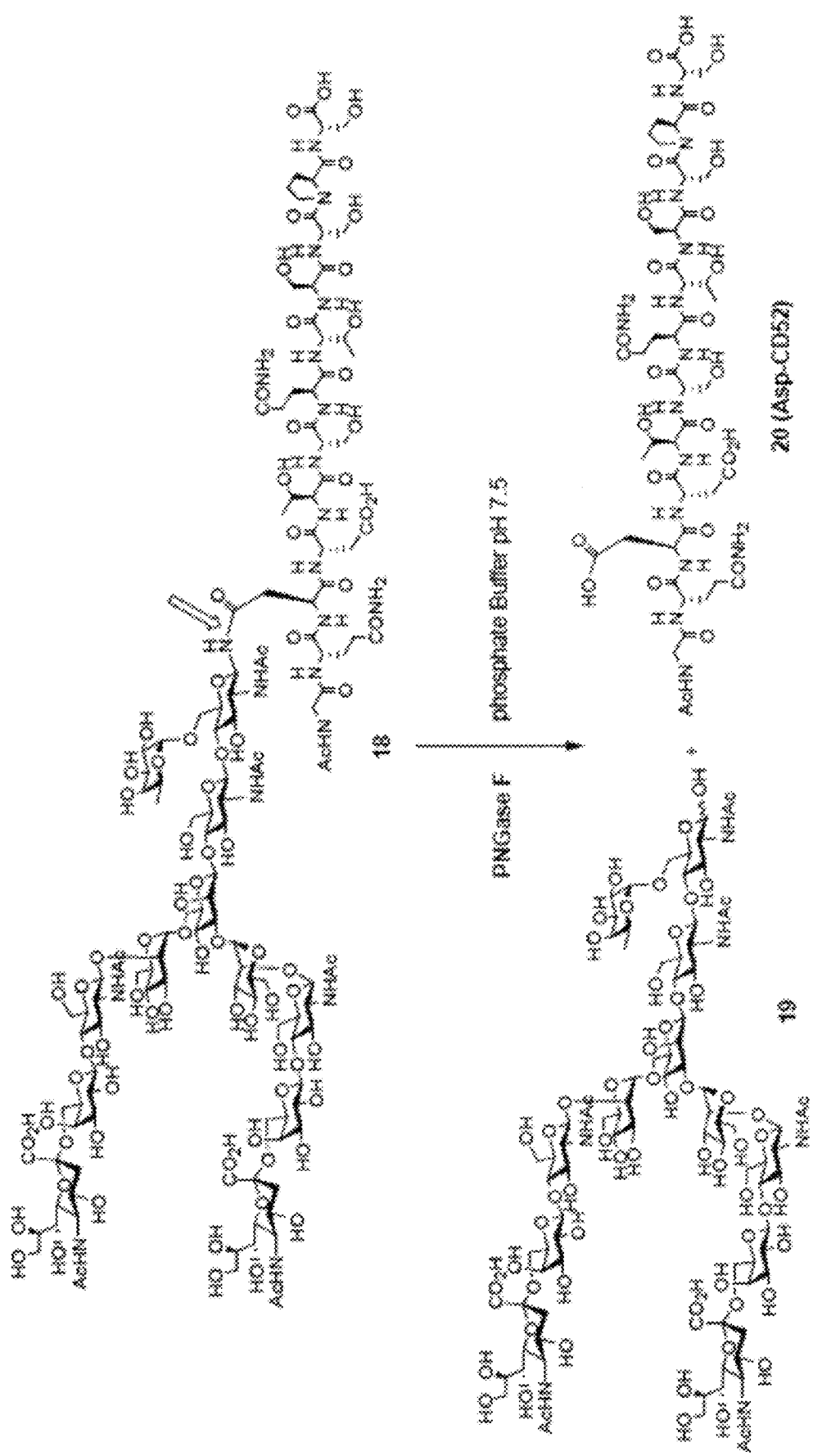
FIG. 11 shows a scheme for PNGase F digestion of CD52 glycoprotein (18).
Figure 12:
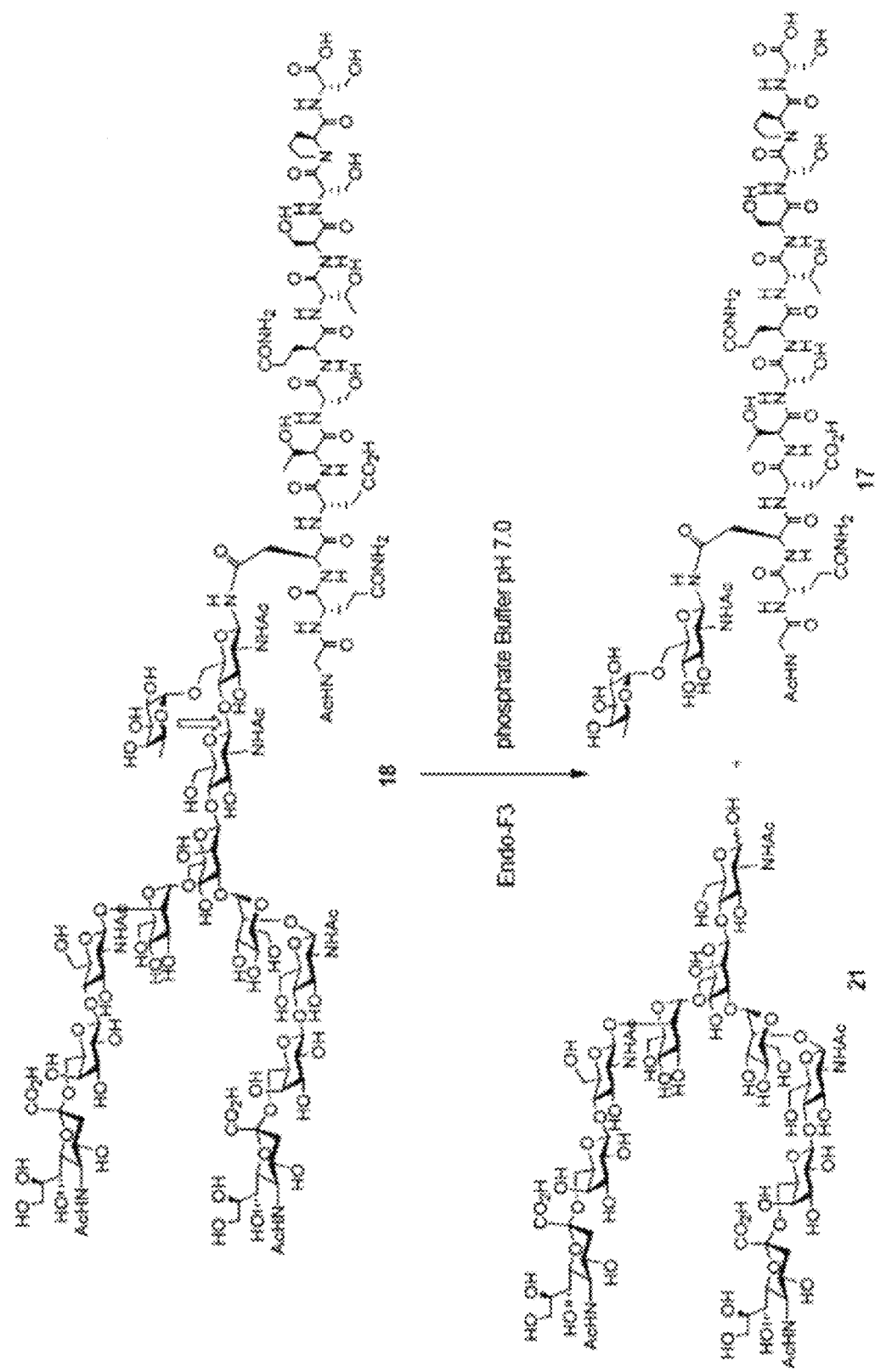
FIG. 12 shows a scheme for Endo-F3 digestion of CD52 glycoprotein (18).
Figure 13:
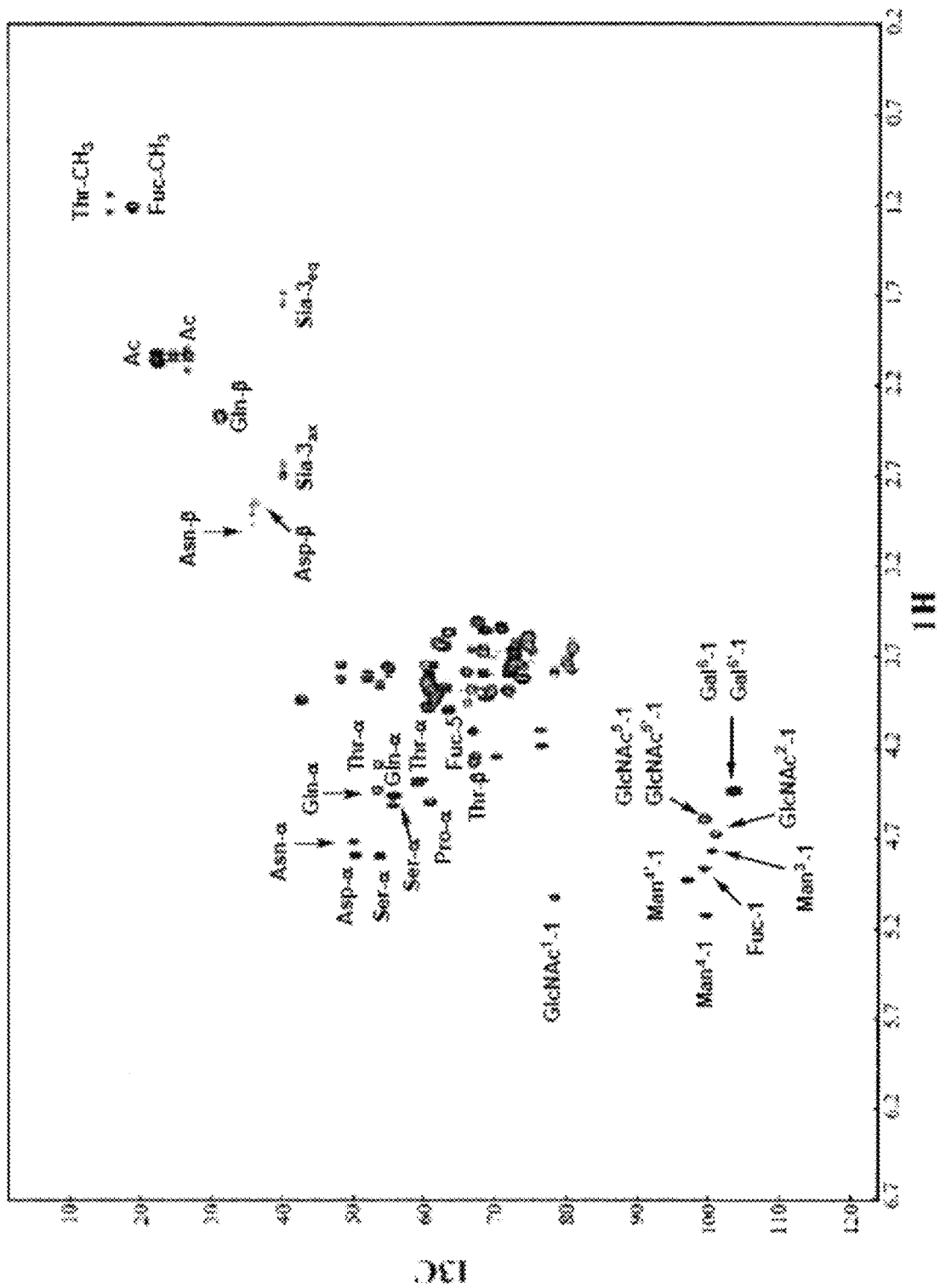
FIG. 13 shows the $^1$H-$^{13}$C 2D HSQC NMR spectrum of the core-fucosylated complex type CD52 (18).
Figure 14:
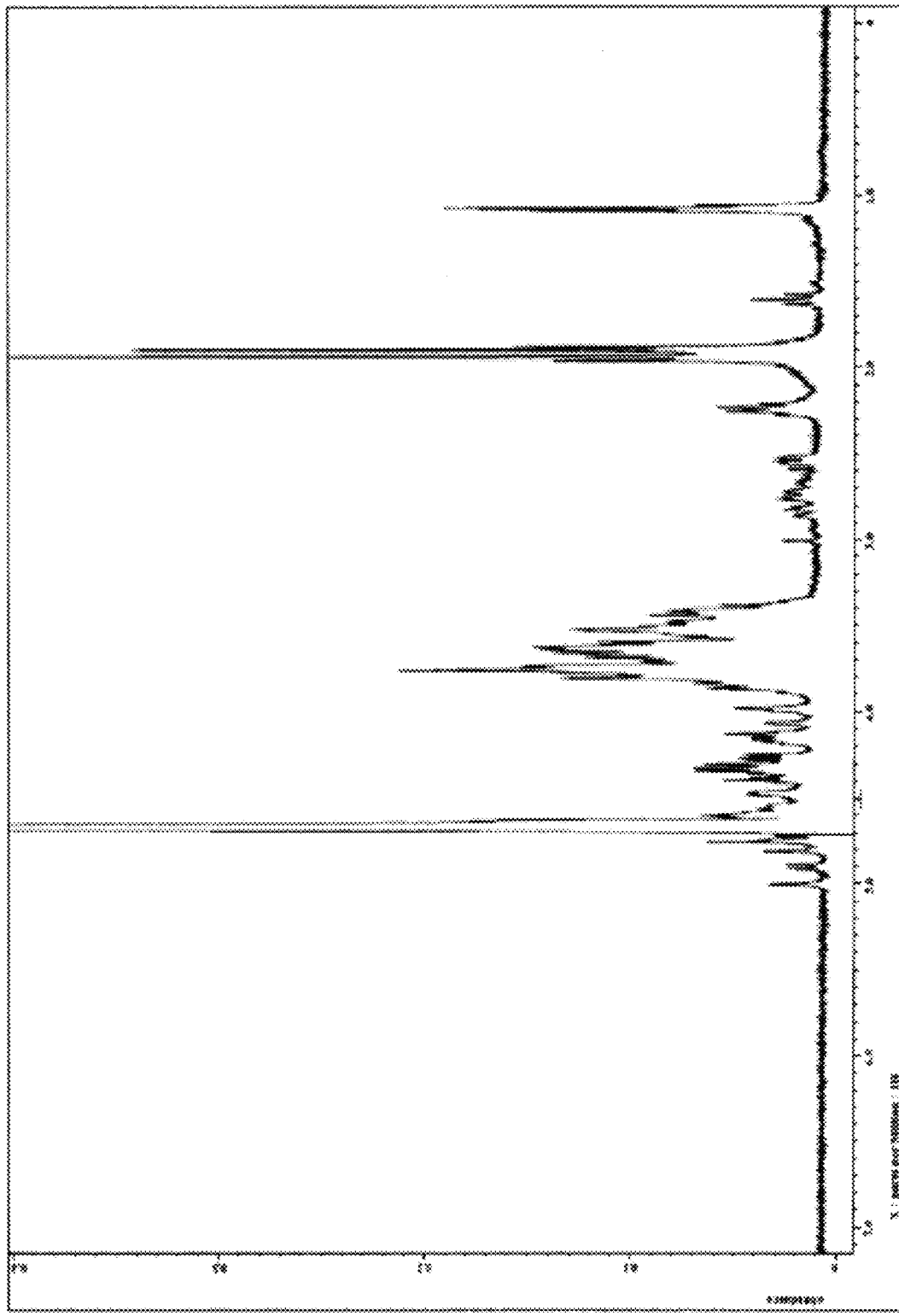
FIG. 14 shows the $^1$H NMR spectrum of the core-fucosylated complex type CD52 (18).
Figure 15:
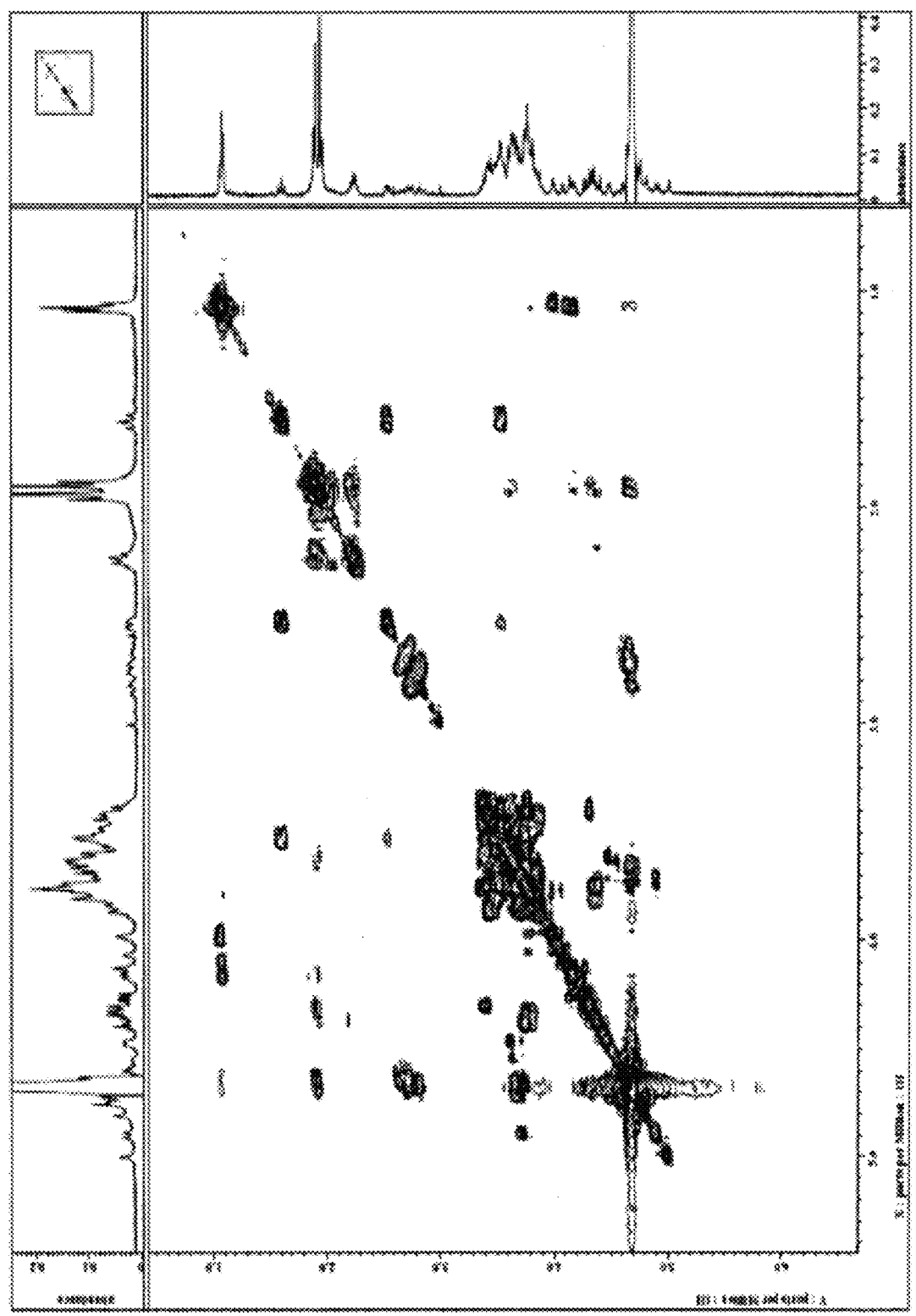
FIG. 15 shows the $^1$H-$^1$H 2D COSY NMR spectrum of the core-fucosylated complex type CD52 (18).

With the Fucα1,6GlcNAc-CD52 (17) in hand, the transglycosylation with Endo-F3 was performed, using sialoglycan oxazoline (12) (FIG. 2) as donor substrate, which was efficiently synthesized from a free N-glycan by a single-step conversion in water [56]. Thus, incubation of 12 and 17 (molar ratio: donor/acceptor, 2:1) with Endo-F3 in a phosphate buffer (pH 7.0) led to the formation of the CD52 glycoform (18) carrying a sialylated and core-fucosylated bi-antennary N-glycan. The reaction was monitored by HPLC. When the formation of 18 reached a plateau, the reaction was stopped and the product was isolated in 55% yield by HPLC. The efficiency of the transglycosylation was quite impressive, given the fact that only two-fold of the donor substrate was used. Using the Endo-F2 to replace Endo-F3 for the transglycosylation gave a 25% yield of 18 after a longer period (6 h) of incubation (data not shown). ESI-MS of 18 gave the expected m/z species (calculated for $C_{137}H_{221}N_{21}O_{90}$, M=3600.34; found (m/z), 1201.66 [M+3H]$^{3+}$). Further characterization of the product was carried out by specific enzymatic transformations. Digestion of 18 with peptide-N4-(N-acetyl-β-D-glucosaminyl)asparagine amidase F (PNGase F), which specifically hydrolyzes the β-aspartylglucosylamine bond of N-glycopeptides and N-glycoproteins [83-84], yielded the expected sialoglycan 19 (ESI-MS: calculated for $C_{90}H_{148}N_6O_{66}$, M=2368.84; found (m/z), 1185.82 [M+2H]$^{2+}$) and the expected aspartic acid-containing CD52 peptide (20) (ESI-MS: calculated for $C_{47}H_{74}N_{14}O_{26}$, M=1250.49; found (m/z), 1251.56 [M+H]$^+$, 626.38 [M+2H]$^{2+}$ as shown in FIG. 11. On the other hand, incubation of purified 18 with large amount of Endo-F3 gave Fucα1,6GlcNAc-CD52 (17) and the corresponding N-glycan 21, as shown in FIG. 12. These results suggest that the transferred glycan was attached to the GlcNAc in the peptide through the GlcNAc-α-1,4-GlcNAc linkage. Finally, NMR was conducted and a detailed NMR analysis was conducted as shown in FIGS. 14 and 15. A $^1$H-$^{13}$C 2D HSQC NMR analysis of 18 permitted the assignment of all the sugar anomeric protons and anomeric carbons, as well as all the amino acid residues in the product, as shown in FIG. 13. These experiment data confirmed that the product obtained was the expected full-size, sialylated and core-fucosylated CD52 antigen.

It has been shown herein that the GH family 18 *Flavobacterium meningosepticum* endoglycosidases Endo-F2 and Endo-F3 demonstrate novel transglycosylation activities and are able to glycosylated α-1,6-fucosylated GlcNAc-peptide by using sugar oxazoline as a donor substrate. The novel activity of Endo-F2 and Endo-F3 was successfully applied for a convergent chemoenzymatic synthesis of a full-size CD52 glycopeptide antigen carrying both terminal sialic acid and core fucose. This is the first discovery of transglycosylation activity of Endo-F1, Endo-F2 and Endo-F3 that show distinct acceptor substrate specificity. This is the first report on endoglycosidases capable of taking core-fucosylated GlcNAc-peptides for transglycosylation. In addition to the usefulness for complex glycopeptide synthesis, the unusual transglycosylation activity discovered may be used for glycosylation remodelling of monoclonal antibodies that usually carry core fucosylated N-glycans at the Fc domain but can be specifically de-glycosylated by an endoenzyme to provide a core-fucosylated GlcNAc acceptor at the glycosylation site.

Cloning and Expression of Wild Type Endo-F3 and the D126A (SEQ ID NO: 6) and D126Q (SEQ ID NO: 7) Mutants.

Standard molecular cloning and site-directed mutagenesis methods were used. Initial cloning of the Endo-F3 gene into the PGEX-2T vector and its transformation in E. coli for expression resulted in formation of inclusion bodies after overexpression in E. coli. The inclusion bodies were solubilized in 8M urea and refolded with about 6% efficiency resulting in an active fusion protein. This procedure gave an active Endo-F3 enzyme but the overall expression efficiency was low. Alternatively, the Endo-F3 gene was cloned into the pCPD4 vector which has been shown to help protein solubility. The resulting plasmid pCPD-EndoF3 was used for transforming E. coli (BL21 DE3) and led to a high-yield (35-50 mg/liter) expression of soluble fusion protein EndoF3-CPD EndoF3 PCD, which showed high activity for N-glycan hydrolysis and also for transglycosylation.

For the expression of the D126A and D126Q mutants, the QuickChange site-directed mutagenesis kit (Stratagene) was applied to generate the mutants. Briefly, primers containing the desired mutation were used to perform PCR using pCPD-EndoF3 as a template. After PCR the template DNA was digested with DpnI and then the mixture was transformed into DH5α max efficiency cells (Invitrogen). The resulting plasmid was isolated and used to transform E. coli (BL21 DE3) to over produce the respective mutants. Related Endo-F1 and Endo-F 2 mutants were overproduced in a similar manner.

EndoF3 Mutants Catalyzed Transglycosylation Using Complex-Type Sialoglycan Oxazoline (12) as Donor Substrate and Fmoc-Asn(Fucα1,6GlcNAc)-OH (9) as Acceptor Substrate.

Figure 22:
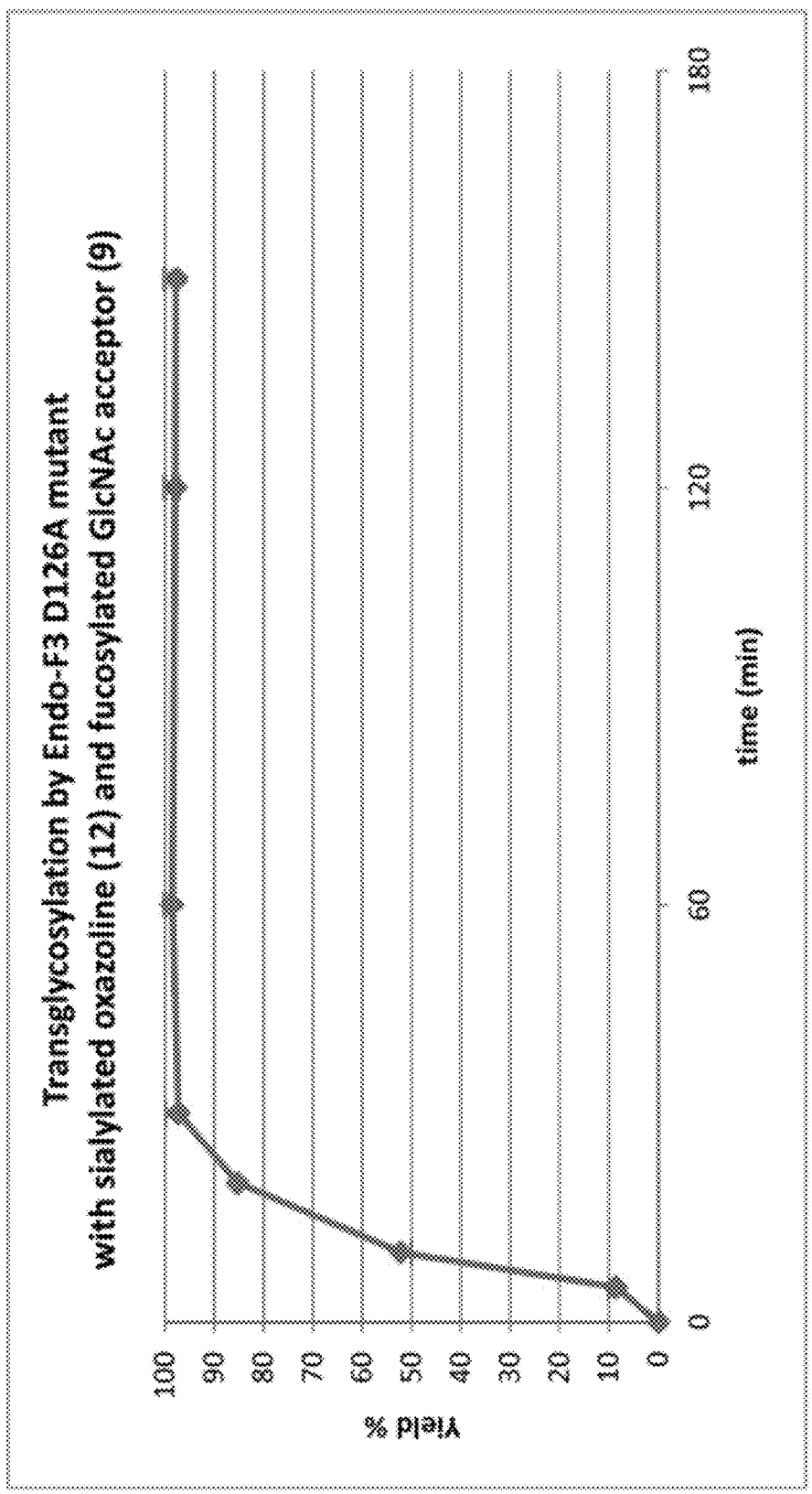
FIG. 22 shows the time courses of the transglycosylation of the fucosylated GlcNAc acceptor (9) with sialoglycan oxazoline (12) of FIG. 2 under the catalysis of glycosynthase mutant, Endo-F3 D126A.

A mixture of acceptor 9 (25 µg, 36 nmol) and sialoglycan oxazoline 12 (290 µg, 145 nmol) in phosphate buffer (50 mM, pH 7.0, 12 µL) was incubated at 30° C. with Endo F3 D126A (SEQ ID NO: 6) (12 µg) or Endo F3 D126Q (SEQ ID NO: 7) (6 ug) for 18 h. The reaction was monitored by analytic HPLC. The product was purified by RP-HPLC to give Fmoc-Asn(Sia$_2$Gal$_2$GlcNAc$_2$Man$_3$GlcNAc$_2$Fuc)-OH (13) as characterized by HPLC and ESI-MS as described above. FIG. 22 shows the time courses of the transglycosylation of the fucosylated GlcNAc acceptor (9) with sialoglycan oxazoline (12) under the catalysis of glycosynthase mutant, Endo-F3 D126A.

Chemoenzymatic Synthesis of Sialylated and Core-Fucosylated Complex-Type Glycoform of CD52 (18) by Endo F3 Mutants.

A mixture of CD52 peptide 17 (2 mg, 1.25 µmol) and sialoglycan oxazoline 12 (5 mg, 2.5 µmol) in phosphate buffer (50 mM, pH 7.0, 250 µL) was incubated at 30° C. with Endo-F3 D126A (SEQ ID NO: 6) (240 µg) or Endo F3 D126Q (SEQ ID NO: 7) (160 ug) for 18 h. The reaction was quenched with 1% TFA (10 µL) and the residue was subject to preparative RP-HPLC to give CD52-Sia$_2$Gal$_2$GlcNAc$_2$Man$_3$GlcNAc$_2$Fuc (18) as a white powder (yield: >90%). The product was characterized by HPLC, ESI-MS, and NMR as described above.

Chemoenzymatic Synthesis of Core-Fucosylated Complex-Type Glycoform of IgG Fc Fragment by Endo-F3 Wild-Type and Mutants. Papain Digestion of Full-Length Antibody Rituximab.

The antibody was digested with protease papain according to the reported method [87] with some modifications. Briefly, a solution of rituximab (20 mg) in a Tris-Cl buffer (20 mM, pH 6.5, 20 mL) containing L-cysteine (2 mM) was incubated with papain (200 µg) at 37° C. The reaction was monitored by SDS-PAGE and LC-MS. When the production of an Fc fragment reached plateau (after 2 h), the reaction mixture was loaded on a column of protein A-agarose resin (5 ml) that was pre-equilibrated with a Tris-Cl buffer (20 mM, pH 8.0). The column was washed with Tris-Cl (20 mM, pH 8.0, 25 mL) and glycine-HCl (20 mM, pH 5.0, 20 mL) successively. The bound Fc fragments were then eluted with glycine-HCl (100 mM, pH 2.5, 20 mL) and the elution fractions were immediately neutralized with Tris-Cl buffer (1.0 M, pH 8.8). The fractions containing the Fc fragments were combined and concentrated by centrifugal filtration (Amicon® ultra centrifugal filter, Millipore, Billerica, Mass.) to give IgG-Fc (3.5 mg). LC-MS: calculated for non-glycosylated IgG-Fc dimer, M=49896; found (after deconvolution): 52763 (G0F/G0F homodimer), 52925 (G0F/G1F heterodimer), 53084 (G1F/G1F homodimer), and 53400 (G2F/G2F homodimer).

De-Glycosylation of the Fc Fragments by Endo-S to Prepare Fucα1,6GlcNAc-Fc.

A solution of the purified IgG-Fc (2 mg) in a Tris-Cl buffer (50 mM, pH 7.0, 0.4 mL) was incubated with Endo-S (20 µg) at 30° C. After 30 min, the SDS-PAGE and LC-MS indicated the completion of the deglycosylation. The product was then purified through protein-A affinity chromatography following the procedures described above to give the Fucα1,6GlcNAc-Fc (2 mg, quantitative yield). ESI-MS: calculated for Fucα1,6GlcNAc-Fc, M=50594; found (based on deconvolution of the MS spectrum), M=50573.

Transglycosylation to Fucα1,6GlcNAc-Fc by EndoF3 Wild-Type or Mutants.

A solution of Fucα1,6GlcNAc-Fc (5 mg) and sialoglyan oxazoline 12 (10 mg) in a phosphate buffer (50 mM, pH 7.0, 500 µl) was incubated with the Endo F3 (250 ug) or Endo F3 D126A (500 mg) or Endo F3 D126Q (250 mg) at 30° C. The reactions were monitored by LC-MS. After 5 h, the resulted Sia$_2$Gal$_2$GlcNAc$_2$Man$_3$GlcNAc$_2$Fuc-Fc was purified through the protein-A affinity column as described above. ESI-MS: calculated for Sia$_2$Gal$_2$GlcNAc$_2$Man$_3$GlcNAc(α1,6Fuc)GlcNAc-Fc homodimer, MW=53263 Da; found (based on deconvolution of MS data), 53266.

Chemoenzymatic Synthesis of Core-Fucosylated Complex-Type Glycoform of Full Length IgG by Endo-F3 Wild-Type and Mutants. Cleavage of Native Glycoforms of Rituximab by Wide-Type Endo-S to Give Rituximab-GlcNAcFuc.

Figure 23:
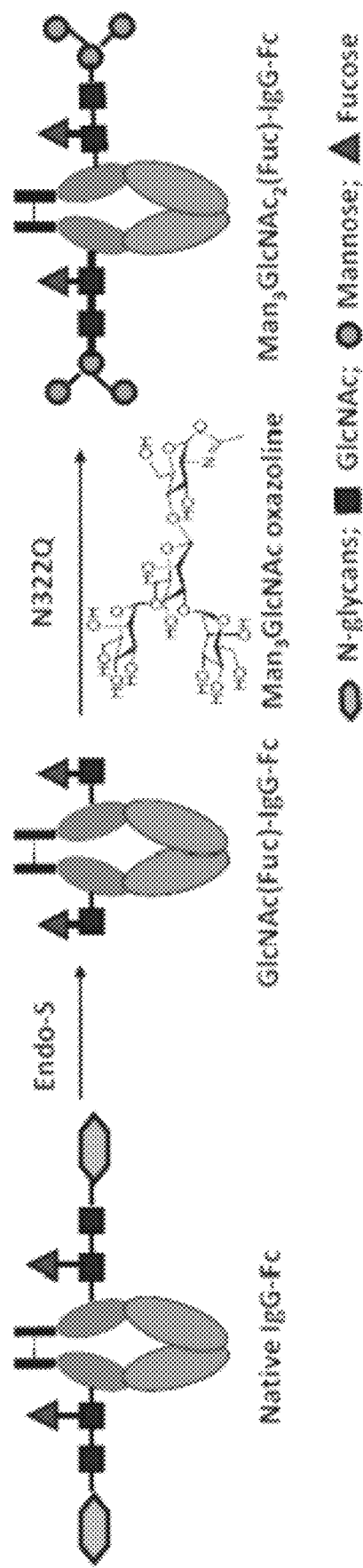
FIG. 23 shows the transglycosylation remodeling of IgG-Fc through transglycosylation with Endo-D mutants.

Commercial rituximab (20 mg) in a Tris-Cl buffer (50 mM, pH 8.0, 2 mL) was incubated with wide-type Endo-S (30 ug) at 37° C. for 1 h. LC-MS and SDS-PAGE analysis indicated the complete cleavage of the N-glycans on the heavy chain. The residue was subjected to an affinity chromatography column of protein A-agarose resin to give the rituximab-GlcNAcFuc (18 mg). LC-MS: calculated for rituximab-GlcNAcFuc heavy chain, M=49420 (J. Chromatography A, 2001, 913, 437-446); found, 49420 (deconvolution). See FIG. 23.

Endo-F3 WT and Mutants Catalyzed Transglycosylation on Rituximab-GlcNAcFuc Using Sialoglycan Oxazoline 12 as Donor Substrate.

A solution of rituximab-GlcNAcFuc (10 mg) and sialoglycan-oxazoline 12 (10 mg) in a Tris buffer (50 mM, pH 7.4, 1 mL) was incubated with the Endo-F3 (500 ug) or Endo-F3 D126A (1 mg) or Endo-F3 D126Q (500 ug) at 30° C. The reactions were monitored by LC-MS. After 5 h, the reaction mixture was subject to an affinity chromatography on a protein A-agarose column following the procedure described above. Fractions containing the product were combined and concentrated by ultracentrifugation to give rituximab-GlcNAcFuc-SCT. LC-MS: calculated for rituximab-GlcNAcFuc-SCT heavy chain, M=51421; found, 51426 (deconvolution). Schematic showing transglycosylation can be viewed in FIG. 23.

Cloning, Expression and Purification of Endo-D in *Escherichia Coli*.

The cDNA fragment encoding the Endo-D fragment (nucleotides 403-3141 (SEQ ID NO: 14); amino acid 135-1047 (as shown in SEQ ID NO: 11)), here called Endo-D, was amplified by PCR from the genomic DNA of *Streptococcus pneumoniae* (ATCC number: BA.A.-334D-5). The forward primer was 5'-TATATA CATATGGAGTCTA.A.ACCAGCAGCAGAAGC-3'(SEQ ID NO: 12), and the reverse primer was 5'-GCGCGC CTCGAGTTCTTCTGTCATCTTTTGGAACGG-3' (SEQ ID NO: 13). NdeI and XhoI site (underlined) were added to the forward and reverse primers, respectively. The cDNA fragment of a further truncated form (nucleotides 475-2471; amino acid 157-807) of Endo-D (called spGH85) was cloned following the previously reported procedure [88]. Both of the amplified DNA fragments were cloned into pET28a (Novagen) after digestion with NdeI and XhoI. The constructed plasmids, pET28a-EndoD and pET28a-spGH85, respectively, were transformed into BL21 (DE3). The transformants were cultured in LB media supplemented with 50 µg/ml kanamycin. Cultures were grown at 37° C. until the cells reached an absorbance of 0.5-0.8 at 600 nm. Then 0.5 mM isopropyl β-D-1-thiogalactopyranoside was added to the culture to induce protein overproduction. After further incubation at 25° C. for 8 h, the cells were harvested by centrifugation. The cell pellets was suspended in a sodium phosphate buffer (50 mM, pH 7.0) with lysozyme before sonication. After sonication and centrifugation, the supernatant from the cell lysis was applied onto $Ni^{2+}$-immobilized HisTrap HP column (GE Healthcare). The column was washed with 50 mM imidazole and then eluted with 200 mM imidazole in a buffer containing 0.5 M NaCl and 0.1 M sodium phosphate (pH 7.4). The eluent was desalted and concentrated by Amicon ultra filtration (10 kDa, Millipore). The homogeneity of the recombinant Endo-D and spGH85 was confirmed by SDS-PAGE with Coomassie Brilliant Blue staining. The protein concentration was quantified using the Bradford assay protocol with bovine serum albumin (BSA) as standards.

Site-Directed Mutagenesis of Endo-D.

The selected mutants (N322A (SEQ ID NO: 8), N322Q (SEQ ID NO: 9), E324Q, Y360F, and H371W all available with changes SEQ ID NO: 11) were generated using the GENEART Site-Directed Mutagenesis Kit (Invitrogen) per the manufacturer's directions. The pET28a-EndoD plasmid encoding the Endo-D gene (nucleotides 403-3141; amino acid 135-1047) was used as the template and LA Taq polymerase (Takara, Japan) was used for PCR. Mutations were confirmed by DNA sequencing and transformed into BL21 (DE3). Expression and purification of mutants were carried out in the same way as for the wild-type enzyme.

Assay for the Transglycosylation Activity of Endo-D and its Mutants.

The transglycosylation activity of the enzyme was assayed as follows: a mixture of $Man_3GlcNAc$-oxazoline (5 mM) and Fmoc-Asn(Fucα1,6GlcNAc)-OH (0.5 mM) or Fmoc-Asn(GlcNAc)-OH (0.5 mM) in a sodium phosphate buffer (50 mM, pH 7.5, 5 µl) containing 10% DMSO was incubated with spGH85 (0.19 µg), Endo-D (0.01 µg), or its mutant (0.01 µg) respectively at 30° C. DMSO was added to enhance the solubility of the Fmoc-Asn(GlcNAc)-OH substrate in the aqueous buffer. Aliquots were taken at intervals and the enzymatic reaction was analyzed by RP-HPLC as described above. The yield of the transglycosylation product was calculated by integration of the peak areas and normalized with the absorbance as follows: transglycosylation yield (%)=[product area/(product area+residual acceptor area)]× 100%.

EndoD-N322Q Mutant-Catalyzed Transglycosylation of Fucα1,6GlcNAc-Fc and $Man_3GlcNAc$ Oxazoline.

A solution of Fucα1,6GlcNAc-Fc (506 µg, 10 nmol) and $Man_3GlcNAc$-oxazoline (138 µg, 200 nmol) in a Tris buffer (50 mM, pH 6.8, 50 µl) was incubated with the N322Q mutant (10 µg) at 30° C. Aliquots were taken at intervals and were analysis by LC-MS. After 5 h, LC-MS indicated the complete reaction of Fucα1,6GlcNAc-Fc to give a new species corresponding to the transglycosylation product (quantitative yield). ESI-MS: calculated for $Man_3GlcNAc$ (α1,6Fuc)GlcNAc-Fc homodimer, M=51951; found (m/z) (deconvoluted data), 51946.

Materials and Methods

The Fmoc-protected amino acids and Fmoc-Ser(tBu)-O-TGT resin were purchased from Novabiochem Corp (San Diego, Calif.). 2-(1-H-Azabenzotriazol-1-yl)-1,1,3,3-tetramethyluronium hexafluorophosphate (HATU) was purchased from GenScript Corp (Piscataway, N.J.). Diisopropylethylamine (DIPEA) was purchased from Applied Biosystems (Carlsbad, Calif.). Piperidine (20% in DMF) was purchased from American Bioanalytical (Natick, Mass.). N,N-Dimethylformamide sequencing grade was purchased from Fisher Biotech (Pittsburgh, Pa.). Acetonitrile HPLC grade was purchased from Fisher Scientific (Pittsburgh, Pa.). 3,4,6-Tri-O-acetyl-1,3-azido-GlcNAc (1) was synthesized following reference [57]. 2,3,4-Tri-O-acetyl-fucose-1α-iodide (4) was synthesized by reported method [58]. $Man_3GlcNAc$ oxazoline (10) was synthesized as reported [42]. The bi-antennary complex-type sialoglycan oxazoline (12) was prepared following the reported procedure [56]. Fmoc-Asn(GlcNAc)-OH (14) was prepared by reported procedure [71]. Endo F1, Endo F2, and Endo F3 were purchased from CalBioChem (San Diego, Calif.). Endo H was purchased from New England Biolabs (Ipswich, Mass.). Endo D was purchased from United States Biological (Swampscott, Mass.). Endo-A was overproduced in *E. coli* and purified following the previously reported procedure [72], using the plasmid pGEX-2T/Endo-A that was kindly provided by Prof Kaoru Takegawa. Endo-M was overproduced according to the previously reported method [52]. PNGase F was purchased from New England Biolabs (Ipswich, Mass.). All other reagents were purchased from Sigma/Aldrich and used as received.

High-Performance Liquid Chromatography (HPLC).

Analytical RP-HPLC was performed on a Waters 626 HPLC instrument with a Symmetry300™ $C_{18}$ column (5.0 µm, 4.6×250 mm) or a XBridge™ BEH130 $C_{18}$ column (3.5 µm, 4.6×250 mm) at 40° C. The Symmetry300 column was eluted with a linear gradient of 0-90% MeCN containing 0.1% TFA within 30 min at a flow rate of 1 mL/min (Method A). The XBridge column was eluted with a linear gradient of 0-20% MeCN containing 0.1% TFA within 30 min at a flow rate of 0.5 mL/min (Method B). Preparative HPLC was performed on a Waters 600 HPLC instrument with a preparative Symmetry300™ $C_{18}$ column (7.0 nm, 19×250 mm) or a XBridge™ Prep ShieldRP18 column (5.0 nm, 10×250 mm). These columns were eluted with a suitable gradient of aqueous acetonitrile containing 0.1% TFA at a flow rate of 12 mL/min (for Symmetry300 column) or 4 mL/min (for XBridge column).

Nuclear Magnet Resonance (NMR).

The $^1$H NMR spectra were measured on JEOL ECX 400 MHz or Inova 500 MHz or Bruker DRX 500 MHz NMR spectrometers. All chemical shifts were assigned in ppm. The $^{13}$C NMR was measured at 125 MHz.

Mass Spectrometry (MS).

The ESI-MS Spectra were measured on a Waters Micromass ZQ-4000 single quadruple mass spectrometer. MALDI-TOF MS measurement was performed on an Autoflex II MALDI-TOF mass spectrometer (Bruker Daltonics). The instrument was calibrated by using ProteoMass Peptide MALDI-MS calibration kit (MSCAL2, Sigma/Aldirich). The matrix used for glycans was 2,5-dihydroxybenzoic acid (DHB) and/or alpha-cyano-4-hydroxycinnamic acid (ACHA) (10 mg/mL in 50% acetonitrile containing 0.1% trifluoroacetic acid). The measuring conditions: 337 nm nitrogen laser with 100 μJ output; laser frequency 50.0 Hz; laser power 30-45%; linear mode; positive polarity; detection range 500-5000; pulsed ion extraction: 70 ns; high voltage: on; realtime smooth: high; shots: 500-2000.

2-Acetamido-3,4-di-O-benzoyl-2-deoxy-6-O-trityl-β-D-glucopyranosyl azide (2)

3,4,6-Tri-O-acetyl-1β-azido-GlcNAc (1) (610 mg, 1.64 mmol) was dissolved in anhydrous MeOH (15 mL) and NaOMe (wt. 25% in MeOH) (2.05 mL, 35.8 mmol) was added. The reaction mixture was stirred for 2 hr under argon. Then it was treated with Dowex 50WX8-100 ion-exchange resin H$^+$ form and filtered. The filtrate was concentrated to dryness under vacuum to give the crude 1β-azido-GlcNAc.

A mixture of the crude 1β-azido-GlcNAc from above, pyridine (10 mL) and trityl chloride (0.91 g, 3.25 mmol) was stirred at 60° C. overnight. Then it was cooled to rt and benzoyl chloride (0.47 mL, 4.06 mmol) was added. The solution was continued to stir at room temperature (rt) overnight. The residue was diluted with EtOAc and washed with 1N HCl, saturated NaHCO$_3$, water, and brine. The organic layer was dried over Na$_2$SO$_4$ and concentrated. The syrup was subject to a silica gel column chromatography eluted with EtOAc:Hexane=1:2 (v/v) to the product 2 as white foam (810 mg, 70%, three steps). $^1$H NMR (400 MHz, CDCl$_3$) δ 7.91 (dd, J=8.24, 0.92 Hz, 2H), 7.65 (dd, J=8.24, 1.36 Hz, 2H), 7.32-7.49 (m, 11H), 7.08-7.16 (m, 10H), 5.84 (d, J=8.72 Hz, 1H), 5.72 (dd, J=10.08, 9.6 Hz, 1H), 5.53 (dd, J=10.56, 10.52 Hz, 1H), 4.78 (d, J=9.16 Hz, 1H), 4.30 (dd, J=10.52, 9.16 Hz, 1H), 3.89 (m, 1H), 3.38 (dd, J=10.56, 2.28 Hz, 1H), 3.16 (dd, J=10.52, 4.12 Hz, 1H), 1.88 (s, 3H). $^{13}$C NMR (100 MHz, CDCl$_3$) δ170.62, 167.17, 164.69, 143.52, 133.77, 133.24, 130.06, 129.66, 129.11, 128.65, 128.31, 127.85, 127.02, 88.59, 86.79, 73.29, 68.75, 62.06, 54.67, 23.35.

2-Acetamido-3,4-di-O-benzoyl-2-deoxy(3D-glucopyranosyl azide (3)

A solution of compound 2 (810 mg, 1.16 mmol) in 80% aqueous AcOH (40 mL) was stirred at 60° C. overnight. Then it was concentrated under vacuum. The residue was diluted with EtOAc and washed with water, brine. The organic layer was dried over Na$_2$SO$_4$ and concentrated. The resulted syrup was subject to a silica gel column chromatography using EtOAc:Hexane=1:1 (v/v) as the eluent to give the product 3 as white foam (410 mg, 78%). $^1$H NMR (400 MHz, CDCl$_3$) δ 7.89-7.92 (m, 4H), 7.48-7.52 (m, 2H), 7.33-7.37 (m, 4H), 6.02 (d, J=9.16 Hz, 1H), 5.78 (dd, J=10.56, 9.16 Hz, 1H), 5.50 (dd, J=10.08, 9.64 Hz, 1H), 4.97 (d, J=9.16 Hz, 1H), 4.17 (dt, J=10.52, 9.16 Hz, 1H), 3.84-3.89 (m, 2H), 3.73 (dd, J=12.84, 4.6 Hz, 1H), 1.89 (s, 3H). $^{13}$C NMR (100 MHz, CDCl$_3$) δ170.76, 166.80, 166.01, 133.86, 133.80, 129.94, 128.63, 128.54, 88.76, 77.43, 72.55, 69.08, 61.31, 54.61, 23.29.

2-Acetamido-3,4-di-O-benzoyl-2-deoxy-6-O-(α-L-fucopyranosyl)-β-D-glucopyranosyl azide (5)

To a stirring solution of tetra-O-Trimethylsilyl-α-L-fucopyranoside (1.23 g, 2.72 mmol) in anhydrous CH$_2$Cl$_2$ (8 mL), iodotrimethylsilane (0.37 mL, 2.72 mmol) was added and the mixture was stirred at rt for 20 min to give the 2,3,4-Tri-O-acetyl-fucose-iodide (4) in situ. Then, a solution of compound 3 (0.62 g, 1.34 mmol) and 2,6-di-tert-butylpyridine (0.6 mL, 2.72 mmol) in anhydrous CH$_2$Cl$_2$ (7 mL) was added to the reaction and the mixture was stirred at rt for 5 h. MeOH (5 mL) was added to remove the TMS group and the reaction solution was stirred for additional 20 min. Then it was treated with Dowex 1X2-100 ion-exchange resin Off form and filtered. The filtrate was concentrated under vacuum and the residue was subject to a silica gel column chromatography using CH$_2$Cl$_2$:MeOH=15:1 (v/v) as the eluent to give the product 5 as a white solid (0.5 g, 61%). $^1$H NMR (400 MHz, CDCl$_3$) δ 7.86-7.89 (m, 4H), 7.48 (dt, J=7.32, 1.36 Hz, 2H), 7.25-7.34 (m, 4H), 6.30 (d, J=8.72 Hz, 1H), 5.68-5.75 (m, 2H), 4.93 (d, J=9.64 Hz, 1H), 4.82 (d, J=3.68 Hz, 1H), 4.22 (dd, J=10.08, 9.16 Hz, 1H), 4.09 (dd, J=13.28, 6.4 Hz, 1H), 3.94-4.04 (m, 2H), 3.78-3.84 (m, 2H), 3.58 (dd, J=11.48, 3.68 Hz, 1H), 3.46 (broad s, 1H), 3.10 (d, J=10.52 Hz, 1H), 2.90 (broad s, 1H), 1.87 (s, 3H), 1.26 (d, J=6.44 Hz, 3H). $^{13}$C NMR (100 MHz, CDCl$_3$) δ170.96, 166.83, 165.86, 133.98, 133.84, 129.92, 128.65, 128.50, 128.46, 98.44, 88.44, 75.10, 72.64, 71.76, 71.51, 69.49, 68.58, 66.45, 65.05, 54.5, 23.24, 16.20.

2-Acetamido-3,4-di-O-acetyl-2-deoxy-6-O-(tri-O-acetyl-α-L-fucopyranosyl)-β-D-glucopyranosyl azide (6)

A solution of compound 5 (0.5 g, 0.83 mmol) and 0.5 M NaOMe in MeOH (50 μL, 50 μmol) in anhydrous MeOH/THF (1/1, v/v, 20 mL) was stirred at rt under argon for 1 hr. The reaction mixture was treated with Dowex 50WX8-100 ion-exchange resin H form and filtered. The filtrate was concentrated to dryness under vacuum. Pyridine (5 mL) and Ac$_2$O (5 mL) were added to the residue and the mixture was stirred at rt overnight. Then it was diluted with EtOAc and washed with saturated NaHCO$_3$, water, and brine. The organic layer was dried over Na$_2$SO$_4$ and concentrated under vacuum. The residue was subject to a silica gel column chromatography using EtOAc as the eluent to give the product 6 as a white solid (0.46 g, 92%). $^1$H NMR (400 MHz, CDCl$_3$) δ 5.72 (d, J=8.68 Hz, 1H), 5.28-5.33 (m, 2H), 5.24 (dd, J=10.52, 9.16 Hz, 1H), 5.03-5.10 (m, 3H), 4.75 (d, J=9.64 Hz, 1H), 4.16 (dt, J=6.88, 6.4 Hz, 1H), 3.86 (dt, J=10.52, 9.2 Hz, 1H), 3.71-3.79 (m, 2H), 3.51 (dd, J=11.48, 5.04 Hz, 1H), 2.14 (s, 3H), 2.08 (s, 3H), 2.02 (s, 3H), 2.01 (s, 3H), 1.97 (s, 3H), 1.96 (s, 3H), 1.12 (d, J=6.4 Hz, 3H). $^{13}$C NMR (100 MHz, CDCl$_3$) δ68.59, 68.04, 68.00, 66.36, 64.64, 54.33, 23.34, 20.82, 20.79, 20.72 (2C), 20.70, 15.96.

N$^\omega$-(2-Acetamido-3,4-di-O-acetyl-2-deoxy-6-O-(tri-O-acetyl-α-L-fucopyranosyl)-N$^\alpha$-(9-fluorenylmethyloxycarbonyl)-L-asparagine tert-butyl ester (7)

To a solution of compound 6 (0.46 g, 0.76 mmol) in THF (10 mL) was slowly added 1.0 M trimethylphosphine in toluene (1.15 mL, 1.15 mmol) and the mixture was stirred at rt for 2 h until TLC showed the reaction is complete. The solvent was removed under vacuum and the residue was dissolved in DMF (2 mL). Then, $N^\alpha$-(9-Fluorenylmethyl-oxycarbonyl)-L-aspatic acid α-tert-butyl ester (350 mg, 0.85 mmol), HATU (0.5 M in DMF, 4.5 mL, 2.25 mmol), and DIPEA (1.0 M in DMF, 3.0 mL, 3.0 mmol) were added and the mixture was stirred at rt overnight under argon protection. The reaction solution was diluted with EtOAc and washed with water and brine. The organic layer was dried over $Na_2SO_4$ and concentrated to dryness under vacuum. The residue was subject to a silica gel column chromatography using EtOAc as the eluent to give the product 7 as a white solid (570 mg, 77%, two steps). $^1$H NMR (400 MHz, $CDCl_3$) δ 7.73 (d, J=7.8 Hz, 2H), 7.63 (t, J=7.32 Hz, 2H), 7.36 (t, J=7.8 Hz, 2H), 7.26-7.31 (m, 2H), 7.15 (broad d, J=8.24 Hz, 1H), 6.35 (d, J=9.16 Hz, 1H), 5.93 (d, J=7.76 Hz, 1H), 5.34 (dd, J=11, 3.64 Hz, 1H), 5.26 (d, J=2.72 Hz, 1H), 5.16 (dd, J=10.96, 3.68 Hz, 1H), 4.98-5.06 (m, 4H), 4.96 (dd, J=9.6, 8.24 Hz, 1H), 4.53 (m, 1H), 4.37 (dd, J=10.52, 7.8 z, 1H), 4.32 (dd, J=10.08, 7.36 Hz, 1H), 4.24 (t, J=7.32 Hz, 1H), 4.06 (dt, J=9.6, 8.24 Hz, 1H), 3.68 (m, 1H), 3.52 (dd, J=11.92, 5.04 Hz, 1H), 2.87 (dd, J=16.52, 4.6 Hz, 1H), 2.68 (dd, J=16.48, 3.64 Hz, 1H), 2.12 (s, 3H), 2.04 (s, 3H), 2.03 (s, 3H), 1.96 (s, 9H), 1.93 (s, 3H), 1.42 (s, 9H), 1.07 (d, J=6.44 Hz, 3H). $^{13}$C NMR (100 MHz, $CDCl_3$) δ172.32, 172.11, 171.17, 170.93, 170.71, 170.25, 170.10, 169.32, 156.56, 144.10, 141.31, 127.69, 127.19, 127.14, 125.46, 125.42, 119.98, 96.84, 82.00, 75.25, 73.13, 71.15, 68.30, 68.02, 67.79, 67.25, 65.47, 64.66, 53.44, 50.94, 47.19, 38.69, 38.03, 27.99 (3C), 23.16, 20.89, 20.81, 20.79, 20.72, 20.56, 15.92.

$N^\omega$-(2-Acetamido-3,4-di-O-acetyl-2-deoxy-6-O-(tri-O-acetyl-α-L-fucopyranosyl)-N''-(9-fluorenylmethyloxycarbonyl)-L-asparagine (8)

Compound 7 (100 mg, 0.1 mmol) was dissolved in 20% TFA in $CH_2Cl_2$ (2 mL) and the mixture was stirred at room temperature for 1 h. The residue was co-evaporated with toluene (3 mL) under vacuum and the resulted white solid was washed with $Et_2O$ (5 mL) to give the pure product 8 (90 mg, 95%). $^1$H NMR (400 MHz, $CDCl_3$) δ 8.58 (d, J=9.2 Hz, 1H, 1-NH of GlcNAc), 7.84 (m, 3H, 2-NHAc of GlcNAc, Ar—H), 7.68 (d, J=7.6 Hz, 2H, Ar—H), 7.45 (d, J=8.8 Hz, 1H, FmocNH), 7.38 (m, 2H, Ar—H), 7.28 (m, 2H, Ar—H), 5.19-5.15 (m, 3H, H1 of GlcNAc, H3 and H4 of Fuc), 5.03 (t, J=9.6 Hz, 1H, H3 of GlcNAc), 4.91-4.80 (m, 3H, H1 and H2 of Fuc, H4 of GlcNAc), 4.34 (dd, J=7.2, 13.2 Hz, □H of Asn), 4.26-4.15 (m, 4H, H5 of Fuc, $CH_2$ and H9 of Fmoc), 3.86 (q, J=9.6 Hz, 1H, H2 of GlcNAc), 3.66 (m, 2H, H5 and H6a of GlcNAc), 3.45 (m, 1H, H6b of GlcNAc), 2.65-2.49 (m, 2H, □H of Asn), 2.06 (s, 3H, Ac), 1.99 (s, 3H, Ac), 1.93 (s, 3H, Ac), 1.93 (s, 3H, Ac), 1.90 (s, 3H, Ac), 1.86 (s, 3H, Ac), 1.68 (s, 3H, NHAc), 0.98 (d, J=6.8 Hz, 1H, $CH_3$ of Fuc); $^{13}$C NMR (100 MHz, $CDCl_3$) δ173.5, 170.8, 170.6, 170.3, 170.2, 170.1, 169.9, 169.7, 156.3, 144.3, 141.2, 128.1, 127.6, 125.8, 120.6, 96.5, 78.5, 74.2, 74.0, 71.1, 69.2, 67.9, 67.6, 66.4, 66.2, 64.5, 52.5, 50.5, 47.1, 37.4, 23.1, 21.0, 20.9, 20.8, 16.0. ESI-MS: calculated for $C_{43}H_{51}N_3O_{19}$, M=913.31, found, 914.47 $[M+H]^+$.

$N^\omega$-(2-Acetamido-6-O-(α-L-fucopyranosyl)-N''-(9-fluorenylmethyloxycarbonyl)-L-asparagine (9)

A mixture of compound 8 (90 mg, 0.1 mmol), $K_2CO_3$ (87 mg, 0.63 mmol), and MeOH/THF (3/1, 4 mL) was stirred at room temperature. The reaction was carefully monitored by ESI-MS until the acetyl groups were selectively hydrolyzed. Then 1N HCl was added to neutralize the solution to be pH 2-3. The residue was subject to a preparative HPLC for purification. The product 9 was obtained as a white solid (60 mg, 85%). $^1$H NMR (400 MHz, DMSO-$d_6$+1% $D_2O$) δ 8.20 (broad d, J=9.16 Hz, 1H), 7.85 (d, J=7.8 Hz, 2H), 7.67 (d, J=5.92 Hz, 2H), 7.39 (t, J=7.8 Hz, 2H), 7.30 (t, J=7.32 Hz, 2H), 4.80 (dd, J=9.2, 6.44 Hz, 1H), 4.59 (d, J=3.2 Hz, 1H), 4.31 (dd, J=7.8, 5.52 Hz, 1H), 4.15-4.25 (m, 3H), 3.83 (dd, J=13.28, 6.4 Hz, 1H), 3.44-3.54 (m, 6H), 3.30 (dd, J=9.64, 9.16 Hz, 2H), 3.09 (t, J=9.16 Hz, 1H), 2.57 (dd, J=16.04, 5.04 Hz, 1H), 2.44 (dd, J=16.04, 7.32 Hz, 1H), 1.74 (s, 3H), 1.03 (d, J=6.88 Hz, 3H). $^{13}$C NMR (100 MHz, DMSO-$d_6$+1% $D_2O$) δ173.38, 171.71, 170.33, 156.56, 144.10, 144.05, 141.12, 128.33, 127.75, 125.70, 120.61, 100.03, 78.96, 77.33, 74.29, 71.95, 70.58, 69.91, 68.51, 67.95, 66.46, 66.38, 54.82, 50.5, 46.98, 37.19, 23.03, 16.81. ESI-MS: calculated for $C_{33}H_{41}N_3O_{14}$, M=703.25, found, 702.31 $[M-H]^-$.

Chemoenzymatic Transglycosylation Assay of Various Endoglycosidases Using $Man_3GlcNAc$ Oxazoline (10) as Donor Substrate and Fmoc-Asn(Fucα1,6GlcNAc)-OH (9) as Acceptor Substrate.

A mixture of acceptor 9 (25 μg, 36 nmol) and $Man_3GlcNAc$ oxazoline (100 μg, 145 nmol) in a phosphate buffer (50 mM, pH 7.0, 12 μL) was incubated at 30° C. with individual Endo-β-N-acetylglucosaminidase (4 μg). The reaction was monitored by analytic HPLC by taking reaction aliquots at 10 min, 20 min, 30 min, 1 h, 2 h, 4 h and 20 h. The yields were calculated based on the peak area of product and starting material acceptor. Total 7 ENGases, including Endo-F1, Endo-F2, Endo-F3, Endo-A, Endo-M, Endo-D, and Endo-H, were measured for their transglycosylation activity in this assay. The time-course results are shown in FIG. 3. Panel A. The product was purified by RP-HPLC to give Fmoc-Asn($Man_3GlcNAc_2Fuc$)-OH (11). $t_R$=16.8 min (analytical HPLC, method A). MALDI-TOF MS: Calculated for $C_{59}H_{84}N_4O_{34}$, M=1392.50; found, 1416.12 [M+Na]; ESI-MS: found 1393.58 $[M+H]^+$, 1247.60 $[M-Fuc+H]^+$, 1085.43 $[M-Fuc-Man+H]^+$, 923.45 $[M-Fuc-2Man+H]^+$, 761.39 $[M-Fuc-3Man+H]^+$.

Endo-D Digestion of Compound 11.

A solution of 11 (10 μg) in a phosphate butter (50 mM, pH 7.0, 20 μL) was incubated with Endo-D (1 μg) at 30° C. for 2 h. The digestion was monitored by RP-HPLC combined with ESI-MS analysis. It clearly showed the compound 11 disappeared and a new peak emerged in the same position of Fmoc-Asn(Fucα1,6GlcNAc)-OH which was confirmed by ESI-MS analysis. This digestion data validated the β1,4-linkage of N,N'-diacetylchitobiose unit in compound 11.

Chemoenzymatic Transglycosylation Assay of Various Endo-Glycosidases Using Complex-Type Sialoglycan Oxazoline (12) as Donor Substrate and Fmoc-Asn(Fucα1, 6GlcNAc)-OH (9) as Acceptor Substrate.

A mixture of acceptor 9 (25 μg, 36 nmol) and sialoglycan oxazoline 12 (290 μg, 145 nmol) in phosphate buffer (50 mM, pH 7.0, 12 μL) was incubated at 30° C. with individual Endo-β-N-acetylglucosaminidase (4 μg). The reaction was monitored by analytic HPLC by taking reaction aliquots at 10 min, 20 min, 30 min, 1 h, 2 h, 4 h and 20 h. The yields were calculated based on the peak area of product and starting material acceptor. Total 7 ENGases, including Endo-F1, Endo-F2, Endo-F3, Endo-A, Endo-M, Endo-D, and Endo-H, were measured for their transglycosylation activity in this assay. The time-course results are shown in FIG. 3. Panel B. The product was purified by RP-HPLC to give Fmoc-Asn(Sia$_2$Gal$_2$GlcNAc$_2$Man$_3$GlcNAc$_2$Fuc)-OH (13). t$_R$=16.3 min (analytical HPLC, method A). MALDI-TOF MS: Calculated for C$_{107}$H$_{161}$N$_7$O$_{69}$, M=2704.95; found, 2728.48 [M+Na]$^+$; ESI-MS: found 1353.98 [M+2H]$^{2+}$, 1208.19 [M−Sia+2H]$^{2+}$.

Endo-F3 Digestion of Compound 13.

A solution of 13 (10 μg) in a phosphate butter (50 mM, pH 7.0, 20 μL) was incubated with Endo-F3 (2 μg) at 30° C. for 20 h. The digestion was monitored by RP-HPLC combined with ESI-MS analysis. It clearly showed the compound 13 disappeared and a new peak emerged in the same position of Fmoc-Asn(Fucα1,6GlcNAc)-OH and was confirmed by the ESI-MS. This digestion data validated the β1,4-linkage of N,N'-diacetylchitobiose unit in compound 13.

Chemoenzymatic Transglycosylation Assay of Various Endo-Glycosidases Using Man$_3$GlcNAc Oxazoline (10) as Donor Substrate and Fmoc-Asn(GlcNAc)-OH (14) as Acceptor Substrate.

A mixture of acceptor 14 (20 μg, 36 nmol) and Man$_3$GlcNAc oxazoline (100 μg, 145 nmol) in phosphate buffer (50 mM, pH 7.0, 12 μL) was incubated at 30° C. with individual Endo-β-N-acetylglucosaminidase (4 μg). The reaction was monitored by analytic HPLC by taking reaction aliquots at 10 min, 20 min, 30 min, 1 h, 2 h, 4 h and 20 h. The yields were calculated based on the peak area of product and starting material acceptor. Total 4 ENGases, including Endo-F1, Endo-F2, Endo-F3, and Endo-D, were measured for their transglycosylation activity in this assay. The time-course results are shown in FIG. 6. The product was purified by RP-HPLC to give Fmoc-Asn(Man$_3$GlcNAc$_2$)—OH (15). t$_R$=17.0 min (analytical HPLC, method A). MALDI-TOF MS: Calculated for C$_{53}$H$_{74}$N$_4$O$_{30}$, M=1246.44; found, 1270.25 [M+Na]$^+$; ESI-MS: found 1247.68 [M+H]$^+$.

Endo-M Digestion of Compound 15.

A solution of 15 (10 μg) in a phosphate butter (50 mM, pH 7.0, 20 μL) was incubated with Endo-M (1 μg) at 30° C. for 2 h. The digestion was monitored by RP-HPLC combined with ESI-MS analysis. It clearly showed the compound 15 disappeared and a new peak emerged in the same position of Fmoc-Asn(GlcNAc)-OH and was confirmed by the ESI-MS. This digestion data validated the β1,4-linkage of N,N'-diacetylchitobiose unit in compound 15.

Solid-Phase Synthesis of the CD52 Peptide Bearing Fucα1-6GlcNAc (17).

The CD52 peptide was synthesized manually by the Fmoc-chemistry using Fmoc-protected amino acid derivatives. An O-link TGT resin (Novabiochem Corp) was used as the solid support, in which the first amino acid (Ser) was attached through the acid-labile ester linkage. To introduce a Fucα1-6GlcNAc residue at the N-glycosylation site, Fmoc-Asn(Ac$_5$Fucα1-6GlcNAc)-OH (8) was used as building blocks to replace the residues at Asn-3 in the solid-phase peptide synthesis. HATU (0.5 M in DMF) and DIPEA (1.0 M in DMF) (1:1, v/v) were used as the coupling activator and piperidine (20% in DMF) was used as the deblocking reagent. Synthesis was carried out on a 10 μmol scale and 4-fold excess of Fmoc-protected building blocks were used for each coupling reaction cycle. The N-terminus amino group was protected with acetyl group by treatment with Ac$_2$O/DIPEA. The resulted resin (16) was cleaved by treatment with TFA/CH$_2$Cl$_2$ (1/4, v/v) at r.t. for 5 h to release the crude peptide and simultaneously remove the protecting groups of Trt and t-Bu. The Ac groups on the disaccharide were removed by treatment with 5% aqueous hydrazine at rt for 1 h. The residue was subject to preparative HPLC purification to give the peptide CD52-Fucα1-6GlcNAc (17) as a white powder (14.4 mg, overall yield 90%). Analytical HPLC of 17 (Method B): t$_R$=23.8 min; $^1$H NMR (D$_2$O, 400 MHz): δ 4.91 (d, J=9.6 Hz, 1H, H1 of GlcNAc), 4.76 (d, J=3.6 Hz, 1H, H1 of Fuc), 4.71-4.58 (m, 3H, αH of Ser, □H of Asn), 4.39-4.25 (m, 7H, αH of Ser×3, αH of Pro, αH of Gln×2, αH of Thr), 4.19-4.10 (m, 3H, αH of Thr, αH of Thr×2), 3.99 (q, J=6.8 Hz, 1H, H5 of Fuc), 3.86-3.60 (m, 18H), 3.52-3.38 (m, 3H), 2.82-2.64 (m, 4H, αH of Asn×2, αH of Asp×2), 2.27-2.15 (m, 5H, Gln-H, Pro-H), 2.08-1.82 (m, 13H, Ac, Gln-H, Pro-H), 1.08 (m, 9H, Thr-CH$_3$×2, Fuc-CH$_3$); $^1$H-$^{13}$C HSQC NMR ($^{13}$C 125 MHz, $^1$H 500 MHz, D$_2$O) δ 4.91/78.4 (GlcNAc-1), 4.76/99.2 (Fuc-1), 4.69/53.1 (Ser-α), 4.68/49.8 (Asp-α), 4.60/49.6 (Asn-α), 4.39/56.1 (Ser-αα), 4.35/61.8 (Pro-α), 4.31/56.3 (Ser-α), 4.30/56.0 (Gln-α), 4.28/53.3 (Gln-α), 4.26/58.9 (Ser-α), 4.25/59.1 (Thr-α), 4.18/53.5 (Thr-α), 4.16/67.8 (Thr-β), 4.13/67.9 (Thr-β), 3.99/67.5 (Fuc-5), 3.85/68.3 (GlcNAc-6), 3.64/68.3 (GlcNAc-6), 2.80/35.8 (Asn-β), 2.74/36.4 (Asp-β), 2.25/31.4 (Gln-β), 2.21/30.7 (Pro), 2.02/22.1 (Ac), 1.95/22.8 (Ac), 1.89/30.6 (Pro), 1.83/27.2 (Ac), 1.10/16.2 (Thr-CH$_3$), 1.08/19.7 (Fuc-CH$_3$), 1.06/16.2 (Thr-CH$_3$); MALDI-TOF MS: Calculated for C$_{61}$H$_{98}$N$_{16}$O$_{34}$, M=1598.64; found, 1622.32 [M+Na]$^+$; ESI-MS: 1599.16 [M+H]$^+$, 800.27 [M+2H]$^{2+}$.

Chemoenzymatic Synthesis of Sialylated and Core-Fucosylated Complex-Type Glycoform of CD52 (18).

A mixture of CD52 peptide 17 (2 mg, 1.25 μmol) and sialoglycan oxazoline 12 (5 mg, 2.5 μL) in phosphate buffer (50 mM, pH 7.0, 250 μL) was incubated at 30° C. with Endo-F3 (80 μg) for 1 h. The reaction was quenched with 1% TFA (10 μL) and the residue was subject to preparative RP-HPLC to give CD52-Sia$_2$Gal$_2$GlcNAc$_2$Man$_3$GlcNAc$_2$Fuc (18) as a white powder (2.5 mg, 55%). t$_R$=21.5 min (analytical HPLC, method B). $^1$H NMR (D$_2$O, 400 MHz): δ 5.00 (s, 1H, H1 of Man$^4$), 4.89 (d, J=9.6 Hz, 1H, H1 of GlcNAc$^1$), 4.81 (s, 1H, H1 of Man$^{4'}$), 4.75 (s, 1H, H1 of Fuc), 4.72-4.58 (m, 4H, αH of Ser, H1 of Man$^3$, αH of Asp, αH of Asn), 4.56 (d, J=7.6 Hz, H1 of GlcNAc$^2$), 4.48 (d, J=7.2 Hz, H1 of GlcNAc$^5$, H1 of GlcNAc$^{5'}$), 4.41-4.24 (m, 9H, αH of Ser×3, αH of Pro, αH of Gln×2, H1 of Gal$^6$, H1 of Gal$^{6'}$, αH of Thr), 4.18-4.14 (m, 3H, αH of Thr, αH of Thr×2), 4.12 (m, 1H), 4.07 (m, 1H), 3.98 (m, 2H), 3.89-3.35 (m, 82H), 2.87-2.61 (m, 4H, αH of Asn×2, αH of Asp×2), 2.54 (m, 2H, H3$_{ax}$ of Sia×2), 2.27-2.18 (m, 5H, Gln-H, Pro-H), 2.07-1.83 (m, 29H, Ac, Gln-H, Pro-H), 1.60 (t, J=12.0 Hz, 2H, H3$_{eq}$ of Sia×2), 1.07 (m, 9H, Thr-CH$_3$×2, Fuc-CH$_3$); $^1$H-$^{13}$C HSQC NMR ($^{13}$C 125 MHz, $^1$H 500 MHz, D$_2$O) δ 5.00/99.6 (Man$^4$-1), 4.89/78.7 (GlcNAc$^1$-1), 4.81/97.5 (Man$^{4'}$-1), 4.75/99.8 (Fuc-1), 4.68/54.4 (Ser-α), 4.66/51.3 (Asp-α), 4.65/101.3 (Man$^3$-1), 4.59/51.5 (Asn-α), 4.56/101.7 (GlcNAc$^2$-1), 4.48/100.1 (GlcNAc$^5$-1, GlcNAc$^{5'}$-1), 4.38/56.3 (Ser-α), 4.35/61.5 (Pro-α), 4.31/56.8 (Ser-α), 4.31/56.3 (Gln-α), 4.30/104.4 (Gal$^6$-1, Gal$^{6'}$-1), 4.27/53.7 (Gln-α), 4.26/59.8 (Ser-α), 4.24/60.1 (Thr-α), 4.18/54.2 (Thr-α), 4.15/67.8 (Thr-β), 4.13/67.8 (Thr-β), 3.98/67.5 (Fuc-5), 2.83/35.8 (Asn-β), 2.74/36.2 (Asp-β), 2.54/40.3 (Sia-3$_{ax}$), 2.25/31.3 (Gln-β), 2.02/22.3 (Ac), 1.95/22.4 (Ac), 1.87/26.8 (Ac), 1.60/40.3 (Sia-3$_{eq}$), 1.08/15.9 (Thr-CH$_3$), 1.07/19.7 (Fuc-CH$_3$), 1.05/15.9 (Thr-CH$_3$); ESI-MS: Calculated for C$_{137}$H$_{221}$N$_{21}$O$_{90}$, M=3600.34; found 1201.66 [M+3H]$^{3+}$.

Chemoenzymatic Synthesis of Sialylated and Core-Fucosylated Complex-Type Glycoform of CD52 (18) by Transglycosylation with Endo-F3 Mutant, D126A.

A mixture of CD52 peptide 17 and sialoglycan oxazoline 12 in phosphate buffer (50 mM, pH 7.5) was incubated at 30° C. with Endo-F3 mutant D126A (SEQ ID NO: 6), following the above described procedures, giving the transglycosylation product with over 90% yield. The product was isolated by RP-HPLC and characterized as described above.

Endo-F3 Digestion of CD52 Glycopeptide 18.

A solution of 18 (20 µg) in a phosphate butter (50 mM, pH 7.0, 20 µL) was incubated with Endo-F3 (2 µg) at 30° C. for 20 h. The digestion was monitored by RP-HPLC combined with ESI-MS analysis. It was clearly shown that the glycopeptide 18 peak disappeared and a new peak emerged in the same position as CD52-Fucα1,6GlcNAc and was confirmed by the ESI-MS. This digestion experiment validated the α1,4-linkage of N,N'-diacetylchitobiose unit in compound 18.

PNGase F Digestion of CD52 Glycopeptide 18.

A solution of 18 (20 µg) in a phosphate buffer (50 mM, pH 7.5, 20 µL) was incubated at 37° C. with PNGase F (500 U) for 4 h. The reaction mixture was subject to analytic RP-HPLC. The released sialoglycan 19 and Asp-CD52 20 was purified and characterized by ESI-MS (FIG. 11). Sialoglycan 19: analytical HPLC (Method B): $t_R$=17.8 min; ESI-MS: calculated for $C_{90}H_{148}N_6O_{66}$, M=2368.84 Da; found (m/z), 1185.82 $[M+2H]^{2+}$, 1040.41 $[M-Sia+2H]^{2+}$. Asp-CD52 20: analytical HPLC Method B: $t_R$=24.2 min; ESI-MS: calculated for $C_{47}H_{74}N_{14}O_{26}$, M=1250.49 Da; found (m/z), 1251.56 $[M+H]^+$, 626.38 $[M+2H]^{2+}$.

REFERENCES

The contents of all references cited herein are hereby incorporated by reference herein for all purposes.
1. A. Varki, *Glycobiology*, 1993, 3, 97-130.
2. R. A. Dwek, *Chem. Rev.*, 1996, 96, 683-720.
3. A. Helenius and M. Aebi, *Science*, 2001, 291, 2364-2369.
4. R. S. Haltiwanger and J. B. Lowe, *Annu Rev Biochem*, 2004, 73, 491-537.
5. D. H. Dube and C. R. Bertozzi, *Nat Rev Drug Discov*, 2005, 4, 477-488.
6. J. N. Arnold, M. R. Wormald, R. B. Sim, P. M. Rudd and R. A. Dwek, *Annu Rev Immunol*, 2007, 25, 21-50.
7. R. A. Dwek, T. D. Butters, F. M. Platt and N. Zitzmann, *Nat Rev Drug Discov*, 2002, 1, 65-75.
8. R. Jefferis, *Biotechnol. Prog.*, 2005, 21, 11-16.
9. G. Walsh and R. Jefferis, *Nat. Biotechnol.*, 2006, 24, 1241-1252.
10. Y. Kaneko, F. Nimmerjahn and J. V. Ravetch, *Science*, 2006, 313, 670-673.
11. R. M. Anthony, F. Nimmerjahn, D. J. Ashline, V. N. Reinhold, J. C. Paulson and J. V. Ravetch, *Science*, 2008, 320, 373-376.
12. S. Andre, T. Kozar, S. Kojima, C. Unverzagt and H. J. Gabius, *Biol Chem*, 2009, 390, 557-565.
13. S. Andre, T. Kozar, R. Schuberth, C. Unverzagt, S. Kojima and H. J. Gabius, *Biochemistry*, 2007, 46, 6984-6995.
14. C. Unverzagt, S. Andre, J. Seifert, S. Kojima, C. Fink, G. Srikrishna, H. Freeze, K. Kayser and H. J. Gabius, *J Med Chem*, 2002, 45, 478-491.
15. R. Niwa, E. Shoji-Hosaka, M. Sakurada, T. Shinkawa, K. Uchida, K. Nakamura, K. Matsushima, R. Ueda, N. Hanai and K. Shitara, *Cancer Res*, 2004, 64, 2127-2133.
16. T. Shinkawa, K. Nakamura, N. Yamane, E. Shoji-Hosaka, Y. Kanda, M. Sakurada, K. Uchida, H. Anazawa, M. Satoh, M. Yamasaki, N. Hanai and K. Shitara, *J Biol Chem*, 2003, 278, 3466-3473.
17. R. L. Shields, J. Lai, R. Keck, L. Y. O'Connell, K. Hong, Y. G. Meng, S. H. Weikert and L. G. Presta, *J Biol Chem*, 2002, 277, 26733-26740.
18. S. Barrabes, L. Pages-Pons, C. M. Radcliffe, G. Tabares, E. Fort, L. Royle, D. J. Harvey, M. Moenner, R. A. Dwek, P. M. Rudd, R. De Llorens and R. Peracaula, *Glycobiology*, 2007, 17, 388-400.
19. M. Takahashi, Y. Kuroki, K. Ohtsubo and N. Taniguchi, *Carbohydr Res*, 2009, 344, 1387-1390.
20. D. Osumi, M. Takahashi, E. Miyoshi, S. Yokoe, S. H. Lee, K. Noda, S, Nakamori, J. Gu, Y. Ikeda, Y. Kuroki, K. Sengoku, M. Ishikawa and N. Taniguchi, *Cancer Sci*, 2009, 100, 888-895.
21. M. A. Comunale, M. Wang, J. Hafner, J. Krakover, L. Rodemich, B. Kopenhaver, R. E. Long, O. Junaidi, A. M. Bisceglie, T. M. Block and A. S. Mehta, *J Proteome Res*, 2009, 8, 595-602.
22. M. J. Grogan, M. R. Pratt, L. A. Marcaurelle and C. R. Bertozzi, *Annu. Rev. Biochem.*, 2002, 71, 593-634.
23. T. Buskas, S. Ingale and G. J. Boons, *Glycobiology*, 2006, 16, 113R-136R.
24. C. S. Bennett and C. H. Wong, *Chem. Soc. Rev.*, 2007, 36, 1227-1238.
25. D. P. Gamblin, E. M. Scanlan and B. G. Davis, *Chem. Rev.*, 2009, 109, 131-163.
26. G. J. Bernardes, B. Castagner and P. H. Seeberger, *ACS Chem Biol*, 2009, 4, 703-713.
27. J. R. Rich and S. G. Withers, *Nat Chem Biol*, 2009, 5, 206-215.
28. D. Macmillan and C. R. Bertozzi, *Angew. Chem. Int. Ed.*, 2004, 43, 1355-1359.
29. N. Yamamoto, Y. Tanabe, R. Okamoto, P. E. Dawson and Y. Kajihara, *J. Am. Chem. Soc.*, 2008, 130, 501-510.
30. C. Piontek, P. Ring, O. Harjes, C. Heinlein, S. Mezzato, N. Lombana, C. Pohner, M. Puttner, D. Varon Silva, A. Martin, F. X. Schmid and C. Unverzagt, *Angew. Chem. Int. Ed.*, 2009, 48, 1936-1940.
31. C. Piontek, D. Varon Silva, C. Heinlein, C. Pohner, S. Mezzato, P. Ring, A. Martin, F. X. Schmid and C. Unverzagt, *Angew. Chem. Int. Ed.*, 2009, 48, 1941-1945.
32. S. I. van Kasteren, H. B. Kramer, H. H. Jensen, S. J. Campbell, J. Kirkpatrick, N.J. Oldham, D. C. Anthony and B. G. Davis, *Nature*, 2007, 446, 1105-1109.
33. K. Hirano, D. Macmillan, K. Tezuka, T. Tsuji and Y. Kajihara, *Angew. Chem. Int. Ed.*, 2009, 48, 9557-9560.
34. S. R. Hamilton, P. Bobrowicz, B. Bobrowicz, R. C. Davidson, H. Li, T. Mitchell, J. H. Nett, S. Rausch, T. A. Stadheim, H. Wischnewski, S. Wildt and T. U. Gerngross, *Science*, 2003, 301, 1244-1246.
35. S. Wildt and T. U. Gerngross, *Nat. Rev. Microbiol.*, 2005, 3, 119-128.
36. S. R. Hamilton, R. C. Davidson, N. Sethuraman, J. H. Nett, Y. Jiang, S. Rios, P. Bobrowicz, T. A. Stadheim, H. Li, B. K. Choi, D. Hopkins, H. Wischnewski, J. Roser, T. Mitchell, R. R. Strawbridge, J. Hoopes, S. Wildt and T. U. Gerngross, *Science*, 2006, 313, 1441-1443.
37. S. Eller, R. Schuberth, G. Gundel, J. Seifert and C. Unverzagt, *Angew. Chem. Int. Ed.*, 2007, 46, 4173-4175.
38. B. Sun, B. Srinivasan and X. Huang, *Chemistry*, 2008, 14, 7072-7081.
39. K. Yamamoto, *J. Biosci. Bioeng.*, 2001, 92, 493-501.
40. L. X. Wang, *Carbohydr. Res.*, 2008, 343, 1509-1522.
41. L. X. Wang and W. Huang, *Curr Opin Chem Biol*, 2009, 13, 592-600.
42. B. Li, Y. Zeng, S. Hauser, H. Song and L. X. Wang, *J Am Chem Soc*, 2005, 127, 9692-9693.
43. H. Li, B. Li, H. Song, L. Breydo, I. V. Baskakov and L. X. Wang, *J. Org. Chem.*, 2005, 70, 9990-9996.
44. B. Li, H. Song, S. Hauser and L. X. Wang, *Org Lett*, 2006, 8, 3081-3084.

45. Y. Zeng, J. Wang, B. Li, S. Hauser, H. Li and L. X. Wang, *Chem. Eur. J.,* 2006, 12, 3355-3364.
46. Y. Wei, C. Li, W. Huang, B. Li, S. Strome and L. X. Wang, *Biochemistry,* 2008, 47, 10294-10304.
47. H. Ochiai, W. Huang and L. X. Wang, *J Am Chem Soc,* 2008, 130, 13790-13803.
48. T. W. Rising, T. D. Claridge, J. W. Moir and A. J. Fairbanks, *ChemBioChem,* 2006, 7, 1177-1180.
49. T. W. Rising, T. D. Claridge, N. Davies, D. P. Gamblin, J. W. Moir and A. J. Fairbanks, *Carbohydr Res,* 2006, 341, 1574-1596.
50. T. W. Rising, C. D. Heidecke, J. W. Moir, Z. Ling and A. J. Fairbanks, *Chem. Eur. J.,* 2008, 14, 6444-6464.
51. T. B. Parsons, J. W. Moir and A. J. Fairbanks, *Org. Biomol. Chem.,* 2009, 7, 3128-3140.
52. M. Umekawa, W. Huang, B. Li, K. Fujita, H. Ashida, L. X. Wang and K. Yamamoto, *J Biol Chem,* 2008, 283, 4469-4479.
53. C. D. Heidecke, Z. Ling, N. C. Bruce, J. W. Moir, T. B. Parsons and A. J. Fairbanks, *Chembiochem,* 2008, 9, 2045-2051.
54. W. Huang, C. Li, B. Li, M. Umekawa, K. Yamamoto, X. Zhang and L. X. Wang, *J Am Chem Soc,* 2009, 131, 2214-2223.
55. M. Umekawa, C. Li, T. Higashiyama, W. Huang, H. Ashida, K. Yamamoto and L. X. Wang, *J Biol Chem,* 2010, 285, 511-521.
56. W. Huang, Q. Yang, M. Umekawa, K. Yamamoto and L. X. Wang, *Chembiochem,* 2010, 11, 1350-1355.
57. P. Kirsch, N. Kusunose, J. Aikawa, T. Kigawa, S. Yokoyama and T. Ogawa, *Bioorg Med Chem,* 1995, 3, 1631-1636.
58. T. Uchiyama and O. Hindsgaul, *Synlett,* 1996, 499-501.
59. K. Takegawa, K. Yamabe, K. Fujita, M. Tabuchi, M. Mita, H. Izu, A. Watanabe, Y. Asada, M. Sano, A. Kondo, I. Kato and S. Iwahara, *Arch. Biochem. Biophys.,* 1997, 338, 22-28.
60. K. Yamamoto, S. Kadowaki, M. Fujisaki, H. Kumagai and T. Tochikura, *Biosci Biotechnol Biochem,* 1994, 58, 72-77.
61. R. B. Trimble, P. H. Atkinson, A. L. Tarentino, T. H. Plummer, Jr., F. Maley and K. B. Tomer, *J Biol Chem,* 1986, 261, 12000-12005.
62. T. B. Parsons, M. K. Patel, A. B. Boraston, D. J. Vocadlo and A. J. Fairbanks, *Org Biomol Chem,* 2010, 8, 1861-1869.
63. H. Muramatsu, H. Tachikui, H. Ushida, X. Song, Y. Qiu, S. Yamamoto and T. Muramatsu, *Journal of Biochemistry,* 2001, 129, 923-928.
64. A. Treumann, M. R. Lifely, P. Schneider and M. A. Ferguson, *J Biol Chem,* 1995, 270, 6088-6099.
65. S. Schroter, P. Den, H. S. Conradt, M. Nimtz, G. Hale and C. Kirchhoff, *J Biol Chem,* 1999, 274, 29862-29873.
66. A. Domagala and M. Kurpisz, *Med Sci Monit,* 2001, 7, 325-331.
67. N. Shao, J. Xue and Z. Guo, *J. Org. Chem.,* 2003, 68, 9003-9011.
68. N. Shao, J. Xue and Z. Guo, *Angew. Chem. Int. Ed.,* 2004, 43, 1569-1573.
69. M. R. Pratt and C. R. Bertozzi, *J. Am. Chem. Soc.,* 2003, 125, 6149-6159.
70. H. Li, S. Singh, Y. Zeng, H. Song and L. X. Wang, *Bioorg. Med. Chem. Lett.,* 2005, 15, 895-898.
71. K. Haneda, T. Inazu, K. Yamamoto, H. Kumagai, Y. Nakahara and A. Kobata, *Carbohydr. Res.,* 1996, 292, 61-70.
72. K. Fujita, N. Tanaka, M. Sano, I. Kato, Y. Asada and K. Takegawa, *Biochem. Biophys. Res. Commun.,* 2000, 267, 134-138.
73. V. Rao, C. Guan, P. Van Roey, *Structure* 1995, 3, 449-457.
74. R. B. Trimble, A. L. Tarentino, *J. Biol. Chem.* 1991, 266, 1646-1651. L. Tarentino, T. H. Plummer, Jr., *Methods Enzymol.* 1994, 230, 44-57.
75. Reddy, B. G. Grimwood, T. H. Plummer, A. L. Tarentino, *Glycobiology* 1998, 8, 633-636.
76. L. Tarentino, G. Quinones, T. H. Plummer, Jr., *Glycobiology* 1995, 5, 599-601.
77. T. H. Plummer, Jr., A. W. Phelan, A. L. Tarentino, *Anal. Biochem.* 1996, 235, 98-101.
78. A. Waddling, T. H. Plummer, Jr., A. L. Tarentino, P. Van Roey, *Biochemistry* 2000, 39, 7878-7885.
79. Tews, A. C. Terwisscha van Scheltinga, A. Perrakis, K. S. Wilson, B. W. Dijkstra, *J. Am. Chem. Soc.* 1997, 119, 7954-7959.
80. A. Brameld, W. D. Shrader, B. Imperiali, W. A. Goddard, 3rd, *J. Mol. Biol.* 1998, 280, 913-923.
81. W. Huang, X. Zhang, T. Ju, R. D. Cummings, L. X. Wang, *Org. Biomol. Chem.* 2010, 8, 5224-5233.
82. P. Kuhn, A. L. Tarentino, T. H. Plummer, Jr., P. Van Roey, *Biochemistry* 1994, 33, 11699-11706.
83. L. Tarentino, G. Quinones, A. Trumble, L. M. Changchien, B. Duceman, F. Maley, T. H. Plummer, Jr., *J. Biol. Chem.* 1990, 265, 6961-6966.
84. Tarentino, A. L., Quinones, G., Changchien, L. M. and Plummer, T. H. Jr., *J. Biol. Chem.,* 268 (13), 9702-9708 (1993).
85. Camilli, R., Del Grosso, M., Iannelli, F. and Pantosti, A., *Antimicrob. Agents Chemother.* 52 (2), 619-625 (2008)]
86. Raju, T. S., and Scallon, B. J. (2006) *Biochem. Biophys. Res. Commun.* 341, 797-803.
87. Abbott, D. W., Macauley, M. S., Vocadlo, D. J., and Boraston, A. B. (2009) *J. Biol. Chem.* 284, 11676-11689.

That which is claimed is:

1. A method of preparing a core-fucosylated glycopeptide or core-fucosylated glycoprotein having a predetermined oligosaccharide moiety, the method comprising:
providing a core-fucosylated acceptor glycopeptide or core-fucosylated acceptor glycoprotein comprising an asparagine-linked N-acetylglucosamine (GlcNAc) residue linked to a core fucose residue, wherein the core-fucosylated acceptor glycopeptide or core-fucosylated acceptor glycoprotein is an alpha-1-6-fucosyl-GlcNAc-peptide or an alpha-1-6-fucosyl-GlcNAc-protein; and
enzymatically reacting the core-fucosylated acceptor glycoprotein or core-fucosylated acceptor glycopeptide with an activated oligosaccharide donor in the presence of a buffer and at least one fusion protein comprising a cysteine protease domain (CPD) and an endoglycosidase selected from the group consisting of Endoglycosidase-F2 D124A mutant (SEQ ID NO: 4), Endoglycosidase-F2 D124Q mutant (SEQ ID NO: 5), Endoglycosidase-F3 D126A mutant (SEQ ID NO: 6), and Endoglycosidase-F3 D126Q mutant (SEQ ID NO: 7), wherein the activated oligosaccharide donor comprises an oxazoline covalently linked to a oligosaccharide moiety, wherein the oligosaccharide moiety comprises a predetermined number and type of sugar residues, and wherein the enzymatic reaction covalently links the oligosaccharide moiety to the core-fucosylated acceptor glycoprotein or core-fucosylated acceptor glycopeptide; thereby providing the core-fucosylated glycoprotein or core-fucosylated acceptor glycopeptide having the predetermined oligosaccharide moiety.

2. The method of claim 1, wherein the core-fucosylated acceptor glycopeptide or core-fucosylated acceptor glycoprotein is an antibody or fragment thereof.

3. The method of claim 1, wherein the activated oligosaccharide donor is a synthetic oligosaccharide oxazoline.

4. The method of claim 3, wherein the synthetic oligosaccharide oxazoline is a di-, tri-, tetra-, penta-, hexyl-, hepta-, octyl-, nona-, deca-, or undeca-saccharide oxazoline.

5. The method of claim 1, wherein the synthetic oligosaccharide oxazoline further comprises an additional biologically active agent or a tag.

6. The method of claim 5, wherein the additional biologically active agent or tag is a drug, toxin, fluorescent probe, biotin, a PEG, lipid, or polypeptide.

7. The method of claim 2, wherein the antibody is a monoclonal antibody selected from the group consisting of cetuximab, rituximab, muromonab-CD3, abciximab, daclizumab, basiliximab, palivizumab, infliximab, trastuzumab, gemtuzumab ozogamicin, alemtuzumab, ibritumomab tiuxetan, adalimumab, omalizumab, tositumomab, efalizumab, bevacizumab, panitumumab, pertuzumab, natalizumab, etanercept, volociximab, Anti-CD80 mAb, Anti-CD23 mAb, eraptuzumab, matuzumab, zanolimumab, adecatumumab, oregovomab, nimotuzumab, denosumab, fontolizumab, daclizumab, golimumab, ocrelizumab, HuMax-CD20, belimumab, epratuzumab, visilizumab, tocilizumab, ocrerlizumab, certolizumab pegol, eculizumab, pexelizumab, abciximab, ranibizimumab, and mepolizumab.

8. The method of claim 1, wherein the step of providing the core-fucosylated acceptor glycopeptide or core-fucosylated acceptor glycoprotein comprises
    (a) providing a core-fucosylated glycopeptide or core-fucosylated acceptor glycoprotein substrate comprising at least two GlcNAc residues in a chain positioned next to the protein or peptide; and
    (b) treating the core-fucosylated glycopeptide or core-fucosylated acceptor glycoprotein substrate with an endo-enzyme to hydrolyze the bond between the two GlcNAc residues positioned closest to the peptide or protein thereby forming the core-fucosylated acceptor glycopeptide or core-fucosylated acceptor glycoprotein having a single GlcNAc-moiety.

9. The method of claim 2, wherein the antibody or fragment thereof further comprises an additional moiety selected from a group consisting of a therapeutic agent for treating cancer, a therapeutic agent for HIV; a toxin, an antibody different from the modified antibody which is reactive to another receptor, an antigen, a chemokine and a cytokine.

10. The method of claim 1, further comprising:
    (a) providing a core-fucosylated glycoprotein or core-fucosylated acceptor glycopeptide comprising heterogeneous N-glycans;
    (b) removing the heterogeneous N-glycans by an enzyme selected from the group consisting of Endo S, Endo-H, and Endo-A to form the core-fucosylated acceptor glycoprotein or core-fucosylated acceptor glycopeptide.

11. The method of claim 1, wherein the at least one endoglycosidase is Endoglycosidase-F2 D124A mutant (SEQ ID NO: 4).

12. The method of claim 1, wherein the at least one endoglycosidase is Endoglycosidase-F2 D124Q mutant (SEQ ID NO: 5).

13. The method of claim 1, wherein the at least one endoglycosidase is Endoglycosidase-F3 D126A mutant (SEQ ID NO: 6).

14. The method of claim 1, wherein the at least one endoglycosidase is Endoglycosidase-F3 D126Q mutant (SEQ ID NO: 7).

15. The method of claim 1, wherein the oxazoline is a glycan oxazoline.

16. The method of claim 15, wherein the glycan oxazoline is selected from the group consisting of a complex type N-glycan oxazoline, a truncated N-glycan oxazoline, and a sialylated N-glycan oxazoline.

17. The method of claim 10, wherein the enzyme is Endo S.

18. The method of claim 8, wherein the endo-enzyme is Endo S.

19. The method of claim 1, wherein the at least one endoglycosidase is selected from the group consisting of Endoglycosidase-F2 D124Q mutant (SEQ ID NO: 5) and Endoglycosidase-F3 D126Q mutant (SEQ ID NO: 7).

* * * * *

SEQUENCE LISTING

<160> NUMBER OF SEQ ID NOS: 17

<210> SEQ ID NO 1
<211> LENGTH: 289
<212> TYPE: PRT
<213> ORGANISM: Artificial Sequence
<220> FEATURE:
<223> OTHER INFORMATION: SYNTHETIC CONSTRUCT

<400> SEQUENCE: 1

Ala Val Thr Gly Thr Thr Lys Ala Asn Ile Lys Leu Phe Ser Phe Thr
1               5                   10                  15

```
Glu Val Asn Asp Thr Asn Pro Leu Asn Asn Leu Asn Phe Thr Leu Lys
         20                  25                  30

Asn Ser Gly Lys Pro Leu Val Asp Met Val Val Leu Phe Ser Ala Asn
         35                  40                  45

Ile Asn Tyr Asp Ala Ala Asn Asp Lys Val Phe Val Ser Asn Asn Pro
 50                  55                  60

Asn Val Gln His Leu Leu Thr Asn Arg Ala Lys Tyr Leu Lys Pro Leu
 65                  70                  75                  80

Gln Asp Lys Gly Ile Lys Val Ile Leu Ser Ile Leu Gly Asn His Asp
             85                  90                  95

Arg Ser Gly Ile Ala Asn Leu Ser Thr Ala Arg Ala Lys Ala Phe Ala
            100                 105                 110

Gln Glu Leu Lys Asn Thr Cys Asp Leu Tyr Asn Leu Asp Gly Val Phe
            115                 120                 125

Phe Asp Asp Glu Tyr Ser Ala Tyr Gln Thr Pro Pro Ser Gly Phe
130                 135                 140

Val Thr Pro Ser Asn Asn Ala Ala Ala Arg Leu Ala Tyr Glu Thr Lys
145                 150                 155                 160

Gln Ala Met Pro Asn Lys Leu Val Thr Val Tyr Val Tyr Ser Arg Thr
                165                 170                 175

Ser Ser Phe Pro Thr Ala Val Asp Gly Val Asn Ala Gly Ser Tyr Val
                180                 185                 190

Asp Tyr Ala Ile His Asp Tyr Gly Gly Ser Tyr Asp Leu Ala Thr Asn
                195                 200                 205

Tyr Pro Gly Leu Ala Lys Ser Gly Met Val Met Ser Ser Gln Glu Phe
210                 215                 220

Asn Gln Gly Arg Tyr Ala Thr Ala Gln Ala Leu Arg Asn Ile Val Thr
225                 230                 235                 240

Lys Gly Tyr Gly Gly His Met Ile Phe Ala Met Asp Pro Asn Arg Ser
                245                 250                 255

Asn Phe Thr Ser Gly Gln Leu Pro Ala Leu Lys Leu Ile Ala Lys Glu
                260                 265                 270

Leu Tyr Gly Asp Glu Leu Val Tyr Ser Asn Thr Pro Tyr Ser Lys Asp
                275                 280                 285

Trp

<210> SEQ ID NO 2
<211> LENGTH: 290
<212> TYPE: PRT
<213> ORGANISM: Artificial Sequence
<220> FEATURE:
<223> OTHER INFORMATION: SYNTHETIC CONSTRUCT

<400> SEQUENCE: 2

Ala Val Asn Leu Ser Asn Leu Ile Ala Tyr Lys Asn Ser Asp His Gln
 1               5                  10                  15

Ile Ser Ala Gly Tyr Tyr Arg Thr Trp Arg Asp Ser Ala Thr Ala Ser
             20                  25                  30

Gly Asn Leu Pro Ser Met Arg Trp Leu Pro Asp Ser Leu Asp Met Val
             35                  40                  45

Met Val Phe Pro Asp Tyr Thr Pro Pro Glu Asn Ala Tyr Trp Asn Thr
 50                  55                  60

Leu Lys Thr Asn Tyr Val Pro Tyr Leu His Lys Arg Gly Thr Lys Val
 65                  70                  75                  80
```

```
Ile Ile Thr Leu Gly Asp Leu Asn Ser Ala Thr Thr Gly Gly Gln
            85                  90                  95

Asp Ser Ile Gly Tyr Ser Ser Trp Ala Lys Gly Ile Tyr Asp Lys Trp
           100                 105                 110

Val Gly Glu Tyr Asn Leu Asp Gly Ile Asp Ile Asp Ile Glu Ser Ser
           115                 120                 125

Pro Ser Gly Ala Thr Leu Thr Lys Phe Val Ala Ala Thr Lys Ala Leu
           130                 135             140

Ser Lys Tyr Phe Gly Pro Lys Ser Gly Thr Gly Lys Thr Phe Val Tyr
145                 150                 155                 160

Asp Thr Asn Gln Asn Pro Thr Asn Phe Phe Ile Gln Thr Ala Pro Arg
                165                 170                 175

Tyr Asn Tyr Val Phe Leu Gln Ala Tyr Gly Arg Ser Thr Thr Asn Leu
                180                 185                 190

Thr Thr Val Ser Gly Leu Tyr Ala Pro Tyr Ile Ser Met Lys Gln Phe
            195                 200                 205

Leu Pro Gly Phe Ser Phe Tyr Glu Glu Asn Gly Tyr Pro Gly Asn Tyr
            210                 215                 220

Trp Asn Asp Val Arg Tyr Pro Gln Asn Gly Thr Gly Arg Ala Tyr Asp
225                 230                 235                 240

Tyr Ala Arg Trp Gln Pro Ala Thr Gly Lys Lys Gly Val Phe Ser
                245                 250                 255

Tyr Ala Ile Glu Arg Asp Ala Pro Leu Thr Ser Ser Asn Asp Asn Thr
                260                 265                 270

Leu Arg Ala Pro Asn Phe Arg Val Thr Lys Asp Leu Ile Lys Ile Met
            275                 280                 285

Asn Pro
    290

<210> SEQ ID NO 3
<211> LENGTH: 290
<212> TYPE: PRT
<213> ORGANISM: Artificial Sequence
<220> FEATURE:
<223> OTHER INFORMATION: SYNTHETIC CONSTRUCT

<400> SEQUENCE: 3

Ala Thr Ala Leu Ala Gly Ser Asn Gly Val Cys Ile Ala Tyr Tyr Ile
1               5                   10                  15

Thr Asp Gly Arg Asn Pro Thr Phe Lys Leu Lys Asp Ile Pro Asp Lys
            20                  25                  30

Val Asp Met Val Ile Leu Phe Gly Leu Lys Tyr Trp Ser Leu Gln Asp
            35                  40                  45

Thr Thr Lys Leu Pro Gly Gly Thr Gly Met Met Gly Ser Phe Lys Ser
50                  55                  60

Tyr Lys Asp Leu Asp Thr Gln Ile Arg Ser Leu Gln Ser Arg Gly Ile
65                  70                  75                  80

Lys Val Leu Gln Asn Ile Asp Asp Val Ser Trp Gln Ser Ser Lys
                85                  90                  95

Pro Gly Gly Phe Ala Ser Ala Ala Tyr Gly Asp Ala Ile Lys Ser
            100                 105                 110

Ile Val Ile Asp Lys Trp Lys Leu Asp Gly Ile Ser Leu Asp Ile Glu
            115                 120                 125

His Ser Gly Ala Lys Pro Asn Pro Ile Pro Thr Phe Pro Gly Tyr Ala
        130                 135                 140
```

```
Ala Thr Gly Tyr Asn Gly Trp Tyr Ser Gly Ser Met Ala Ala Thr Pro
145                 150                 155                 160

Ala Phe Leu Asn Val Ile Ser Glu Leu Thr Lys Tyr Phe Gly Thr Thr
                165                 170                 175

Ala Pro Asn Asn Lys Gln Leu Gln Ile Ala Ser Gly Ile Asp Val Tyr
            180                 185                 190

Ala Trp Asn Lys Ile Met Glu Asn Phe Arg Asn Asn Phe Asn Tyr Ile
        195                 200                 205

Gln Leu Gln Ser Tyr Gly Ala Asn Val Ser Arg Thr Gln Leu Met Met
    210                 215                 220

Asn Tyr Ala Thr Gly Thr Asn Lys Ile Pro Ala Ser Lys Met Val Phe
225                 230                 235                 240

Gly Ala Tyr Ala Glu Gly Gly Thr Asn Gln Ala Asn Asp Val Glu Val
                245                 250                 255

Ala Lys Trp Thr Pro Thr Gln Gly Ala Lys Gly Gly Met Met Ile Tyr
            260                 265                 270

Thr Tyr Asn Ser Asn Val Ser Tyr Ala Asn Ala Val Arg Asp Ala Val
        275                 280                 285

Lys Asn
    290

<210> SEQ ID NO 4
<211> LENGTH: 290
<212> TYPE: PRT
<213> ORGANISM: Artificial Sequence
<220> FEATURE:
<223> OTHER INFORMATION: SYNTHETIC CONSTRUCT

<400> SEQUENCE: 4

Ala Val Asn Leu Ser Asn Leu Ile Ala Tyr Lys Asn Ser Asp His Gln
1               5                   10                  15

Ile Ser Ala Gly Tyr Tyr Arg Thr Trp Arg Asp Ser Ala Thr Ala Ser
            20                  25                  30

Gly Asn Leu Pro Ser Met Arg Trp Leu Pro Asp Ser Leu Asp Met Val
        35                  40                  45

Met Val Phe Pro Asp Tyr Thr Pro Pro Glu Asn Ala Tyr Trp Asn Thr
    50                  55                  60

Leu Lys Thr Asn Tyr Val Pro Tyr Leu His Lys Arg Gly Thr Lys Val
65                  70                  75                  80

Ile Ile Thr Leu Gly Asp Leu Asn Ser Ala Thr Thr Thr Gly Gly Gln
                85                  90                  95

Asp Ser Ile Gly Tyr Ser Ser Trp Ala Lys Gly Ile Tyr Asp Lys Trp
            100                 105                 110

Val Gly Glu Tyr Asn Leu Asp Gly Ile Asp Ile Ala Ile Glu Ser Ser
        115                 120                 125

Pro Ser Gly Ala Thr Leu Thr Lys Phe Val Ala Ala Thr Lys Ala Leu
    130                 135                 140

Ser Lys Tyr Phe Gly Pro Lys Ser Gly Thr Gly Lys Thr Phe Val Tyr
145                 150                 155                 160

Asp Thr Asn Gln Asn Pro Thr Asn Phe Phe Ile Gln Thr Ala Pro Arg
                165                 170                 175

Tyr Asn Tyr Val Phe Leu Gln Ala Tyr Gly Arg Ser Thr Thr Asn Leu
            180                 185                 190

Thr Thr Val Ser Gly Leu Tyr Ala Pro Tyr Ile Ser Met Lys Gln Phe
        195                 200                 205
```

Leu Pro Gly Phe Ser Phe Tyr Glu Glu Asn Gly Tyr Pro Gly Asn Tyr
            210                 215                 220

Trp Asn Asp Val Arg Tyr Pro Gln Asn Gly Thr Gly Arg Ala Tyr Asp
225                 230                 235                 240

Tyr Ala Arg Trp Gln Pro Ala Thr Gly Lys Lys Gly Val Phe Ser
                245                 250                 255

Tyr Ala Ile Glu Arg Asp Ala Pro Leu Thr Ser Ser Asn Asp Asn Thr
                260                 265                 270

Leu Arg Ala Pro Asn Phe Arg Val Thr Lys Asp Leu Ile Lys Ile Met
            275                 280                 285

Asn Pro
    290

<210> SEQ ID NO 5
<211> LENGTH: 290
<212> TYPE: PRT
<213> ORGANISM: Artificial Sequence
<220> FEATURE:
<223> OTHER INFORMATION: SYNTHETIC CONSTRUCT

<400> SEQUENCE: 5

Ala Val Asn Leu Ser Asn Leu Ile Ala Tyr Lys Asn Ser Asp His Gln
1               5                   10                  15

Ile Ser Ala Gly Tyr Tyr Arg Thr Trp Arg Asp Ser Ala Thr Ala Ser
            20                  25                  30

Gly Asn Leu Pro Ser Met Arg Trp Leu Pro Asp Ser Leu Asp Met Val
        35                  40                  45

Met Val Phe Pro Asp Tyr Thr Pro Pro Glu Asn Ala Tyr Trp Asn Thr
50                  55                  60

Leu Lys Thr Asn Tyr Val Pro Tyr Leu His Lys Arg Gly Thr Lys Val
65                  70                  75                  80

Ile Ile Thr Leu Gly Asp Leu Asn Ser Ala Thr Thr Thr Gly Gly Gln
                85                  90                  95

Asp Ser Ile Gly Tyr Ser Ser Trp Ala Lys Gly Ile Tyr Asp Lys Trp
            100                 105                 110

Val Gly Glu Tyr Asn Leu Asp Gly Ile Asp Ile Gln Ile Glu Ser Ser
        115                 120                 125

Pro Ser Gly Ala Thr Leu Thr Lys Phe Val Ala Ala Thr Lys Ala Leu
130                 135                 140

Ser Lys Tyr Phe Gly Pro Lys Ser Gly Thr Gly Lys Thr Phe Val Tyr
145                 150                 155                 160

Asp Thr Asn Gln Asn Pro Thr Asn Phe Phe Ile Gln Thr Ala Pro Arg
                165                 170                 175

Tyr Asn Tyr Val Phe Leu Gln Ala Tyr Gly Arg Ser Thr Thr Asn Leu
            180                 185                 190

Thr Thr Val Ser Gly Leu Tyr Ala Pro Tyr Ile Ser Met Lys Gln Phe
        195                 200                 205

Leu Pro Gly Phe Ser Phe Tyr Glu Glu Asn Gly Tyr Pro Gly Asn Tyr
210                 215                 220

Trp Asn Asp Val Arg Tyr Pro Gln Asn Gly Thr Gly Arg Ala Tyr Asp
225                 230                 235                 240

Tyr Ala Arg Trp Gln Pro Ala Thr Gly Lys Lys Gly Val Phe Ser
                245                 250                 255

Tyr Ala Ile Glu Arg Asp Ala Pro Leu Thr Ser Ser Asn Asp Asn Thr
                260                 265                 270

Leu Arg Ala Pro Asn Phe Arg Val Thr Lys Asp Leu Ile Lys Ile Met
        275                 280                 285

Asn Pro
    290

<210> SEQ ID NO 6
<211> LENGTH: 290
<212> TYPE: PRT
<213> ORGANISM: Artificial Sequence
<220> FEATURE:
<223> OTHER INFORMATION: SYNTHETIC CONSTRUCT

<400> SEQUENCE: 6

Ala Thr Ala Leu Ala Gly Ser Asn Gly Val Cys Ile Ala Tyr Tyr Ile
1               5                   10                  15

Thr Asp Gly Arg Asn Pro Thr Phe Lys Leu Lys Asp Ile Pro Asp Lys
            20                  25                  30

Val Asp Met Val Ile Leu Phe Gly Leu Lys Tyr Trp Ser Leu Gln Asp
        35                  40                  45

Thr Thr Lys Leu Pro Gly Gly Thr Gly Met Met Gly Ser Phe Lys Ser
    50                  55                  60

Tyr Lys Asp Leu Asp Thr Gln Ile Arg Ser Leu Gln Ser Arg Gly Ile
65                  70                  75                  80

Lys Val Leu Gln Asn Ile Asp Asp Val Ser Trp Gln Ser Ser Lys
                85                  90                  95

Pro Gly Gly Phe Ala Ser Ala Ala Tyr Gly Asp Ala Ile Lys Ser
            100                 105                 110

Ile Val Ile Asp Lys Trp Lys Leu Asp Gly Ile Ser Leu Ala Ile Glu
        115                 120                 125

His Ser Gly Ala Lys Pro Asn Pro Ile Pro Thr Phe Pro Gly Tyr Ala
    130                 135                 140

Ala Thr Gly Tyr Asn Gly Trp Tyr Ser Gly Ser Met Ala Ala Thr Pro
145                 150                 155                 160

Ala Phe Leu Asn Val Ile Ser Glu Leu Thr Lys Tyr Phe Gly Thr Thr
                165                 170                 175

Ala Pro Asn Asn Lys Gln Leu Gln Ile Ala Ser Gly Ile Asp Val Tyr
            180                 185                 190

Ala Trp Asn Lys Ile Met Glu Asn Phe Arg Asn Asn Phe Asn Tyr Ile
        195                 200                 205

Gln Leu Gln Ser Tyr Gly Ala Asn Val Ser Arg Thr Gln Leu Met Met
    210                 215                 220

Asn Tyr Ala Thr Gly Thr Asn Lys Ile Pro Ala Ser Lys Met Val Phe
225                 230                 235                 240

Gly Ala Tyr Ala Glu Gly Gly Thr Asn Gln Ala Asn Asp Val Glu Val
                245                 250                 255

Ala Lys Trp Thr Pro Thr Gln Gly Ala Lys Gly Gly Met Met Ile Tyr
            260                 265                 270

Thr Tyr Asn Ser Asn Val Ser Tyr Ala Asn Ala Val Arg Asp Ala Val
        275                 280                 285

Lys Asn
    290

<210> SEQ ID NO 7
<211> LENGTH: 290
<212> TYPE: PRT
<213> ORGANISM: Artificial Sequence
<220> FEATURE:

<223> OTHER INFORMATION: SYNTHETIC CONSTRUCT

<400> SEQUENCE: 7

```
Ala Thr Ala Leu Ala Gly Ser Asn Gly Val Cys Ile Ala Tyr Tyr Ile
1               5                   10                  15

Thr Asp Gly Arg Asn Pro Thr Phe Lys Leu Lys Asp Ile Pro Asp Lys
            20                  25                  30

Val Asp Met Val Ile Leu Phe Gly Leu Lys Tyr Trp Ser Leu Gln Asp
        35                  40                  45

Thr Thr Lys Leu Pro Gly Gly Thr Gly Met Met Gly Ser Phe Lys Ser
    50                  55                  60

Tyr Lys Asp Leu Asp Thr Gln Ile Arg Ser Leu Gln Ser Arg Gly Ile
65                  70                  75                  80

Lys Val Leu Gln Asn Ile Asp Asp Val Ser Trp Gln Ser Ser Lys
                85                  90                  95

Pro Gly Gly Phe Ala Ser Ala Ala Tyr Gly Asp Ala Ile Lys Ser
            100                 105                 110

Ile Val Ile Asp Lys Trp Lys Leu Asp Gly Ile Ser Leu Gln Ile Glu
        115                 120                 125

His Ser Gly Ala Lys Pro Asn Pro Ile Pro Thr Phe Pro Gly Tyr Ala
    130                 135                 140

Ala Thr Gly Tyr Asn Gly Trp Tyr Ser Gly Ser Met Ala Ala Thr Pro
145                 150                 155                 160

Ala Phe Leu Asn Val Ile Ser Glu Leu Thr Lys Tyr Phe Gly Thr Thr
                165                 170                 175

Ala Pro Asn Asn Lys Gln Leu Gln Ile Ala Ser Gly Ile Asp Val Tyr
            180                 185                 190

Ala Trp Asn Lys Ile Met Glu Asn Phe Arg Asn Asn Phe Asn Tyr Ile
        195                 200                 205

Gln Leu Gln Ser Tyr Gly Ala Asn Val Ser Arg Thr Gln Leu Met Met
    210                 215                 220

Asn Tyr Ala Thr Gly Thr Asn Lys Ile Pro Ala Ser Lys Met Val Phe
225                 230                 235                 240

Gly Ala Tyr Ala Glu Gly Gly Thr Asn Gln Ala Asn Asp Val Glu Val
                245                 250                 255

Ala Lys Trp Thr Pro Thr Gln Gly Ala Lys Gly Gly Met Met Ile Tyr
            260                 265                 270

Thr Tyr Asn Ser Asn Val Ser Tyr Ala Asn Ala Val Arg Asp Ala Val
        275                 280                 285

Lys Asn
    290
```

<210> SEQ ID NO 8
<211> LENGTH: 1646
<212> TYPE: PRT
<213> ORGANISM: Artificial Sequence
<220> FEATURE:
<223> OTHER INFORMATION: SYNTHETIC CONSTRUCT

<400> SEQUENCE: 8

```
Met Lys Asn Pro Phe Phe Glu Arg Arg Cys Arg Tyr Ser Ile Arg Lys
1               5                   10                  15

Leu Ser Val Gly Ala Cys Ser Leu Met Ile Gly Ala Val Leu Phe Val
            20                  25                  30

Gly Pro Ala Leu Ala Glu Glu Thr Ala Val Pro Glu Asn Ser Gly Ala
        35                  40                  45
```

```
Asn Thr Glu Leu Val Ser Gly Glu Ser Glu His Ser Thr Asn Glu Ala
        50                  55                  60

Asp Lys Gln Asn Glu Gly Glu His Thr Arg Glu Asn Lys Leu Glu Lys
65                  70                  75                  80

Ala Glu Gly Val Ala Thr Ala Ser Glu Thr Ala Glu Ala Ala Ser Ala
                85                  90                  95

Ala Lys Pro Glu Glu Lys Ala Gly Glu Val Val Ala Glu Thr Pro Ser
                100                 105                 110

Ala Glu Ala Lys Pro Lys Ser Asp Lys Glu Thr Glu Ala Lys Pro Glu
            115                 120                 125

Ala Thr Asn Gln Gly Asp Glu Ser Lys Pro Ala Ala Glu Ala Asn Lys
            130                 135                 140

Thr Glu Lys Glu Val Gln Pro Asp Val Pro Lys Asn Thr Glu Lys Thr
145                 150                 155                 160

Leu Lys Pro Lys Glu Ile Lys Phe Asn Ser Trp Glu Leu Leu Lys
                165                 170                 175

Trp Glu Pro Gly Ala Arg Glu Asp Ala Ile Asn Arg Gly Ser Val
                180                 185                 190

Val Leu Ala Ser Arg Arg Thr Gly His Leu Val Asn Glu Lys Ala Ser
            195                 200                 205

Lys Glu Ala Lys Val Gln Ala Leu Ser Asn Thr Asn Ser Lys Ala Lys
    210                 215                 220

Asp His Ala Ser Val Gly Gly Glu Glu Phe Lys Ala Tyr Ala Phe Asp
225                 230                 235                 240

Tyr Trp Gln Tyr Leu Asp Ser Met Val Phe Trp Glu Gly Leu Val Pro
                245                 250                 255

Thr Pro Asp Val Ile Asp Ala Gly His Arg Asn Gly Val Pro Val Tyr
                260                 265                 270

Gly Thr Leu Phe Phe Asn Trp Ser Asn Ser Ile Ala Asp Gln Glu Arg
            275                 280                 285

Phe Ala Glu Ala Leu Lys Gln Asp Ala Asp Gly Ser Phe Pro Ile Ala
            290                 295                 300

Arg Lys Leu Val Asp Met Ala Lys Tyr Tyr Gly Tyr Asp Gly Tyr Phe
305                 310                 315                 320

Ile Ala Gln Glu Thr Thr Gly Asp Leu Val Lys Pro Leu Gly Glu Lys
                325                 330                 335

Met Arg Gln Phe Met Leu Tyr Ser Lys Glu Tyr Ala Ala Lys Val Asn
                340                 345                 350

His Pro Ile Lys Tyr Ser Trp Tyr Asp Ala Met Thr Tyr Asn Tyr Gly
            355                 360                 365

Arg Tyr His Gln Asp Gly Leu Gly Glu Tyr Asn Tyr Gln Phe Met Gln
370                 375                 380

Pro Glu Gly Asp Lys Val Pro Ala Asp Asn Phe Ala Asn Phe Asn
385                 390                 395                 400

Trp Asp Lys Ala Lys Asn Asp Tyr Thr Ile Ala Thr Ala Asn Trp Ile
                405                 410                 415

Gly Arg Asn Pro Tyr Asp Val Phe Ala Gly Leu Glu Leu Gln Gln Gly
            420                 425                 430

Gly Ser Tyr Lys Thr Lys Val Lys Trp Asn Asp Ile Leu Asp Glu Asn
            435                 440                 445

Gly Lys Leu Arg Leu Ser Leu Gly Leu Phe Ala Pro Asp Thr Ile Thr
450                 455                 460
```

-continued

```
Ser Leu Gly Lys Thr Gly Glu Asp Tyr His Lys Asn Glu Asp Ile Phe
465                 470                 475                 480

Phe Thr Gly Tyr Gln Gly Asp Pro Thr Gly Gln Lys Pro Gly Asp Lys
            485                 490                 495

Asp Trp Tyr Gly Ile Ala Asn Leu Val Ala Asp Arg Thr Pro Ala Val
            500                 505                 510

Gly Asn Thr Phe Thr Thr Ser Phe Asn Thr Gly His Gly Lys Lys Trp
            515                 520                 525

Phe Val Asp Gly Lys Val Ser Lys Asp Ser Glu Trp Asn Tyr Arg Ser
    530                 535                 540

Val Ser Gly Val Leu Pro Thr Trp Arg Trp Gln Thr Ser Thr Gly
545                 550                 555                 560

Glu Lys Leu Arg Ala Glu Tyr Asp Phe Thr Asp Ala Tyr Asn Gly Gly
            565                 570                 575

Asn Ser Leu Lys Phe Ser Gly Asp Val Ala Gly Lys Thr Asp Gln Asp
            580                 585                 590

Val Arg Leu Tyr Ser Thr Lys Leu Glu Val Thr Glu Lys Thr Lys Leu
    595                 600                 605

Arg Val Ala His Lys Gly Gly Lys Gly Ser Lys Val Tyr Met Ala Phe
    610                 615                 620

Ser Thr Thr Pro Asp Tyr Lys Phe Asp Asp Ala Asp Ala Trp Lys Glu
625                 630                 635                 640

Leu Thr Leu Ser Asp Asn Trp Thr Asn Glu Glu Phe Asp Leu Ser Ser
            645                 650                 655

Leu Ala Gly Lys Thr Ile Tyr Ala Val Lys Leu Phe Phe Glu His Glu
            660                 665                 670

Gly Ala Val Lys Asp Tyr Gln Phe Asn Leu Gly Gln Leu Thr Ile Ser
            675                 680                 685

Asp Asn His Gln Glu Pro Gln Ser Pro Thr Ser Phe Ser Val Val Lys
            690                 695                 700

Gln Ser Leu Lys Asn Ala Gln Glu Ala Glu Ala Val Val Gln Phe Lys
705                 710                 715                 720

Gly Asn Lys Asp Ala Asp Phe Tyr Glu Val Tyr Glu Lys Asp Gly Asp
            725                 730                 735

Ser Trp Lys Leu Leu Thr Gly Ser Ser Thr Thr Ile Tyr Leu Pro
            740                 745                 750

Lys Val Ser Arg Ser Ala Ser Ala Gln Gly Thr Thr Gln Glu Leu Lys
            755                 760                 765

Val Val Ala Val Gly Lys Asn Gly Val Arg Ser Glu Ala Ala Thr Thr
    770                 775                 780

Thr Phe Asp Trp Gly Met Thr Val Lys Asp Thr Ser Leu Pro Lys Pro
785                 790                 795                 800

Leu Ala Glu Asn Ile Val Pro Gly Ala Thr Val Ile Asp Ser Thr Phe
            805                 810                 815

Pro Lys Thr Glu Gly Gly Glu Gly Ile Glu Gly Met Leu Asn Gly Thr
            820                 825                 830

Ile Thr Ser Leu Ser Asp Lys Trp Ser Ser Ala Gln Leu Ser Gly Ser
            835                 840                 845

Val Asp Ile Arg Leu Thr Lys Pro Arg Thr Val Val Arg Trp Val Met
    850                 855                 860

Asp His Ala Gly Ala Gly Gly Glu Ser Val Asn Asp Gly Leu Met Asn
865                 870                 875                 880

Thr Lys Asp Phe Asp Leu Tyr Tyr Lys Asp Ala Asp Gly Glu Trp Lys
```

-continued

```
                885                 890                 895
Leu Ala Lys Glu Val Arg Gly Asn Lys Ala His Val Thr Asp Ile Thr
            900                 905                 910
Leu Asp Lys Pro Ile Thr Ala Gln Asp Trp Arg Leu Asn Val Val Thr
            915                 920                 925
Ser Asp Asn Gly Thr Pro Trp Lys Ala Ile Arg Ile Tyr Asn Trp Lys
            930                 935                 940
Met Tyr Glu Lys Leu Asp Thr Glu Ser Val Asn Ile Pro Met Ala Lys
945                 950                 955                 960
Ala Ala Ala Arg Ser Leu Gly Asn Asn Lys Val Gln Val Gly Phe Ala
                965                 970                 975
Asp Val Gln Ala Gly Ala Thr Ile Thr Val Tyr Asp Asn Pro Asn Ser
            980                 985                 990
Gln Thr Pro Leu Ala Thr Leu Lys Ser Glu Val Gly Gly Asp Leu Ala
            995                1000                1005
Ser Ala Pro Leu Asp Leu Thr Asn Gln Ser Gly Leu Leu Tyr Tyr
            1010                1015                1020
Arg Thr Gln Leu Pro Gly Lys Glu Ile Ser Asn Val Leu Ala Val
            1025                1030                1035
Ser Val Pro Lys Asp Asp Arg Ile Lys Ser Val Ser Leu Glu
            1040                1045                1050
Thr Gly Pro Lys Lys Thr Ser Tyr Ala Glu Gly Glu Asp Leu Asp
            1055                1060                1065
Leu Arg Gly Gly Val Leu Arg Val Gln Tyr Glu Gly Gly Thr Glu
            1070                1075                1080
Asp Glu Leu Ile Arg Leu Thr His Ala Gly Val Ser Val Ser Gly
            1085                1090                1095
Phe Asp Thr His His Lys Gly Glu Gln Asn Leu Thr Leu Gln Tyr
            1100                1105                1110
Leu Gly Gln Pro Val Asn Ala Asn Leu Ser Val Thr Val Thr Gly
            1115                1120                1125
Gln Asp Glu Ala Ser Pro Lys Thr Ile Leu Gly Ile Glu Val Ser
            1130                1135                1140
Gln Lys Pro Lys Lys Asp Tyr Leu Val Gly Asp Ser Leu Asp Leu
            1145                1150                1155
Ser Glu Gly Arg Phe Ala Val Ala Tyr Ser Asn Asp Thr Met Glu
            1160                1165                1170
Glu His Ser Phe Thr Asp Glu Gly Val Glu Ile Ser Gly Tyr Asp
            1175                1180                1185
Ala Gln Lys Thr Gly Arg Gln Thr Leu Thr Leu Arg Tyr Gln Gly
            1190                1195                1200
His Glu Val Asn Phe Asp Val Leu Val Ser Pro Lys Ala Ala Leu
            1205                1210                1215
Asn Asp Glu Tyr Leu Lys Gln Lys Leu Ala Glu Val Glu Ala Ala
            1220                1225                1230
Lys Asn Lys Val Val Tyr Asn Phe Ala Ser Pro Glu Val Lys Glu
            1235                1240                1245
Ala Phe Leu Lys Ala Ile Glu Ala Ala Glu Gln Val Leu Lys Asp
            1250                1255                1260
His Glu Ile Ser Thr Gln Asp Gln Val Asn Asp Arg Leu Asn Lys
            1265                1270                1275
Leu Thr Glu Ala His Lys Ala Leu Asn Gly Gln Glu Lys Phe Lys
            1280                1285                1290
```

```
Glu Glu Lys Thr Glu Leu Asp Arg Leu Thr Gly Glu Val Gln Glu
    1295                1300                1305

Leu Leu Asp Ala Lys Pro Asn His Pro Ser Gly Ser Ala Leu Ala
1310                1315                1320

Pro Leu Leu Glu Lys Asn Lys Val Leu Val Glu Lys Val Asp Leu
    1325                1330                1335

Ser Pro Glu Glu Leu Ala Thr Ala Lys Gln Ser Leu Lys Asp Leu
    1340                1345                1350

Val Ala Leu Leu Lys Glu Asp Lys Pro Ala Val Phe Ser Asp Ser
    1355                1360                1365

Lys Thr Gly Val Glu Val His Phe Ser Asn Lys Glu Lys Thr Val
    1370                1375                1380

Ile Lys Gly Leu Lys Val Glu Arg Val Gln Ala Ser Ala Glu Glu
    1385                1390                1395

Lys Lys Tyr Phe Ala Gly Glu Asp Ala His Val Phe Glu Ile Glu
    1400                1405                1410

Gly Leu Asp Glu Lys Gly Gln Asp Val Asp Leu Ser Tyr Ala Ser
    1415                1420                1425

Ile Val Lys Ile Pro Ile Glu Lys Asp Lys Lys Val Lys Lys Val
    1430                1435                1440

Phe Phe Leu Pro Glu Gly Lys Glu Ala Val Glu Leu Ala Phe Glu
    1445                1450                1455

Gln Thr Asp Ser His Val Ile Phe Thr Ala Pro His Phe Thr His
    1460                1465                1470

Tyr Ala Phe Val Tyr Glu Ser Ala Glu Lys Pro Gln Pro Ala Lys
    1475                1480                1485

Pro Ala Pro Gln Asn Lys Val Leu Pro Lys Pro Thr Tyr Gln Pro
    1490                1495                1500

Ala Ser Asp Gln Gln Lys Ala Pro Lys Leu Glu Val Gln Glu Glu
    1505                1510                1515

Lys Val Ala Phe His Arg Gln Glu His Glu Asn Ala Glu Met Leu
    1520                1525                1530

Val Gly Glu Gln Arg Val Ile Ile Gln Gly Arg Asp Gly Leu Leu
    1535                1540                1545

Arg His Val Phe Glu Val Asp Glu Asn Gly Gln Arg Arg Leu Arg
    1550                1555                1560

Ser Thr Glu Val Ile Gln Glu Ala Ile Pro Glu Ile Val Glu Ile
    1565                1570                1575

Gly Thr Lys Val Lys Thr Val Pro Ala Val Val Ala Thr Gln Glu
    1580                1585                1590

Lys Pro Ala Gln Asn Thr Ala Val Lys Ser Glu Glu Ala Ser Lys
    1595                1600                1605

Gln Leu Pro Asn Thr Gly Thr Ala Asp Ala Asn Glu Ala Leu Ile
    1610                1615                1620

Ala Gly Leu Ala Ser Leu Gly Leu Ala Ser Leu Ala Leu Thr Leu
    1625                1630                1635

Arg Arg Lys Arg Glu Asp Lys Asp
    1640                1645

<210> SEQ ID NO 9
<211> LENGTH: 1646
<212> TYPE: PRT
<213> ORGANISM: Artificial Sequence
<220> FEATURE:
```

<223> OTHER INFORMATION: SYNTHETIC CONSTRUCT

<400> SEQUENCE: 9

```
Met Lys Asn Pro Phe Phe Glu Arg Arg Cys Arg Tyr Ser Ile Arg Lys
1               5                   10                  15
Leu Ser Val Gly Ala Cys Ser Leu Met Ile Gly Ala Val Leu Phe Val
            20                  25                  30
Gly Pro Ala Leu Ala Glu Glu Thr Ala Val Pro Glu Asn Ser Gly Ala
        35                  40                  45
Asn Thr Glu Leu Val Ser Gly Glu Ser Glu His Ser Thr Asn Glu Ala
    50                  55                  60
Asp Lys Gln Asn Glu Gly Glu His Thr Arg Glu Asn Lys Leu Glu Lys
65                  70                  75                  80
Ala Glu Gly Val Ala Thr Ala Ser Glu Thr Ala Glu Ala Ala Ser Ala
                85                  90                  95
Ala Lys Pro Glu Glu Lys Ala Gly Glu Val Val Ala Glu Thr Pro Ser
            100                 105                 110
Ala Glu Ala Lys Pro Lys Ser Asp Lys Glu Thr Glu Ala Lys Pro Glu
        115                 120                 125
Ala Thr Asn Gln Gly Asp Glu Ser Lys Pro Ala Ala Glu Ala Asn Lys
    130                 135                 140
Thr Glu Lys Glu Val Gln Pro Asp Val Pro Lys Asn Thr Glu Lys Thr
145                 150                 155                 160
Leu Lys Pro Lys Glu Ile Lys Phe Asn Ser Trp Glu Leu Leu Lys
                165                 170                 175
Trp Glu Pro Gly Ala Arg Glu Asp Ala Ile Asn Arg Gly Ser Val
            180                 185                 190
Val Leu Ala Ser Arg Arg Thr Gly His Leu Val Asn Gly Lys Ala Ser
        195                 200                 205
Lys Glu Ala Lys Val Gln Ala Leu Ser Asn Thr Asn Ser Lys Ala Lys
    210                 215                 220
Asp His Ala Ser Val Gly Gly Glu Glu Phe Lys Ala Tyr Ala Phe Asp
225                 230                 235                 240
Tyr Trp Gln Tyr Leu Asp Ser Met Val Phe Trp Glu Gly Leu Val Pro
                245                 250                 255
Thr Pro Asp Val Ile Asp Ala Gly His Arg Asn Gly Val Pro Val Tyr
            260                 265                 270
Gly Thr Leu Phe Phe Asn Trp Ser Asn Ser Ile Ala Asp Gln Glu Arg
        275                 280                 285
Phe Ala Glu Ala Leu Lys Gln Asp Ala Asp Gly Ser Phe Pro Ile Ala
    290                 295                 300
Arg Lys Leu Val Asp Met Ala Lys Tyr Tyr Gly Tyr Asp Gly Tyr Phe
305                 310                 315                 320
Ile Gln Gln Glu Thr Thr Gly Asp Leu Val Lys Pro Leu Gly Glu Lys
                325                 330                 335
Met Arg Gln Phe Met Leu Tyr Ser Lys Glu Tyr Ala Ala Lys Val Asn
            340                 345                 350
His Pro Ile Lys Tyr Ser Trp Tyr Asp Ala Met Thr Tyr Asn Tyr Gly
        355                 360                 365
Arg Tyr His Gln Asp Gly Leu Gly Glu Tyr Asn Tyr Gln Phe Met Gln
    370                 375                 380
Pro Glu Gly Asp Lys Val Pro Ala Asp Asn Phe Phe Ala Asn Phe Asn
385                 390                 395                 400
```

```
Trp Asp Lys Ala Lys Asn Asp Tyr Thr Ile Ala Thr Ala Asn Trp Ile
            405                 410                 415
Gly Arg Asn Pro Tyr Asp Val Phe Ala Gly Leu Glu Leu Gln Gln Gly
        420                 425                 430
Gly Ser Tyr Lys Thr Lys Val Lys Trp Asn Asp Ile Leu Asp Glu Asn
    435                 440                 445
Gly Lys Leu Arg Leu Ser Leu Gly Leu Phe Ala Pro Asp Thr Ile Thr
450                 455                 460
Ser Leu Gly Lys Thr Gly Glu Asp Tyr His Lys Asn Glu Asp Ile Phe
465                 470                 475                 480
Phe Thr Gly Tyr Gln Gly Asp Pro Thr Gly Gln Lys Pro Gly Asp Lys
                485                 490                 495
Asp Trp Tyr Gly Ile Ala Asn Leu Val Ala Asp Arg Thr Pro Ala Val
            500                 505                 510
Gly Asn Thr Phe Thr Thr Ser Phe Asn Thr Gly His Gly Lys Lys Trp
        515                 520                 525
Phe Val Asp Gly Lys Val Ser Lys Asp Ser Glu Trp Asn Tyr Arg Ser
    530                 535                 540
Val Ser Gly Val Leu Pro Thr Trp Arg Trp Gln Thr Ser Thr Gly
545                 550                 555                 560
Glu Lys Leu Arg Ala Glu Tyr Asp Phe Thr Asp Ala Tyr Asn Gly Gly
                565                 570                 575
Asn Ser Leu Lys Phe Ser Gly Asp Val Ala Gly Lys Thr Asp Gln Asp
            580                 585                 590
Val Arg Leu Tyr Ser Thr Lys Leu Glu Val Thr Glu Lys Thr Lys Leu
        595                 600                 605
Arg Val Ala His Lys Gly Gly Lys Gly Ser Lys Val Tyr Met Ala Phe
    610                 615                 620
Ser Thr Thr Pro Asp Tyr Lys Phe Asp Asp Ala Asp Ala Trp Lys Glu
625                 630                 635                 640
Leu Thr Leu Ser Asp Asn Trp Thr Asn Glu Glu Phe Asp Leu Ser Ser
                645                 650                 655
Leu Ala Gly Lys Thr Ile Tyr Ala Val Lys Leu Phe Phe Glu His Glu
            660                 665                 670
Gly Ala Val Lys Asp Tyr Gln Phe Asn Leu Gly Gln Leu Thr Ile Ser
        675                 680                 685
Asp Asn His Gln Glu Pro Gln Ser Pro Thr Ser Phe Ser Val Val Lys
    690                 695                 700
Gln Ser Leu Lys Asn Ala Gln Glu Ala Glu Ala Val Gln Phe Lys
705                 710                 715                 720
Gly Asn Lys Asp Ala Asp Phe Tyr Glu Val Tyr Glu Lys Asp Gly Asp
                725                 730                 735
Ser Trp Lys Leu Leu Thr Gly Ser Ser Thr Thr Ile Tyr Leu Pro
            740                 745                 750
Lys Val Ser Arg Ser Ala Ser Ala Gln Gly Thr Thr Gln Glu Leu Lys
        755                 760                 765
Val Val Ala Val Gly Lys Asn Gly Val Arg Ser Glu Ala Ala Thr Thr
    770                 775                 780
Thr Phe Asp Trp Gly Met Thr Val Lys Asp Thr Ser Leu Pro Lys Pro
785                 790                 795                 800
Leu Ala Glu Asn Ile Val Pro Gly Ala Thr Val Ile Asp Ser Thr Phe
                805                 810                 815
Pro Lys Thr Glu Gly Gly Glu Gly Ile Glu Gly Met Leu Asn Gly Thr
```

```
            820                 825                 830
Ile Thr Ser Leu Ser Asp Lys Trp Ser Ser Ala Gln Leu Ser Gly Ser
                835                 840                 845

Val Asp Ile Arg Leu Thr Lys Pro Arg Thr Val Val Arg Trp Val Met
850                 855                 860

Asp His Ala Gly Ala Gly Glu Ser Val Asn Asp Gly Leu Met Asn
865                 870                 875                 880

Thr Lys Asp Phe Asp Leu Tyr Tyr Lys Asp Ala Asp Gly Glu Trp Lys
                885                 890                 895

Leu Ala Lys Glu Val Arg Gly Asn Lys Ala His Val Thr Asp Ile Thr
                900                 905                 910

Leu Asp Lys Pro Ile Thr Ala Gln Asp Trp Arg Leu Asn Val Val Thr
                915                 920                 925

Ser Asp Asn Gly Thr Pro Trp Lys Ala Ile Arg Ile Tyr Asn Trp Lys
                930                 935                 940

Met Tyr Glu Lys Leu Asp Thr Glu Ser Val Asn Ile Pro Met Ala Lys
945                 950                 955                 960

Ala Ala Ala Arg Ser Leu Gly Asn Asn Lys Val Gln Val Gly Phe Ala
                965                 970                 975

Asp Val Gln Ala Gly Ala Thr Ile Thr Val Tyr Asp Asn Pro Asn Ser
                980                 985                 990

Gln Thr Pro Leu Ala Thr Leu Lys Ser Glu Val Gly Gly Asp Leu Ala
                995                 1000                1005

Ser Ala Pro Leu Asp Leu Thr Asn Gln Ser Gly Leu Leu Tyr Tyr
                1010                1015                1020

Arg Thr Gln Leu Pro Gly Lys Glu Ile Ser Asn Val Leu Ala Val
                1025                1030                1035

Ser Val Pro Lys Asp Asp Arg Arg Ile Lys Ser Val Ser Leu Glu
                1040                1045                1050

Thr Gly Pro Lys Lys Thr Ser Tyr Ala Glu Gly Glu Asp Leu Asp
                1055                1060                1065

Leu Arg Gly Gly Val Leu Arg Val Gln Tyr Glu Gly Gly Thr Glu
                1070                1075                1080

Asp Glu Leu Ile Arg Leu Thr His Ala Gly Val Ser Val Ser Gly
                1085                1090                1095

Phe Asp Thr His His Lys Gly Glu Gln Asn Leu Thr Leu Gln Tyr
                1100                1105                1110

Leu Gly Gln Pro Val Asn Ala Asn Leu Ser Val Thr Val Thr Gly
                1115                1120                1125

Gln Asp Glu Ala Ser Pro Lys Thr Ile Leu Gly Ile Glu Val Ser
                1130                1135                1140

Gln Lys Pro Lys Lys Asp Tyr Leu Val Gly Asp Ser Leu Asp Leu
                1145                1150                1155

Ser Glu Gly Arg Phe Ala Val Ala Tyr Ser Asn Asp Thr Met Glu
                1160                1165                1170

Glu His Ser Phe Thr Asp Glu Gly Val Glu Ile Ser Gly Tyr Asp
                1175                1180                1185

Ala Gln Lys Thr Gly Arg Gln Thr Leu Thr Leu Arg Tyr Gln Gly
                1190                1195                1200

His Glu Val Asn Phe Asp Val Leu Val Ser Pro Lys Ala Ala Leu
                1205                1210                1215

Asn Asp Glu Tyr Leu Lys Gln Lys Leu Ala Glu Val Glu Ala Ala
                1220                1225                1230
```

```
Lys Asn Lys Val Val Tyr Asn Phe Ala Ser Pro Glu Val Lys Glu
1235                1240                1245

Ala Phe Leu Lys Ala Ile Glu Ala Ala Glu Gln Val Leu Lys Asp
1250                1255                1260

His Glu Ile Ser Thr Gln Asp Gln Val Asn Asp Arg Leu Asn Lys
1265                1270                1275

Leu Thr Glu Ala His Lys Ala Leu Asn Gly Gln Glu Lys Phe Lys
1280                1285                1290

Glu Glu Lys Thr Glu Leu Asp Arg Leu Thr Gly Glu Val Gln Glu
1295                1300                1305

Leu Leu Asp Ala Lys Pro Asn His Pro Ser Gly Ser Ala Leu Ala
1310                1315                1320

Pro Leu Leu Glu Lys Asn Lys Val Leu Val Glu Lys Val Asp Leu
1325                1330                1335

Ser Pro Glu Glu Leu Ala Thr Ala Lys Gln Ser Leu Lys Asp Leu
1340                1345                1350

Val Ala Leu Leu Lys Glu Asp Lys Pro Ala Val Phe Ser Asp Ser
1355                1360                1365

Lys Thr Gly Val Glu Val His Phe Ser Asn Lys Glu Lys Thr Val
1370                1375                1380

Ile Lys Gly Leu Lys Val Glu Arg Val Gln Ala Ser Ala Glu Glu
1385                1390                1395

Lys Lys Tyr Phe Ala Gly Glu Asp Ala His Val Phe Glu Ile Glu
1400                1405                1410

Gly Leu Asp Glu Lys Gly Gln Asp Val Asp Leu Ser Tyr Ala Ser
1415                1420                1425

Ile Val Lys Ile Pro Ile Glu Lys Asp Lys Lys Val Lys Lys Val
1430                1435                1440

Phe Phe Leu Pro Glu Gly Lys Glu Ala Val Glu Leu Ala Phe Glu
1445                1450                1455

Gln Thr Asp Ser His Val Ile Phe Thr Ala Pro His Phe Thr His
1460                1465                1470

Tyr Ala Phe Val Tyr Glu Ser Ala Glu Lys Pro Gln Pro Ala Lys
1475                1480                1485

Pro Ala Pro Gln Asn Lys Val Leu Pro Lys Pro Thr Tyr Gln Pro
1490                1495                1500

Ala Ser Asp Gln Gln Lys Ala Pro Lys Leu Glu Val Gln Glu Glu
1505                1510                1515

Lys Val Ala Phe His Arg Gln Glu His Glu Asn Ala Glu Met Leu
1520                1525                1530

Val Gly Glu Gln Arg Val Ile Ile Gln Gly Arg Asp Gly Leu Leu
1535                1540                1545

Arg His Val Phe Glu Val Asp Glu Asn Gly Gln Arg Arg Leu Arg
1550                1555                1560

Ser Thr Glu Val Ile Gln Glu Ala Ile Pro Glu Ile Val Glu Ile
1565                1570                1575

Gly Thr Lys Val Lys Thr Val Pro Ala Val Val Ala Thr Gln Glu
1580                1585                1590

Lys Pro Ala Gln Asn Thr Ala Val Lys Ser Glu Glu Ala Ser Lys
1595                1600                1605

Gln Leu Pro Asn Thr Gly Thr Ala Asp Ala Asn Glu Ala Leu Ile
1610                1615                1620
```

```
Ala Gly Leu Ala Ser Leu Gly Leu Ala Ser Leu Ala Leu Thr Leu
    1625                1630                1635
Arg Arg Lys Arg Glu Asp Lys Asp
    1640                1645

<210> SEQ ID NO 10
<211> LENGTH: 289
<212> TYPE: PRT
<213> ORGANISM: Artificial Sequence
<220> FEATURE:
<223> OTHER INFORMATION: SYNTHETIC CONSTRUCT

<400> SEQUENCE: 10

Ala Val Thr Gly Thr Thr Lys Ala Asn Ile Lys Leu Phe Ser Phe Thr
1               5                   10                  15

Glu Val Asn Asp Thr Asn Pro Leu Asn Asn Leu Asn Phe Thr Leu Lys
            20                  25                  30

Asn Ser Gly Lys Pro Leu Val Asp Met Val Val Leu Phe Ser Ala Asn
        35                  40                  45

Ile Asn Tyr Asp Ala Ala Asn Asp Lys Val Phe Val Ser Asn Asn Pro
    50                  55                  60

Asn Val Gln His Leu Leu Thr Asn Arg Ala Lys Tyr Leu Lys Pro Leu
65                  70                  75                  80

Gln Asp Lys Gly Ile Lys Val Ile Leu Ser Ile Leu Gly Asn His Asp
                85                  90                  95

Arg Ser Gly Ile Ala Asn Leu Ser Thr Ala Arg Ala Lys Ala Phe Ala
            100                 105                 110

Gln Glu Leu Lys Asn Thr Cys Asp Leu Tyr Asn Leu Asp Gly Val Phe
        115                 120                 125

Phe Ala Asp Glu Tyr Ser Ala Tyr Gln Thr Pro Pro Ser Gly Phe
    130                 135                 140

Val Thr Pro Ser Asn Asn Ala Ala Arg Leu Ala Tyr Glu Thr Lys
145                 150                 155                 160

Gln Ala Met Pro Asn Lys Leu Val Thr Val Tyr Tyr Ser Arg Thr
                165                 170                 175

Ser Ser Phe Pro Thr Ala Val Asp Gly Val Asn Ala Gly Ser Tyr Val
            180                 185                 190

Asp Tyr Ala Ile His Asp Tyr Gly Gly Ser Tyr Asp Leu Ala Thr Asn
        195                 200                 205

Tyr Pro Gly Leu Ala Lys Ser Gly Met Val Met Ser Ser Gln Glu Phe
    210                 215                 220

Asn Gln Gly Arg Tyr Ala Thr Ala Gln Ala Leu Arg Asn Ile Val Thr
225                 230                 235                 240

Lys Gly Tyr Gly Gly His Met Ile Phe Ala Met Asp Pro Asn Arg Ser
                245                 250                 255

Asn Phe Thr Ser Gly Gln Leu Pro Ala Leu Lys Leu Ile Ala Lys Glu
            260                 265                 270

Leu Tyr Gly Asp Glu Leu Val Tyr Ser Asn Thr Pro Tyr Ser Lys Asp
        275                 280                 285

Trp

<210> SEQ ID NO 11
<211> LENGTH: 1646
<212> TYPE: PRT
<213> ORGANISM: Streptococcus pneumoniae

<400> SEQUENCE: 11
```

```
Met Lys Asn Pro Phe Phe Glu Arg Arg Cys Arg Tyr Ser Ile Arg Lys
1               5                   10                  15

Leu Ser Val Gly Ala Cys Ser Leu Met Ile Gly Ala Val Leu Phe Val
            20                  25                  30

Gly Pro Ala Leu Ala Glu Glu Thr Ala Val Pro Glu Asn Ser Gly Ala
        35                  40                  45

Asn Thr Glu Leu Val Ser Gly Glu Ser Glu His Ser Thr Asn Glu Ala
    50                  55                  60

Asp Lys Gln Asn Glu Gly Glu His Thr Arg Glu Asn Lys Leu Glu Lys
65                  70                  75                  80

Ala Glu Gly Val Ala Thr Ala Ser Glu Thr Ala Glu Ala Ala Ser Ala
                85                  90                  95

Ala Lys Pro Glu Glu Lys Ala Gly Glu Val Val Ala Glu Thr Pro Ser
            100                 105                 110

Ala Glu Ala Lys Pro Lys Ser Asp Lys Glu Thr Glu Ala Lys Pro Glu
        115                 120                 125

Ala Thr Asn Gln Gly Asp Glu Ser Lys Pro Ala Ala Glu Ala Asn Lys
    130                 135                 140

Thr Glu Lys Glu Val Gln Pro Asp Val Pro Lys Asn Thr Glu Lys Thr
145                 150                 155                 160

Leu Lys Pro Lys Glu Ile Lys Phe Asn Ser Trp Glu Leu Leu Lys
                165                 170                 175

Trp Glu Pro Gly Ala Arg Glu Asp Ala Ile Asn Arg Gly Ser Val
                180                 185                 190

Val Leu Ala Ser Arg Arg Thr Gly His Leu Val Asn Glu Lys Ala Ser
        195                 200                 205

Lys Glu Ala Lys Val Gln Ala Leu Ser Asn Thr Asn Ser Lys Ala Lys
    210                 215                 220

Asp His Ala Ser Val Gly Gly Glu Glu Phe Lys Ala Tyr Ala Phe Asp
225                 230                 235                 240

Tyr Trp Gln Tyr Leu Asp Ser Met Val Phe Trp Glu Gly Leu Val Pro
                245                 250                 255

Thr Pro Asp Val Ile Asp Ala Gly His Arg Asn Gly Val Pro Val Tyr
            260                 265                 270

Gly Thr Leu Phe Phe Asn Trp Ser Asn Ser Ile Ala Asp Gln Glu Arg
        275                 280                 285

Phe Ala Glu Ala Leu Lys Gln Asp Ala Asp Gly Ser Phe Pro Ile Ala
    290                 295                 300

Arg Lys Leu Val Asp Met Ala Lys Tyr Tyr Gly Tyr Asp Gly Tyr Phe
305                 310                 315                 320

Ile Asn Gln Glu Thr Thr Gly Asp Leu Val Lys Pro Leu Gly Glu Lys
                325                 330                 335

Met Arg Gln Phe Met Leu Tyr Ser Lys Glu Tyr Ala Ala Lys Val Asn
            340                 345                 350

His Pro Ile Lys Tyr Ser Trp Tyr Asp Ala Met Thr Tyr Asn Tyr Gly
        355                 360                 365

Arg Tyr His Gln Asp Gly Leu Gly Glu Tyr Asn Tyr Gln Phe Met Gln
    370                 375                 380

Pro Glu Gly Asp Lys Val Pro Ala Asp Asn Phe Ala Asn Phe Asn
385                 390                 395                 400

Trp Asp Lys Ala Lys Asn Asp Tyr Thr Ile Ala Thr Ala Asn Trp Ile
                405                 410                 415
```

```
Gly Arg Asn Pro Tyr Asp Val Phe Ala Gly Leu Glu Leu Gln Gln Gly
                420                 425                 430

Gly Ser Tyr Lys Thr Lys Val Lys Trp Asn Asp Ile Leu Asp Glu Asn
            435                 440                 445

Gly Lys Leu Arg Leu Ser Leu Gly Leu Phe Ala Pro Asp Thr Ile Thr
        450                 455                 460

Ser Leu Gly Lys Thr Gly Glu Asp Tyr His Lys Asn Glu Asp Ile Phe
465                 470                 475                 480

Phe Thr Gly Tyr Gln Gly Asp Pro Thr Gly Gln Lys Pro Gly Asp Lys
                485                 490                 495

Asp Trp Tyr Gly Ile Ala Asn Leu Val Ala Asp Arg Thr Pro Ala Val
            500                 505                 510

Gly Asn Thr Phe Thr Thr Ser Phe Asn Thr Gly His Gly Lys Lys Trp
        515                 520                 525

Phe Val Asp Gly Lys Val Ser Lys Asp Ser Glu Trp Asn Tyr Arg Ser
530                 535                 540

Val Ser Gly Val Leu Pro Thr Trp Arg Trp Gln Thr Ser Thr Gly
545                 550                 555                 560

Glu Lys Leu Arg Ala Glu Tyr Asp Phe Thr Asp Ala Tyr Asn Gly Gly
                565                 570                 575

Asn Ser Leu Lys Phe Ser Gly Asp Val Ala Gly Lys Thr Asp Gln Asp
            580                 585                 590

Val Arg Leu Tyr Ser Thr Lys Leu Glu Val Thr Glu Lys Thr Lys Leu
        595                 600                 605

Arg Val Ala His Lys Gly Lys Gly Ser Lys Val Tyr Met Ala Phe
610                 615                 620

Ser Thr Thr Pro Asp Tyr Lys Phe Asp Asp Ala Asp Ala Trp Lys Glu
625                 630                 635                 640

Leu Thr Leu Ser Asp Asn Trp Thr Asn Glu Glu Phe Asp Leu Ser Ser
                645                 650                 655

Leu Ala Gly Lys Thr Ile Tyr Ala Val Lys Leu Phe Phe Glu His Glu
            660                 665                 670

Gly Ala Val Lys Asp Tyr Gln Phe Asn Leu Gly Gln Leu Thr Ile Ser
        675                 680                 685

Asp Asn His Gln Glu Pro Gln Ser Pro Thr Ser Phe Ser Val Val Lys
690                 695                 700

Gln Ser Leu Lys Asn Ala Gln Glu Ala Glu Ala Val Val Gln Phe Lys
705                 710                 715                 720

Gly Asn Lys Asp Ala Asp Phe Tyr Glu Val Tyr Glu Lys Asp Gly Asp
                725                 730                 735

Ser Trp Lys Leu Leu Thr Gly Ser Ser Thr Thr Ile Tyr Leu Pro
            740                 745                 750

Lys Val Ser Arg Ser Ala Ser Ala Gln Gly Thr Thr Gln Glu Leu Lys
        755                 760                 765

Val Val Ala Val Gly Lys Asn Gly Val Arg Ser Glu Ala Ala Thr Thr
770                 775                 780

Thr Phe Asp Trp Gly Met Thr Val Lys Asp Thr Ser Leu Pro Lys Pro
785                 790                 795                 800

Leu Ala Glu Asn Ile Val Pro Gly Ala Thr Val Ile Asp Ser Thr Phe
                805                 810                 815

Pro Lys Thr Glu Gly Gly Glu Gly Ile Glu Gly Met Leu Asn Gly Thr
            820                 825                 830

Ile Thr Ser Leu Ser Asp Lys Trp Ser Ser Ala Gln Leu Ser Gly Ser
```

```
              835            840            845
Val Asp Ile Arg Leu Thr Lys Pro Arg Thr Val Val Arg Trp Val Met
        850            855            860

Asp His Ala Gly Ala Gly Gly Glu Ser Val Asn Asp Gly Leu Met Asn
865            870            875            880

Thr Lys Asp Phe Asp Leu Tyr Tyr Lys Asp Ala Asp Gly Glu Trp Lys
                885            890            895

Leu Ala Lys Glu Val Arg Gly Asn Lys Ala His Val Thr Asp Ile Thr
            900            905            910

Leu Asp Lys Pro Ile Thr Ala Gln Asp Trp Arg Leu Asn Val Val Thr
            915            920            925

Ser Asp Asn Gly Thr Pro Trp Lys Ala Ile Arg Ile Tyr Asn Trp Lys
        930            935            940

Met Tyr Glu Lys Leu Asp Thr Glu Ser Val Asn Ile Pro Met Ala Lys
945            950            955            960

Ala Ala Ala Arg Ser Leu Gly Asn Asn Lys Val Gln Val Gly Phe Ala
            965            970            975

Asp Val Gln Ala Gly Ala Thr Ile Thr Val Tyr Asp Asn Pro Asn Ser
        980            985            990

Gln Thr Pro Leu Ala Thr Leu Lys Ser Glu Val Gly Gly Asp Leu Ala
        995           1000           1005

Ser Ala Pro Leu Asp Leu Thr Asn Gln Ser Gly Leu Leu Tyr Tyr
      1010           1015           1020

Arg Thr Gln Leu Pro Gly Lys Glu Ile Ser Asn Val Leu Ala Val
      1025           1030           1035

Ser Val Pro Lys Asp Asp Arg Arg Ile Lys Ser Val Ser Leu Glu
      1040           1045           1050

Thr Gly Pro Lys Lys Thr Ser Tyr Ala Glu Gly Glu Asp Leu Asp
      1055           1060           1065

Leu Arg Gly Gly Val Leu Arg Val Gln Tyr Glu Gly Gly Thr Glu
      1070           1075           1080

Asp Glu Leu Ile Arg Leu Thr His Ala Gly Val Ser Val Ser Gly
      1085           1090           1095

Phe Asp Thr His His Lys Gly Glu Gln Asn Leu Thr Leu Gln Tyr
      1100           1105           1110

Leu Gly Gln Pro Val Asn Ala Asn Leu Ser Val Thr Val Thr Gly
      1115           1120           1125

Gln Asp Glu Ala Ser Pro Lys Thr Ile Leu Gly Ile Glu Val Ser
      1130           1135           1140

Gln Lys Pro Lys Lys Asp Tyr Leu Val Gly Asp Ser Leu Asp Leu
      1145           1150           1155

Ser Glu Gly Arg Phe Ala Val Ala Tyr Ser Asn Asp Thr Met Glu
      1160           1165           1170

Glu His Ser Phe Thr Asp Glu Gly Val Glu Ile Ser Gly Tyr Asp
      1175           1180           1185

Ala Gln Lys Thr Gly Arg Gln Thr Leu Thr Leu Arg Tyr Gln Gly
      1190           1195           1200

His Glu Val Asn Phe Asp Val Leu Val Ser Pro Lys Ala Ala Leu
      1205           1210           1215

Asn Asp Glu Tyr Leu Lys Gln Lys Leu Ala Glu Val Glu Ala Ala
      1220           1225           1230

Lys Asn Lys Val Val Tyr Asn Phe Ala Ser Pro Glu Val Lys Glu
      1235           1240           1245
```

-continued

```
Ala Phe Leu Lys Ala Ile Glu Ala Ala Glu Gln Val Leu Lys Asp
        1250                1255                1260

His Glu Ile Ser Thr Gln Asp Gln Val Asn Asp Arg Leu Asn Lys
        1265                1270                1275

Leu Thr Glu Ala His Lys Ala Leu Asn Gly Gln Glu Lys Phe Lys
        1280                1285                1290

Glu Glu Lys Thr Glu Leu Asp Arg Leu Thr Gly Glu Val Gln Glu
        1295                1300                1305

Leu Leu Asp Ala Lys Pro Asn His Pro Ser Gly Ser Ala Leu Ala
        1310                1315                1320

Pro Leu Leu Glu Lys Asn Lys Val Leu Val Glu Lys Val Asp Leu
        1325                1330                1335

Ser Pro Glu Glu Leu Ala Thr Ala Lys Gln Ser Leu Lys Asp Leu
        1340                1345                1350

Val Ala Leu Leu Lys Glu Asp Lys Pro Ala Val Phe Ser Asp Ser
        1355                1360                1365

Lys Thr Gly Val Glu Val His Phe Ser Asn Lys Glu Lys Thr Val
        1370                1375                1380

Ile Lys Gly Leu Lys Val Glu Arg Val Gln Ala Ser Ala Glu Glu
        1385                1390                1395

Lys Lys Tyr Phe Ala Gly Glu Asp Ala His Val Phe Glu Ile Glu
        1400                1405                1410

Gly Leu Asp Glu Lys Gly Gln Asp Val Asp Leu Ser Tyr Ala Ser
        1415                1420                1425

Ile Val Lys Ile Pro Ile Glu Lys Asp Lys Lys Val Lys Lys Val
        1430                1435                1440

Phe Phe Leu Pro Glu Gly Lys Glu Ala Val Glu Leu Ala Phe Glu
        1445                1450                1455

Gln Thr Asp Ser His Val Ile Phe Thr Ala Pro His Phe Thr His
        1460                1465                1470

Tyr Ala Phe Val Tyr Glu Ser Ala Glu Lys Pro Gln Pro Ala Lys
        1475                1480                1485

Pro Ala Pro Gln Asn Lys Val Leu Pro Lys Pro Thr Tyr Gln Pro
        1490                1495                1500

Ala Ser Asp Gln Gln Lys Ala Pro Lys Leu Glu Val Gln Glu Glu
        1505                1510                1515

Lys Val Ala Phe His Arg Gln Glu His Glu Asn Ala Glu Met Leu
        1520                1525                1530

Val Gly Glu Gln Arg Val Ile Ile Gln Gly Arg Asp Gly Leu Leu
        1535                1540                1545

Arg His Val Phe Glu Val Asp Glu Asn Gly Gln Arg Arg Leu Arg
        1550                1555                1560

Ser Thr Glu Val Ile Gln Glu Ala Ile Pro Glu Ile Val Glu Ile
        1565                1570                1575

Gly Thr Lys Val Lys Thr Val Pro Ala Val Val Ala Thr Gln Glu
        1580                1585                1590

Lys Pro Ala Gln Asn Thr Ala Val Lys Ser Glu Glu Ala Ser Lys
        1595                1600                1605

Gln Leu Pro Asn Thr Gly Thr Ala Asp Ala Asn Glu Ala Leu Ile
        1610                1615                1620

Ala Gly Leu Ala Ser Leu Gly Leu Ala Ser Leu Ala Leu Thr Leu
        1625                1630                1635
```

Arg Arg Lys Arg Glu Asp Lys Asp
    1640             1645

<210> SEQ ID NO 12
<211> LENGTH: 35
<212> TYPE: DNA
<213> ORGANISM: Artificial Sequence
<220> FEATURE:
<223> OTHER INFORMATION: SYNTHETIC CONSTRUCT

<400> SEQUENCE: 12
tatatacata tggagtctaa accagcagca gaagc                        35

<210> SEQ ID NO 13
<211> LENGTH: 36
<212> TYPE: DNA
<213> ORGANISM: Artificial Sequence
<220> FEATURE:
<223> OTHER INFORMATION: SYNTHETIC CONSTRUCT

<400> SEQUENCE: 13
gcgcgcctcg agttcttctg tcatcttttg gaacgg                       36

<210> SEQ ID NO 14
<211> LENGTH: 4941
<212> TYPE: DNA
<213> ORGANISM: Streptococcus pneumoniae

<400> SEQUENCE: 14

| | |
|---|---:|
| atgaagaatc catttttga aagacgttgt cgttacagta ttcgtaagtt atcagtagga | 60 |
| gcctgctcgc tgatgattgg tgctgtttta tttgttggtc cagccttggc tgaagaaact | 120 |
| gcagttcctg aaaatagcgg agctaataca gagcttgttt caggagagag tgagcattcg | 180 |
| accaatgaag ctgataagca gaatgaaggg gaacatacta gagaaaacaa gctagaaaag | 240 |
| gcagaaggag tagcgacagc atctgaaact gcagaagcag ctagcgcagc taaaccagag | 300 |
| gaaaaagcag gtgaggtggt tgcagaaaca ccatctgcag aagcaaaacc taagtctgac | 360 |
| aaggaaacag aagcaaagcc cgaagcaact aaccaagggg atgagtctaa accagcagca | 420 |
| gaagctaata agactgaaaa agaagtccag ccagatgtcc ctaaaaatac agaaaaaaca | 480 |
| ttaaaaccaa aggaaatcaa atttaattct tgggaagaat tgttaaaatg gaaccaggt | 540 |
| gctcgtgaag atgatgctat taaccgcgga tctgttgtcc tcgcttcacg tcggacaggt | 600 |
| catttagtca tgaaaaagc tagcaaggaa gcaaaagttc aagccttatc aaacaccaat | 660 |
| tctaaagcaa aagaccatgc ttctgttggt ggagaagagt tcaaggccta tgcttttgac | 720 |
| tattggcaat atctagattc aatggtcttc tgggaaggtc tcgtaccaac tcctgacgtt | 780 |
| attgatgcag tcaccgtaa cggggttcct gtatacggta cactcttctt caactggtct | 840 |
| aatagtattg cagatcaaga agatttgct gaagctttga agcaagacgc agatggtagc | 900 |
| ttcccaattg cccgtaaatt ggtagacatg gccaagtatt atggctatga tggctatttc | 960 |
| atcaaccaag aaacaactgg agatttggtt aaacctcttg agaaaagat gcgccagttt | 1020 |
| atgctctata gcaaggaata tgctgctaag gtaaaccatc caatcaagta ttcttggtat | 1080 |
| gatgccatga cctataacta tggacgttac catcaagatg gtttgggaga atacaactac | 1140 |
| caattcatgc aaccagaagg agataaggtt ccggcagata acttctttgc taactttaac | 1200 |
| tgggataagg ctaaaaatga ttacactatt gcaactgcca actggattgg tcgtaatccc | 1260 |
| tatgatgtat ttgcaggttt ggaattgcaa cagggtggtt cctacaagac aaaggttaag | 1320 |

```
tggaatgaca ttttagacga aaatgggaaa ttgcgccttt ctcttggttt atttgcccca   1380
gataccatta caagtttagg aaaaactggt gaagattatc ataaaaatga agatatcttc   1440
tttacaggtt atcaaggaga ccccactggc caaaaaccag gtgacaaaga ttggtatggt   1500
attgctaacc tagttgcgga ccgtacgcca gcggtaggta atactttttac tacttctttt   1560 aatacaggtc atggtaaaaa atggttcgta gatggtaagg tttctaagga ttctgagtgg   1620
aattatcgtt cagtatcagg tgttcttcca acatggcgct ggtggcagac ttcaacaggg   1680
gaaaaacttc gtgcagaata tgattttaca gatgcctata atggcggaaa ttcccttaaa   1740
ttctctggtg atgtagccgg taagacagat caggatgtga gactttattc tactaagtta   1800
gaagtaactg agaagaccaa acttcgtgtt gcccacaagg gaggaaaagg ttctaaagtt   1860
tatatggcat tctctacaac tccagactac aaattcgatg atgcagatgc atggaaagag   1920 ctaaccctt ctgacaactg gacaaatgaa gaatttgatc tcagctcact agcaggtaaa   1980
accatctatg cagtcaaact attttttgag catgaaggtg ctgtaaaaga ttatcagttc   2040
aacctcggac aattaactat ctcggacaat caccaagagc acaatcgccc gacaagcttt   2100
tctgtagtga acaatctct taaaaatgcc caagaagcgg aagcagttgt gcaatttaaa   2160
ggcaacaagg atgcagattt ctatgaagtt tatgaaaaag atggagacag ctggaaatta   2220
ctaactggct catcttctac aactatttat ctaccaaaag ttagccgctc agcaagtgct   2280
cagggtacaa ctcaagaact gaaggttgta gcagtcggta aaaatggagt tcgttcagaa   2340
gctgcaacca caacctttga ttggggtatg actgtaaaag ataccagcct accaaaacca   2400
ctagctgaaa atatcgttcc aggtgcaaca gttattgata gtactttccc taagactgaa   2460
ggtggagaag gtattgaagg tatgttgaac ggtaccatta ctagcttgtc agataaatgg   2520
tcttcagctc agttgagtgg tagtgtggat attcgtttga ccaagccacg taccgttgtt   2580
agatgggtca tggatcatgc aggggctggt ggtgagtctg ttaacgatgg cttgatgaac   2640
accaaagact ttgacccttta ttataaagat gcagatggtg agtggaagct agctaaggaa   2700
gtccgtggca caaagcaca cgtgacagat atcactcttg ataaaccaat cactgctcaa   2760
gactggcgct tgaatgttgt cacttctgac aatggaactc catggaaggc tattcgtatc   2820
tataactgga aaatgtatga aaagcttgat actgagagtg tcaatattcc gatggccaag   2880
gctgcagccc gttctctagg caataacaag gtacaagttg gctttgcaga tgtacaggct   2940
ggagcaacta ttaccgttta tgataatcca aattctcaaa ctccgctcgc aaccttgaag   3000
agcgaagttg gaggagacct agcaagtgca ccattggatt tgacaaatca atctggtctt   3060
ctttattatc gtacccagtt gccaggcaag gaaattagta atgtcctagc agtttccgtt   3120
ccaaaagatg acagaagaat caagtcagtc agcctagaaa caggacctaa gaaaacaagc   3180
tacgccgaag gggaggattt ggaccttaga ggtggtgttc ttcgagttca gtatgaagga   3240
ggaactgagg acgaactcat tcgcctaact cacgcaggtg tatcagtatc aggttttgat   3300
acgcatcata agggagaaca gaatcttact ctccaatatt tgggacaacc agtaaatgct   3360
aatttgtcag tgactgtcac tggccaagac gaagcaagtc cgaaaactat tttgggaatt   3420
gaagtaagtc agaaaccgaa aaaagattac ctagttggtg atagcttaga cttgtctgaa   3480
ggacgctttg cagtggctta tagcaatgac accatggaag aacattcctt tactgatgag   3540
ggagttgaaa tttctggtta cgatgctcaa aagactggtc gtcaaacctt gacgcttcgt   3600
taccaaggtc atgaagtcaa ctttgatgtt ttggtatctc caaaagcagc attgaacgat   3660
gagtacctca acaaaaaatt agcagaagtt gaagctgcta agaacaaggt ggtctataac   3720
```

-continued

```
tttgcttcac cagaagtaaa agaagctttc ttgaaagcaa ttgaagcggc cgaacaagtg    3780
ttgaaagacc atgaaattag cacccaagat caagtcaatg accgacttaa taaattgaca    3840
gaagctcata aagctctgaa tggtcaagag aaatttaagg aagaaaagac agagcttgat    3900
cgtttaacag gtgaggttca agaactcttg gatgccaaac caaaccatcc ttcaggttct    3960
gccctagctc cgcttcttga aaaaacaag gtcttggttg aaaaagtaga tttgagtcca    4020
gaagagcttg caacagcgaa acagagtcta aagatctgg ttgctttatt gaaagaagac    4080
aagccagcag tcttttctga tagtaaaaca ggtgttgaag tacacttctc aaataaagag    4140
aagactgtca tcaagggttt gaaagtagag cgtgttcaag caagtgctga agagaagaaa    4200
tactttgctg agaagatgc tcatgtcttt gaaatagaag gtttggatga aaaaggtcaa    4260
gatgttgatc tctcttacgc ttctattgtg aaaatcccaa ttgaaaaaga taagaaagtt    4320
aagaaagtat ttttcttacc tgaaggcaaa gaggcagtag aattggcttt tgaacaaacg    4380
gatagtcatg ttatctttac agcaccacac tttactcatt atgcctttgt ttatgaatct    4440
gctgaaaaac cacaacctgc taaaccagca ccacaaaaca aagtccttcc aaaacctact    4500
tatcaaccgg cttctgatca acaaaaggct cctaaattgg aagttcaaga ggaaaaggtt    4560
gcctttcatc gtcaagagca tgaaaatgct gagatgctag ttggggaaca acgagtcatc    4620
atacagggac gagatggact gttaagacat gtctttgaag ttgatgaaaa cggtcagcgt    4680
cgtcttcgtt caacagaagt catccaagaa gcgattccag aaattgttga aattggaaca    4740
aaagtaaaaa cagtaccagc agtagtagct acacaggaaa aaccagctca aaatacagca    4800
gttaaatcag aagaagcaag caaacaattg ccaaatacag gaacagctga tgctaatgaa    4860
gccctaatag caggcttagc cagccttggt cttgctagtt tagccttgac cttgagacgg    4920
aaaagagaag ataaagatta a                                             4941
```

<210> SEQ ID NO 15
<211> LENGTH: 1606
<212> TYPE: PRT
<213> ORGANISM: Artificial Sequence
<220> FEATURE:
<223> OTHER INFORMATION: SYNTHETIC CONSTRUCT

<400> SEQUENCE: 15

```
Ala Val Pro Glu Asn Ser Gly Ala Asn Thr Glu Leu Val Ser Gly Glu
1               5                   10                  15

Ser Glu His Ser Thr Asn Glu Ala Asp Lys Gln Asn Glu Gly Glu His
            20                  25                  30

Thr Arg Glu Asn Lys Leu Glu Lys Ala Glu Gly Val Ala Thr Ala Ser
        35                  40                  45

Glu Thr Ala Glu Ala Ala Ser Ala Ala Lys Pro Glu Glu Lys Ala Gly
    50                  55                  60

Glu Val Val Ala Glu Thr Pro Ser Ala Glu Ala Lys Pro Lys Ser Asp
65                  70                  75                  80

Lys Glu Thr Glu Ala Lys Pro Glu Ala Thr Asn Gln Gly Asp Glu Ser
                85                  90                  95

Lys Pro Ala Ala Glu Ala Asn Lys Thr Glu Lys Glu Val Gln Pro Asp
            100                 105                 110

Val Pro Lys Asn Thr Glu Lys Thr Leu Lys Pro Lys Glu Ile Lys Phe
        115                 120                 125

Asn Ser Trp Glu Glu Leu Leu Lys Trp Glu Pro Gly Ala Arg Glu Asp
    130                 135                 140
```

```
Asp Ala Ile Asn Arg Gly Ser Val Val Leu Ala Ser Arg Arg Thr Gly
145                 150                 155                 160

His Leu Val Asn Glu Lys Ala Ser Lys Glu Ala Lys Val Gln Ala Leu
                165                 170                 175

Ser Asn Thr Asn Ser Lys Ala Lys Asp His Ala Ser Val Gly Gly Glu
            180                 185                 190

Glu Phe Lys Ala Tyr Ala Phe Asp Tyr Trp Gln Tyr Leu Asp Ser Met
        195                 200                 205

Val Phe Trp Glu Gly Leu Val Pro Thr Pro Asp Val Ile Asp Ala Gly
    210                 215                 220

His Arg Asn Gly Val Pro Val Tyr Gly Thr Leu Phe Phe Asn Trp Ser
225                 230                 235                 240

Asn Ser Ile Ala Asp Gln Glu Arg Phe Ala Glu Ala Leu Lys Gln Asp
                245                 250                 255

Ala Asp Gly Ser Phe Pro Ile Ala Arg Lys Leu Val Asp Met Ala Lys
            260                 265                 270

Tyr Tyr Gly Tyr Asp Gly Tyr Phe Ile Asn Gln Glu Thr Gly Asp
        275                 280                 285

Leu Val Lys Pro Leu Gly Glu Lys Met Arg Gln Phe Met Leu Tyr Ser
    290                 295                 300

Lys Glu Tyr Ala Ala Lys Val Asn His Pro Ile Lys Tyr Ser Trp Tyr
305                 310                 315                 320

Asp Ala Met Thr Tyr Asn Tyr Gly Arg Tyr His Gln Asp Gly Leu Gly
                325                 330                 335

Glu Tyr Asn Tyr Gln Phe Met Gln Pro Glu Gly Asp Lys Val Pro Ala
            340                 345                 350

Asp Asn Phe Phe Ala Asn Phe Asn Trp Asp Lys Ala Lys Asn Asp Tyr
        355                 360                 365

Thr Ile Ala Thr Ala Asn Trp Ile Gly Arg Asn Pro Tyr Asp Val Phe
    370                 375                 380

Ala Gly Leu Glu Leu Gln Gln Gly Gly Ser Tyr Lys Thr Lys Val Lys
385                 390                 395                 400

Trp Asn Asp Ile Leu Asp Glu Asn Gly Lys Leu Arg Leu Ser Leu Gly
                405                 410                 415

Leu Phe Ala Pro Asp Thr Ile Thr Ser Leu Gly Lys Thr Gly Glu Asp
            420                 425                 430

Tyr His Lys Asn Glu Asp Ile Phe Phe Thr Gly Tyr Gln Gly Asp Pro
        435                 440                 445

Thr Gly Gln Lys Pro Gly Asp Lys Asp Trp Tyr Gly Ile Ala Asn Leu
    450                 455                 460

Val Ala Asp Arg Thr Pro Ala Val Gly Asn Thr Phe Thr Thr Ser Phe
465                 470                 475                 480

Asn Thr Gly His Gly Lys Lys Trp Phe Val Asp Gly Lys Val Ser Lys
                485                 490                 495

Asp Ser Glu Trp Asn Tyr Arg Ser Ser Gly Val Leu Pro Thr Trp
            500                 505                 510

Arg Trp Trp Gln Thr Ser Thr Gly Glu Lys Leu Arg Ala Glu Tyr Asp
        515                 520                 525

Phe Thr Asp Ala Tyr Asn Gly Gly Asn Ser Leu Lys Phe Ser Gly Asp
    530                 535                 540

Val Ala Gly Lys Thr Asp Gln Asp Val Arg Leu Tyr Ser Thr Lys Leu
545                 550                 555                 560
```

-continued

Glu Val Thr Glu Lys Thr Lys Leu Arg Val Ala His Lys Gly Gly Lys
                565                 570                 575

Gly Ser Lys Val Tyr Met Ala Phe Ser Thr Thr Pro Asp Tyr Lys Phe
            580                 585                 590

Asp Asp Ala Asp Ala Trp Lys Glu Leu Thr Leu Ser Asp Asn Trp Thr
        595                 600                 605

Asn Glu Glu Phe Asp Leu Ser Ser Leu Ala Gly Lys Thr Ile Tyr Ala
    610                 615                 620

Val Lys Leu Phe Phe Glu His Glu Gly Ala Val Lys Asp Tyr Gln Phe
625                 630                 635                 640

Asn Leu Gly Gln Leu Thr Ile Ser Asp Asn His Gln Glu Pro Gln Ser
                645                 650                 655

Pro Thr Ser Phe Ser Val Val Lys Gln Ser Leu Lys Asn Ala Gln Glu
            660                 665                 670

Ala Glu Ala Val Val Gln Phe Lys Gly Asn Lys Asp Ala Asp Phe Tyr
        675                 680                 685

Glu Val Tyr Glu Lys Asp Gly Asp Ser Trp Lys Leu Leu Thr Gly Ser
    690                 695                 700

Ser Ser Thr Thr Ile Tyr Leu Pro Lys Val Ser Arg Ser Ala Ser Ala
705                 710                 715                 720

Gln Gly Thr Thr Gln Glu Leu Lys Val Val Ala Val Gly Lys Asn Gly
                725                 730                 735

Val Arg Ser Glu Ala Ala Thr Thr Thr Phe Asp Trp Gly Met Thr Val
            740                 745                 750

Lys Asp Thr Ser Leu Pro Lys Pro Leu Ala Glu Asn Ile Val Pro Gly
        755                 760                 765

Ala Thr Val Ile Asp Ser Thr Phe Pro Lys Thr Glu Gly Gly Glu Gly
    770                 775                 780

Ile Glu Gly Met Leu Asn Gly Thr Ile Thr Ser Leu Ser Asp Lys Trp
785                 790                 795                 800

Ser Ser Ala Gln Leu Ser Gly Ser Val Asp Ile Arg Leu Thr Lys Pro
                805                 810                 815

Arg Thr Val Val Arg Trp Val Met Asp His Ala Gly Ala Gly Gly Glu
            820                 825                 830

Ser Val Asn Asp Gly Leu Met Asn Thr Lys Asp Phe Asp Leu Tyr Tyr
        835                 840                 845

Lys Asp Ala Asp Gly Glu Trp Lys Leu Ala Lys Glu Val Arg Gly Asn
    850                 855                 860

Lys Ala His Val Thr Asp Ile Thr Leu Asp Lys Pro Ile Thr Ala Gln
865                 870                 875                 880

Asp Trp Arg Leu Asn Val Val Thr Ser Asp Asn Gly Thr Pro Trp Lys
                885                 890                 895

Ala Ile Arg Ile Tyr Asn Trp Lys Met Tyr Glu Lys Leu Asp Thr Glu
            900                 905                 910

Ser Val Asn Ile Pro Met Ala Lys Ala Ala Arg Ser Leu Gly Asn
        915                 920                 925

Asn Lys Val Gln Val Gly Phe Ala Asp Val Gln Ala Gly Ala Thr Ile
    930                 935                 940

Thr Val Tyr Asp Asn Pro Asn Ser Gln Thr Pro Leu Ala Thr Leu Lys
945                 950                 955                 960

Ser Glu Val Gly Gly Asp Leu Ala Ser Ala Pro Leu Asp Leu Thr Asn
                965                 970                 975

Gln Ser Gly Leu Leu Tyr Tyr Arg Thr Gln Leu Pro Gly Lys Glu Ile

-continued

Ser Asn Val Leu Ala Val Ser Val Pro Lys Asp Asp Arg Arg Ile Lys
   980             985             990
              995             1000            1005

Ser Val Ser Leu Glu Thr Gly Pro Lys Lys Thr Ser Tyr Ala Glu
   1010            1015            1020

Gly Glu Asp Leu Asp Leu Arg Gly Gly Val Leu Arg Val Gln Tyr
   1025            1030            1035

Glu Gly Gly Thr Glu Asp Glu Leu Ile Arg Leu Thr His Ala Gly
   1040            1045            1050

Val Ser Val Ser Gly Phe Asp Thr His His Lys Gly Glu Gln Asn
   1055            1060            1065

Leu Thr Leu Gln Tyr Leu Gly Gln Pro Val Asn Ala Asn Leu Ser
   1070            1075            1080

Val Thr Val Thr Gly Gln Asp Glu Ala Ser Pro Lys Thr Ile Leu
   1085            1090            1095

Gly Ile Val Ser Gln Lys Pro Lys Lys Asp Tyr Leu Val Gly Asp
   1100            1105            1110

Ser Leu Asp Leu Ser Glu Gly Arg Phe Ala Val Ala Tyr Ser Asn
   1115            1120            1125

Asp Thr Met Glu Glu His Ser Phe Thr Asp Glu Glu Gly Val Glu
   1130            1135            1140

Ile Ser Gly Tyr Asp Ala Gln Lys Thr Gly Arg Gln Thr Leu Thr
   1145            1150            1155

Leu Arg Tyr Gln Gly His Glu Val Asn Phe Asp Val Leu Val Ser
   1160            1165            1170

Pro Lys Ala Ala Leu Asn Asp Glu Tyr Leu Lys Gln Lys Leu Ala
   1175            1180            1185

Glu Val Glu Ala Ala Lys Asn Lys Val Val Tyr Asn Phe Ala Ser
   1190            1195            1200

Pro Glu Val Lys Glu Ala Phe Leu Lys Ala Ile Glu Ala Ala Glu
   1205            1210            1215

Gln Val Leu Lys Asp His Glu Ile Ser Thr Gln Asp Gln Val Asn
   1220            1225            1230

Asp Arg Leu Asn Lys Leu Thr Glu Ala His Lys Ala Leu Asn Gly
   1235            1240            1245

Gln Glu Lys Phe Lys Glu Glu Lys Thr Glu Leu Asp Arg Leu Thr
   1250            1255            1260

Gly Glu Val Gln Glu Leu Leu Asp Ala Lys Pro Asn His Pro Ser
   1265            1270            1275

Gly Ser Ala Leu Ala Pro Leu Leu Glu Lys Asn Lys Val Leu Val
   1280            1285            1290

Glu Lys Val Asp Leu Ser Pro Glu Glu Leu Ala Thr Ala Lys Gln
   1295            1300            1305

Ser Leu Lys Asp Leu Val Ala Leu Leu Lys Glu Asp Lys Pro Ala
   1310            1315            1320

Val Phe Ser Asp Ser Lys Thr Gly Val Glu Val His Phe Ser Asn
   1325            1330            1335

Lys Glu Lys Thr Val Ile Lys Gly Leu Lys Val Glu Arg Val Gln
   1340            1345            1350

Ala Ser Ala Glu Glu Lys Lys Tyr Phe Ala Gly Glu Asp Ala His
   1355            1360            1365

Val Phe Glu Ile Glu Gly Leu Asp Glu Lys Gly Gln Asp Val Asp
   1370            1375            1380

Leu Ser Tyr Ala Ser Ile Val Lys Ile Pro Ile Glu Lys Asp Lys
1385                1390                1395

Lys Val Lys Lys Val Phe Phe Leu Pro Glu Gly Lys Glu Ala Val
1400                1405                1410

Glu Leu Ala Phe Glu Gln Thr Asp Ser His Val Ile Phe Thr Ala
1415                1420                1425

Pro His Phe Thr His Tyr Ala Phe Val Tyr Glu Ser Ala Glu Lys
1430                1435                1440

Pro Gln Pro Ala Lys Pro Ala Pro Gln Asn Lys Val Leu Pro Lys
1445                1450                1455

Pro Thr Tyr Gln Pro Ala Ser Asp Gln Gln Lys Ala Pro Lys Leu
1460                1465                1470

Glu Val Gln Glu Glu Lys Val Ala Phe His Arg Gln Glu His Glu
1475                1480                1485

Asn Ala Glu Met Leu Val Gly Glu Gln Arg Val Ile Ile Gln Gly
1490                1495                1500

Arg Asp Gly Leu Leu Arg His Val Phe Glu Val Asp Glu Asn Gly
1505                1510                1515

Gln Arg Arg Leu Arg Ser Thr Glu Val Ile Gln Glu Ala Ile Pro
1520                1525                1530

Glu Ile Val Glu Ile Gly Thr Lys Val Lys Thr Val Pro Ala Val
1535                1540                1545

Val Ala Thr Gln Glu Lys Pro Ala Gln Asn Thr Ala Val Lys Ser
1550                1555                1560

Glu Glu Ala Ser Lys Gln Leu Pro Asn Thr Gly Thr Ala Asp Ala
1565                1570                1575

Asn Glu Ala Leu Ile Ala Gly Leu Ala Ser Leu Gly Leu Ala Ser
1580                1585                1590

Leu Ala Leu Thr Leu Arg Arg Lys Arg Glu Asp Lys Asp
1595                1600                1605

<210> SEQ ID NO 16
<211> LENGTH: 1606
<212> TYPE: PRT
<213> ORGANISM: Artificial Sequence
<220> FEATURE:
<223> OTHER INFORMATION: SYNTHETIC CONSTRUCT

<400> SEQUENCE: 16

Ala Val Pro Glu Asn Ser Gly Ala Asn Thr Glu Leu Val Ser Gly Glu
1               5                   10                  15

Ser Glu His Ser Thr Asn Glu Ala Asp Lys Gln Asn Glu Gly Glu His
                20                  25                  30

Thr Arg Glu Asn Lys Leu Glu Lys Ala Glu Gly Val Thr Ala Ser
        35                  40                  45

Glu Thr Ala Glu Ala Ala Ser Ala Ala Lys Pro Glu Glu Lys Ala Gly
    50                  55                  60

Glu Val Val Ala Glu Thr Pro Ser Ala Glu Ala Lys Pro Lys Ser Asp
65                  70                  75                  80

Lys Glu Thr Glu Ala Lys Pro Glu Ala Thr Asn Gln Gly Asp Glu Ser
                85                  90                  95

Lys Pro Ala Ala Glu Ala Asn Lys Thr Glu Lys Glu Val Gln Pro Asp
            100                 105                 110

Val Pro Lys Asn Thr Glu Lys Thr Leu Lys Pro Lys Glu Ile Lys Phe
        115                 120                 125

```
Asn Ser Trp Glu Glu Leu Leu Lys Trp Glu Pro Gly Ala Arg Glu Asp
            130                 135                 140

Asp Ala Ile Asn Arg Gly Ser Val Val Leu Ala Ser Arg Thr Gly
145                 150                 155                 160

His Leu Val Asn Glu Lys Ala Ser Lys Glu Ala Lys Val Gln Ala Leu
                165                 170                 175

Ser Asn Thr Asn Ser Lys Ala Lys Asp His Ala Ser Val Gly Gly Glu
            180                 185                 190

Glu Phe Lys Ala Tyr Ala Phe Asp Tyr Trp Gln Tyr Leu Asp Ser Met
        195                 200                 205

Val Phe Trp Glu Gly Leu Val Pro Thr Pro Asp Val Ile Asp Ala Gly
210                 215                 220

His Arg Asn Gly Val Pro Val Tyr Gly Thr Leu Phe Phe Asn Trp Ser
225                 230                 235                 240

Asn Ser Ile Ala Asp Gln Glu Arg Phe Ala Glu Ala Leu Lys Gln Asp
            245                 250                 255

Ala Asp Gly Ser Phe Pro Ile Ala Arg Lys Leu Val Asp Met Ala Lys
            260                 265                 270

Tyr Tyr Gly Tyr Asp Gly Tyr Phe Ile Asn Gln Glu Thr Thr Gly Asp
            275                 280                 285

Leu Val Lys Pro Leu Gly Glu Lys Met Arg Gln Phe Met Leu Tyr Ser
290                 295                 300

Lys Glu Tyr Ala Ala Lys Val Asn His Pro Ile Lys Tyr Ser Trp Tyr
305                 310                 315                 320

Asp Ala Met Thr Tyr Asn Tyr Gly Arg Tyr His Gln Asp Gly Leu Gly
                325                 330                 335

Glu Tyr Asn Tyr Gln Phe Met Gln Pro Glu Gly Asp Lys Val Pro Ala
            340                 345                 350

Asp Asn Phe Phe Ala Asn Phe Asn Trp Asp Lys Ala Lys Asn Asp Tyr
            355                 360                 365

Thr Ile Ala Thr Ala Asn Trp Ile Gly Arg Asn Pro Tyr Asp Val Phe
            370                 375                 380

Ala Gly Leu Glu Leu Gln Gln Gly Gly Ser Tyr Lys Thr Lys Val Lys
385                 390                 395                 400

Trp Asn Asp Ile Leu Asp Glu Asn Gly Lys Leu Arg Leu Ser Leu Gly
                405                 410                 415

Leu Phe Ala Pro Asp Thr Ile Thr Ser Leu Gly Lys Thr Gly Glu Asp
                420                 425                 430

Tyr His Lys Asn Glu Asp Ile Phe Phe Thr Gly Tyr Gln Gly Asp Pro
            435                 440                 445

Thr Gly Gln Lys Pro Gly Asp Lys Asp Trp Tyr Gly Ile Ala Asn Leu
            450                 455                 460

Val Ala Asp Arg Thr Pro Ala Val Gly Asn Thr Phe Thr Thr Ser Phe
465                 470                 475                 480

Asn Thr Gly His Gly Lys Lys Trp Phe Val Asp Gly Lys Val Ser Lys
                485                 490                 495

Asp Ser Glu Trp Asn Tyr Arg Ser Val Ser Gly Val Leu Pro Thr Trp
            500                 505                 510

Arg Trp Trp Gln Thr Ser Thr Gly Glu Lys Leu Arg Ala Glu Tyr Asp
            515                 520                 525

Phe Thr Asp Ala Tyr Asn Gly Gly Asn Ser Leu Lys Phe Ser Gly Asp
            530                 535                 540
```

```
Val Ala Gly Lys Thr Asp Gln Asp Val Arg Leu Tyr Ser Thr Lys Leu
545                 550                 555                 560

Glu Val Thr Glu Lys Thr Lys Leu Arg Val Ala His Lys Gly Gly Lys
                565                 570                 575

Gly Ser Lys Val Tyr Met Ala Phe Ser Thr Thr Pro Asp Tyr Lys Phe
            580                 585                 590

Asp Asp Ala Asp Ala Trp Lys Glu Leu Thr Leu Ser Asp Asn Trp Thr
        595                 600                 605

Asn Glu Glu Phe Asp Leu Ser Ser Leu Ala Gly Lys Thr Ile Tyr Ala
    610                 615                 620

Val Lys Leu Phe Phe Glu His Glu Gly Ala Val Lys Asp Tyr Gln Phe
625                 630                 635                 640

Asn Leu Gly Gln Leu Thr Ile Ser Asp Asn His Gln Glu Pro Gln Ser
                645                 650                 655

Pro Thr Ser Phe Ser Val Val Lys Gln Ser Leu Lys Asn Ala Gln Glu
            660                 665                 670

Ala Glu Ala Val Val Gln Phe Lys Gly Asn Lys Asp Ala Asp Phe Tyr
        675                 680                 685

Glu Val Tyr Glu Lys Asp Gly Asp Ser Trp Lys Leu Leu Thr Gly Ser
    690                 695                 700

Ser Ser Thr Thr Ile Tyr Leu Pro Lys Val Ser Arg Ser Ala Ser Ala
705                 710                 715                 720

Gln Gly Thr Thr Gln Glu Leu Lys Val Val Ala Val Gly Lys Asn Gly
                725                 730                 735

Val Arg Ser Glu Ala Ala Thr Thr Thr Phe Asp Trp Gly Met Thr Val
            740                 745                 750

Lys Asp Thr Ser Leu Pro Lys Pro Leu Ala Glu Asn Ile Val Pro Gly
        755                 760                 765

Ala Thr Val Ile Asp Ser Thr Phe Pro Lys Thr Glu Gly Gly Glu Gly
    770                 775                 780

Ile Glu Gly Met Leu Asn Gly Thr Ile Thr Ser Leu Ser Asp Lys Trp
785                 790                 795                 800

Ser Ser Ala Gln Leu Ser Gly Ser Val Asp Ile Arg Leu Thr Lys Pro
                805                 810                 815

Arg Thr Val Val Arg Trp Val Met Asp His Ala Gly Ala Gly Gly Glu
            820                 825                 830

Ser Val Asn Asp Gly Leu Met Asn Thr Lys Asp Phe Asp Leu Tyr Tyr
        835                 840                 845

Lys Asp Ala Asp Gly Glu Trp Lys Leu Ala Lys Glu Val Arg Gly Asn
    850                 855                 860

Lys Ala His Val Thr Asp Ile Thr Leu Asp Lys Pro Ile Thr Ala Gln
865                 870                 875                 880

Asp Trp Arg Leu Asn Val Val Thr Ser Asp Asn Gly Thr Pro Trp Lys
                885                 890                 895

Ala Ile Arg Ile Tyr Asn Trp Lys Met Tyr Glu Lys Leu Asp Thr Glu
            900                 905                 910

Ser Val Asn Ile Pro Met Ala Lys Ala Ala Arg Ser Leu Gly Asn
        915                 920                 925

Asn Lys Val Gln Val Gly Phe Ala Asp Val Gln Ala Gly Ala Thr Ile
    930                 935                 940

Thr Val Tyr Asp Asn Pro Asn Ser Gln Thr Pro Leu Ala Thr Leu Lys
945                 950                 955                 960

Ser Glu Val Gly Gly Asp Leu Ala Ser Ala Pro Leu Asp Leu Thr Asn
```

```
                965                 970                 975
Gln Ser Gly Leu Leu Tyr Tyr Arg Thr Gln Leu Pro Gly Lys Glu Ile
                980                 985                 990
Ser Asn Val Leu Ala Val Ser Val Pro Lys Asp Asp Arg Arg Ile Lys
        995                 1000                1005
Ser Val Ser Leu Glu Thr Gly Pro Lys Lys Thr Ser Tyr Ala Glu
    1010                1015                1020
Gly Glu Asp Leu Asp Leu Arg Gly Gly Val Leu Arg Val Gln Tyr
    1025                1030                1035
Glu Gly Gly Thr Glu Asp Glu Leu Ile Arg Leu Thr His Ala Gly
    1040                1045                1050
Val Ser Val Ser Gly Phe Asp Thr His His Lys Gly Glu Gln Asn
    1055                1060                1065
Leu Thr Leu Gln Tyr Leu Gly Gln Pro Val Asn Ala Asn Leu Ser
    1070                1075                1080
Val Thr Val Thr Gly Gln Asp Glu Ala Ser Pro Lys Thr Ile Leu
    1085                1090                1095
Gly Ile Val Ser Gln Lys Pro Lys Lys Asp Tyr Leu Val Gly Asp
    1100                1105                1110
Ser Leu Asp Leu Ser Glu Gly Arg Phe Ala Val Ala Tyr Ser Asn
    1115                1120                1125
Asp Thr Met Glu Glu His Ser Phe Thr Asp Glu Glu Gly Val Glu
    1130                1135                1140
Ile Ser Gly Tyr Asp Ala Gln Lys Thr Gly Arg Gln Thr Leu Thr
    1145                1150                1155
Leu Arg Tyr Gln Gly His Glu Val Asn Phe Asp Val Leu Val Ser
    1160                1165                1170
Pro Lys Ala Ala Leu Asn Asp Glu Tyr Leu Lys Gln Lys Leu Ala
    1175                1180                1185
Glu Val Glu Ala Ala Lys Asn Lys Val Val Tyr Asn Phe Ala Ser
    1190                1195                1200
Pro Glu Val Lys Glu Ala Phe Leu Lys Ala Ile Glu Ala Ala Glu
    1205                1210                1215
Gln Val Leu Lys Asp His Glu Ile Ser Thr Gln Asp Gln Val Asn
    1220                1225                1230
Asp Arg Leu Asn Lys Leu Thr Glu Ala His Lys Ala Leu Asn Gly
    1235                1240                1245
Gln Glu Lys Phe Lys Glu Lys Thr Glu Leu Asp Arg Leu Thr
    1250                1255                1260
Gly Glu Val Gln Glu Leu Leu Asp Ala Lys Pro Asn His Pro Ser
    1265                1270                1275
Gly Ser Ala Leu Ala Pro Leu Leu Glu Lys Asn Lys Val Leu Val
    1280                1285                1290
Glu Lys Val Asp Leu Ser Pro Glu Glu Leu Ala Thr Ala Lys Gln
    1295                1300                1305
Ser Leu Lys Asp Leu Val Ala Leu Leu Lys Glu Asp Lys Pro Ala
    1310                1315                1320
Val Phe Ser Asp Ser Lys Thr Gly Val Glu Val His Phe Ser Asn
    1325                1330                1335
Lys Glu Lys Thr Val Ile Lys Gly Leu Lys Val Glu Arg Val Gln
    1340                1345                1350
Ala Ser Ala Glu Glu Lys Lys Tyr Phe Ala Gly Glu Asp Ala His
    1355                1360                1365
```

```
Val Phe Glu Ile Glu Gly Leu Asp Glu Lys Gly Gln Asp Val Asp
    1370                1375                1380
Leu Ser Tyr Ala Ser Ile Val Lys Ile Pro Ile Glu Lys Asp Lys
    1385                1390                1395
Lys Val Lys Lys Val Phe Phe Leu Pro Glu Gly Lys Glu Ala Val
1400                1405                1410
Glu Leu Ala Phe Glu Gln Thr Asp Ser His Val Ile Phe Thr Ala
1415                1420                1425
Pro His Phe Thr His Tyr Ala Phe Val Tyr Glu Ser Ala Glu Lys
1430                1435                1440
Pro Gln Pro Ala Lys Pro Ala Pro Gln Asn Lys Val Leu Pro Lys
1445                1450                1455
Pro Thr Tyr Gln Pro Ala Ser Asp Gln Gln Lys Ala Pro Lys Leu
1460                1465                1470
Glu Val Gln Glu Glu Lys Val Ala Phe His Arg Gln Glu His Glu
1475                1480                1485
Asn Ala Glu Met Leu Val Gly Glu Gln Arg Val Ile Ile Gln Gly
1490                1495                1500
Arg Asp Gly Leu Leu Arg His Val Phe Glu Val Asp Glu Asn Gly
1505                1510                1515
Gln Arg Arg Leu Arg Ser Thr Glu Val Ile Gln Glu Ala Ile Pro
1520                1525                1530
Glu Ile Val Glu Ile Gly Thr Lys Val Lys Thr Val Pro Ala Val
1535                1540                1545
Val Ala Thr Gln Glu Lys Pro Ala Gln Asn Thr Ala Val Lys Ser
1550                1555                1560
Glu Glu Ala Ser Lys Gln Leu Pro Asn Thr Gly Thr Ala Asp Ala
1565                1570                1575
Asn Glu Ala Leu Ile Ala Gly Leu Ala Ser Leu Gly Leu Ala Ser
1580                1585                1590
Leu Ala Leu Thr Leu Arg Arg Lys Arg Glu Asp Lys Asp
1595                1600                1605

<210> SEQ ID NO 17
<211> LENGTH: 1606
<212> TYPE: PRT
<213> ORGANISM: Artificial Sequence
<220> FEATURE:
<223> OTHER INFORMATION: SYNTHETIC CONSTRUCT

<400> SEQUENCE: 17

Ala Val Pro Glu Asn Ser Gly Ala Asn Thr Glu Leu Val Ser Gly Glu
1               5                   10                  15
Ser Glu His Ser Thr Asn Glu Ala Asp Lys Gln Asn Glu Gly Glu His
                20                  25                  30
Thr Arg Glu Asn Lys Leu Glu Lys Ala Glu Gly Val Ala Thr Ala Ser
            35                  40                  45
Glu Thr Ala Glu Ala Ala Ser Ala Ala Lys Pro Glu Glu Lys Ala Gly
        50                  55                  60
Glu Val Val Ala Glu Thr Pro Ser Ala Glu Ala Lys Pro Lys Ser Asp
65                  70                  75                  80
Lys Glu Thr Glu Ala Lys Pro Glu Ala Thr Asn Gln Gly Asp Glu Ser
                85                  90                  95
Lys Pro Ala Ala Glu Ala Asn Lys Thr Glu Lys Glu Val Gln Pro Asp
            100                 105                 110
```

```
Val Pro Lys Asn Thr Glu Lys Thr Leu Lys Pro Lys Glu Ile Lys Phe
            115                 120                 125

Asn Ser Trp Glu Glu Leu Leu Lys Trp Glu Pro Gly Ala Arg Glu Asp
        130                 135                 140

Asp Ala Ile Asn Arg Gly Ser Val Val Leu Ala Ser Arg Arg Thr Gly
145                 150                 155                 160

His Leu Val Asn Glu Lys Ala Ser Lys Glu Ala Lys Val Gln Ala Leu
                165                 170                 175

Ser Asn Thr Asn Ser Lys Ala Lys Asp His Ala Ser Val Gly Gly Glu
            180                 185                 190

Glu Phe Lys Ala Tyr Ala Phe Asp Tyr Trp Gln Tyr Leu Asp Ser Met
        195                 200                 205

Val Phe Trp Glu Gly Leu Val Pro Thr Pro Asp Val Ile Asp Ala Gly
210                 215                 220

His Arg Asn Gly Val Pro Val Tyr Gly Thr Leu Phe Phe Asn Trp Ser
225                 230                 235                 240

Asn Ser Ile Ala Asp Gln Glu Arg Phe Ala Glu Ala Leu Lys Gln Asp
                245                 250                 255

Ala Asp Gly Ser Phe Pro Ile Ala Arg Lys Leu Val Asp Met Ala Lys
            260                 265                 270

Tyr Tyr Gly Tyr Asp Gly Tyr Phe Ile Gln Gln Glu Thr Thr Gly Asp
        275                 280                 285

Leu Val Lys Pro Leu Gly Glu Lys Met Arg Gln Phe Met Leu Tyr Ser
290                 295                 300

Lys Glu Tyr Ala Ala Lys Val Asn His Pro Ile Lys Tyr Ser Trp Tyr
305                 310                 315                 320

Asp Ala Met Thr Tyr Asn Tyr Gly Arg Tyr His Gln Asp Gly Leu Gly
                325                 330                 335

Glu Tyr Asn Tyr Gln Phe Met Gln Pro Glu Gly Asp Lys Val Pro Ala
        340                 345                 350

Asp Asn Phe Phe Ala Asn Phe Asn Trp Asp Lys Ala Lys Asn Asp Tyr
            355                 360                 365

Thr Ile Ala Thr Ala Asn Trp Ile Gly Arg Asn Pro Tyr Asp Val Phe
370                 375                 380

Ala Gly Leu Glu Leu Gln Gln Gly Gly Ser Tyr Lys Thr Lys Val Lys
385                 390                 395                 400

Trp Asn Asp Ile Leu Asp Glu Asn Gly Lys Leu Arg Leu Ser Leu Gly
                405                 410                 415

Leu Phe Ala Pro Asp Thr Ile Thr Ser Leu Gly Lys Thr Gly Glu Asp
        420                 425                 430

Tyr His Lys Asn Glu Asp Ile Phe Phe Thr Gly Tyr Gln Gly Asp Pro
            435                 440                 445

Thr Gly Gln Lys Pro Gly Asp Lys Asp Trp Tyr Gly Ile Ala Asn Leu
450                 455                 460

Val Ala Asp Arg Thr Pro Ala Val Gly Asn Thr Phe Thr Thr Ser Phe
465                 470                 475                 480

Asn Thr Gly His Gly Lys Lys Trp Phe Val Asp Gly Lys Val Ser Lys
                485                 490                 495

Asp Ser Glu Trp Asn Tyr Arg Ser Val Ser Gly Val Leu Pro Thr Trp
        500                 505                 510

Arg Trp Trp Gln Thr Ser Thr Gly Glu Lys Leu Arg Ala Glu Tyr Asp
            515                 520                 525
```

-continued

```
Phe Thr Asp Ala Tyr Asn Gly Gly Asn Ser Leu Lys Phe Ser Gly Asp
    530                 535                 540
Val Ala Gly Lys Thr Asp Gln Asp Val Arg Leu Tyr Ser Thr Lys Leu
545                 550                 555                 560
Glu Val Thr Glu Lys Thr Lys Leu Arg Val Ala His Lys Gly Gly Lys
                565                 570                 575
Gly Ser Lys Val Tyr Met Ala Phe Ser Thr Thr Pro Asp Tyr Lys Phe
            580                 585                 590
Asp Asp Ala Asp Ala Trp Lys Glu Leu Thr Leu Ser Asp Asn Trp Thr
        595                 600                 605
Asn Glu Glu Phe Asp Leu Ser Ser Leu Ala Gly Lys Thr Ile Tyr Ala
    610                 615                 620
Val Lys Leu Phe Phe Glu His Glu Gly Ala Val Lys Asp Tyr Gln Phe
625                 630                 635                 640
Asn Leu Gly Gln Leu Thr Ile Ser Asp Asn His Gln Glu Pro Gln Ser
                645                 650                 655
Pro Thr Ser Phe Ser Val Val Lys Gln Ser Leu Lys Asn Ala Gln Glu
            660                 665                 670
Ala Glu Ala Val Val Gln Phe Lys Gly Asn Lys Asp Ala Asp Phe Tyr
        675                 680                 685
Glu Val Tyr Glu Lys Asp Gly Asp Ser Trp Lys Leu Leu Thr Gly Ser
    690                 695                 700
Ser Ser Thr Thr Ile Tyr Leu Pro Lys Val Ser Arg Ser Ala Ser Ala
705                 710                 715                 720
Gln Gly Thr Thr Gln Glu Leu Lys Val Val Ala Val Gly Lys Asn Gly
                725                 730                 735
Val Arg Ser Glu Ala Ala Thr Thr Thr Phe Asp Trp Gly Met Thr Val
            740                 745                 750
Lys Asp Thr Ser Leu Pro Lys Pro Leu Ala Glu Asn Ile Val Pro Gly
        755                 760                 765
Ala Thr Val Ile Asp Ser Thr Phe Pro Lys Thr Glu Gly Gly Glu Gly
    770                 775                 780
Ile Glu Gly Met Leu Asn Gly Thr Ile Thr Ser Leu Ser Asp Lys Trp
785                 790                 795                 800
Ser Ser Ala Gln Leu Ser Gly Ser Val Asp Ile Arg Leu Thr Lys Pro
                805                 810                 815
Arg Thr Val Val Arg Trp Val Met Asp His Ala Gly Ala Gly Gly Glu
            820                 825                 830
Ser Val Asn Asp Gly Leu Met Asn Thr Lys Asp Phe Asp Leu Tyr Tyr
        835                 840                 845
Lys Asp Ala Asp Gly Glu Trp Lys Leu Ala Lys Glu Val Arg Gly Asn
    850                 855                 860
Lys Ala His Val Thr Asp Ile Thr Leu Asp Lys Pro Ile Thr Ala Gln
865                 870                 875                 880
Asp Trp Arg Leu Asn Val Val Thr Ser Asp Asn Gly Thr Pro Trp Lys
                885                 890                 895
Ala Ile Arg Ile Tyr Asn Trp Lys Met Tyr Glu Lys Leu Asp Thr Glu
            900                 905                 910
Ser Val Asn Ile Pro Met Ala Lys Ala Ala Arg Ser Leu Gly Asn
        915                 920                 925
Asn Lys Val Gln Val Gly Phe Ala Asp Val Gln Ala Gly Ala Thr Ile
    930                 935                 940
Thr Val Tyr Asp Asn Pro Asn Ser Gln Thr Pro Leu Ala Thr Leu Lys
```

```
            945                 950                 955                 960
Ser Glu Val Gly Gly Asp Leu Ala Ser Ala Pro Leu Asp Leu Thr Asn
                    965                 970                 975
Gln Ser Gly Leu Leu Tyr Tyr Arg Thr Gln Leu Pro Gly Lys Glu Ile
                980                 985                 990
Ser Asn Val Leu Ala Val Ser Val Pro Lys Asp Asp Arg Arg Ile Lys
                995                 1000                1005
Ser Val Ser Leu Glu Thr Gly Pro Lys Lys Thr Ser Tyr Ala Glu
    1010                1015                1020
Gly Glu Asp Leu Asp Leu Arg Gly Gly Val Leu Arg Val Gln Tyr
    1025                1030                1035
Glu Gly Gly Thr Glu Asp Glu Leu Ile Arg Leu Thr His Ala Gly
    1040                1045                1050
Val Ser Val Ser Gly Phe Asp Thr His His Lys Gly Glu Gln Asn
    1055                1060                1065
Leu Thr Leu Gln Tyr Leu Gly Gln Pro Val Asn Ala Asn Leu Ser
    1070                1075                1080
Val Thr Val Thr Gly Gln Asp Glu Ala Ser Pro Lys Thr Ile Leu
    1085                1090                1095
Gly Ile Val Ser Gln Lys Pro Lys Lys Asp Tyr Leu Val Gly Asp
    1100                1105                1110
Ser Leu Asp Leu Ser Glu Gly Arg Phe Ala Val Ala Tyr Ser Asn
    1115                1120                1125
Asp Thr Met Glu Glu His Ser Phe Thr Asp Glu Gly Val Glu
    1130                1135                1140
Ile Ser Gly Tyr Asp Ala Gln Lys Thr Gly Arg Gln Thr Leu Thr
    1145                1150                1155
Leu Arg Tyr Gln Gly His Glu Val Asn Phe Asp Val Leu Val Ser
    1160                1165                1170
Pro Lys Ala Ala Leu Asn Asp Glu Tyr Leu Lys Gln Lys Leu Ala
    1175                1180                1185
Glu Val Glu Ala Ala Lys Asn Lys Val Val Tyr Asn Phe Ala Ser
    1190                1195                1200
Pro Glu Val Lys Glu Ala Phe Leu Lys Ala Ile Glu Ala Ala Glu
    1205                1210                1215
Gln Val Leu Lys Asp His Glu Ile Ser Thr Gln Asp Gln Val Asn
    1220                1225                1230
Asp Arg Leu Asn Lys Leu Thr Glu Ala His Lys Ala Leu Asn Gly
    1235                1240                1245
Gln Glu Lys Phe Lys Glu Glu Lys Thr Glu Leu Asp Arg Leu Thr
    1250                1255                1260
Gly Glu Val Gln Glu Leu Leu Asp Ala Lys Pro Asn His Pro Ser
    1265                1270                1275
Gly Ser Ala Leu Ala Pro Leu Leu Glu Lys Asn Lys Val Leu Val
    1280                1285                1290
Glu Lys Val Asp Leu Ser Pro Glu Glu Leu Ala Thr Ala Lys Gln
    1295                1300                1305
Ser Leu Lys Asp Leu Val Ala Leu Leu Lys Glu Asp Lys Pro Ala
    1310                1315                1320
Val Phe Ser Asp Ser Lys Thr Gly Val Glu Val His Phe Ser Asn
    1325                1330                1335
Lys Glu Lys Thr Val Ile Lys Gly Leu Lys Val Glu Arg Val Gln
    1340                1345                1350
```

```
Ala Ser Ala Glu Glu Lys Lys Tyr Phe Ala Gly Glu Asp Ala His
    1355            1360            1365

Val Phe Glu Ile Glu Gly Leu Asp Glu Lys Gly Gln Asp Val Asp
    1370            1375            1380

Leu Ser Tyr Ala Ser Ile Val Lys Ile Pro Ile Glu Lys Asp Lys
    1385            1390            1395

Lys Val Lys Lys Val Phe Phe Leu Pro Glu Gly Lys Glu Ala Val
    1400            1405            1410

Glu Leu Ala Phe Glu Gln Thr Asp Ser His Val Ile Phe Thr Ala
    1415            1420            1425

Pro His Phe Thr His Tyr Ala Phe Val Tyr Glu Ser Ala Glu Lys
    1430            1435            1440

Pro Gln Pro Ala Lys Pro Ala Pro Gln Asn Lys Val Leu Pro Lys
    1445            1450            1455

Pro Thr Tyr Gln Pro Ala Ser Asp Gln Gln Lys Ala Pro Lys Leu
    1460            1465            1470

Glu Val Gln Glu Glu Lys Val Ala Phe His Arg Gln Glu His Glu
    1475            1480            1485

Asn Ala Glu Met Leu Val Gly Glu Gln Arg Val Ile Ile Gln Gly
    1490            1495            1500

Arg Asp Gly Leu Leu Arg His Val Phe Glu Val Asp Glu Asn Gly
    1505            1510            1515

Gln Arg Arg Leu Arg Ser Thr Glu Val Ile Gln Glu Ala Ile Pro
    1520            1525            1530

Glu Ile Val Glu Ile Gly Thr Lys Val Lys Thr Val Pro Ala Val
    1535            1540            1545

Val Ala Thr Gln Glu Lys Pro Ala Gln Asn Thr Ala Val Lys Ser
    1550            1555            1560

Glu Glu Ala Ser Lys Gln Leu Pro Asn Thr Gly Thr Ala Asp Ala
    1565            1570            1575

Asn Glu Ala Leu Ile Ala Gly Leu Ala Ser Leu Gly Leu Ala Ser
    1580            1585            1590

Leu Ala Leu Thr Leu Arg Arg Lys Arg Glu Asp Lys Asp
    1595            1600            1605
```